United States Patent
Wang et al.

(10) Patent No.: US 9,447,187 B2
(45) Date of Patent: Sep. 20, 2016

(54) USE OF AN ANTI-CD200 ANTIBODY FOR PROLONGING THE SURVIVAL OF ALLOGRAFTS

(75) Inventors: Yi Wang, Woodbridge, CT (US); Susan Faas McKnight, Old Lyme, CT (US); Zhao Xue Yu, Cheshire, CT (US); Hao Wang, London (CA)

(73) Assignee: Alexion Pharmaceuticals, Inc., New Haven, CT (US)

( * ) Notice: Subject to any disclaimer, the term of this patent is extended or adjusted under 35 U.S.C. 154(b) by 218 days.

(21) Appl. No.: 13/983,415

(22) PCT Filed: Feb. 3, 2012

(86) PCT No.: PCT/US2012/023831
§ 371 (c)(1),
(2), (4) Date: Nov. 26, 2013

(87) PCT Pub. No.: WO2012/106634
PCT Pub. Date: Aug. 9, 2012

(65) Prior Publication Data
US 2014/0170143 A1 Jun. 19, 2014

Related U.S. Application Data

(60) Provisional application No. 61/439,277, filed on Feb. 3, 2011.

(51) Int. Cl.
| | |
|---|---|
| C07K 16/28 | (2006.01) |
| A61K 39/395 | (2006.01) |
| A61K 31/365 | (2006.01) |
| A61K 31/436 | (2006.01) |
| A61K 38/13 | (2006.01) |
| A61K 45/06 | (2006.01) |
| G01N 33/68 | (2006.01) |
| A61K 9/00 | (2006.01) |
| A61K 31/439 | (2006.01) |
| A61K 31/5377 | (2006.01) |
| A61K 39/00 | (2006.01) |

(52) U.S. Cl.
CPC ......... *C07K 16/2803* (2013.01); *A61K 9/0019* (2013.01); *A61K 31/365* (2013.01); *A61K 31/436* (2013.01); *A61K 31/439* (2013.01); *A61K 31/5377* (2013.01); *A61K 38/13* (2013.01); *A61K 39/3955* (2013.01); *A61K 39/39533* (2013.01); *A61K 45/06* (2013.01); *G01N 33/6893* (2013.01); *A61K 2039/505* (2013.01); *A61K 2300/00* (2013.01); *C07K 2317/52* (2013.01); *C07K 2317/71* (2013.01); *C07K 2317/76* (2013.01); *G01N 2333/70596* (2013.01); *G01N 2800/245* (2013.01); *G01N 2800/347* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 7,408,041 B2 | 8/2008 | Bowdish et al. | |
| 7,427,665 B2 | 9/2008 | Bowdish et al. | |
| 7,435,412 B2 | 10/2008 | Bowdish et al. | |
| 7,435,415 B2 | 10/2008 | Gelber | |
| 7,598,353 B2 | 10/2009 | Bowdish et al. | |
| 7,714,110 B2 | 5/2010 | Bowdish et al. | |
| 7,915,000 B2 | 3/2011 | Bowdish et al. | |
| 8,075,884 B2 | 12/2011 | Bowdish et al. | |
| 8,114,403 B2 | 2/2012 | Bowdish et al. | |
| 8,187,877 B2 | 5/2012 | Bowdish et al. | |
| 8,252,285 B2 * | 8/2012 | Rother et al. | 424/130.1 |
| 8,637,014 B2 | 1/2014 | Rother et al. | |
| 8,709,415 B2 | 4/2014 | Bowdish et al. | |
| 8,840,885 B2 | 9/2014 | Bowdish et al. | |
| 8,986,684 B2 | 3/2015 | Wang | |
| 8,999,328 B2 | 4/2015 | Bowdish et al. | |
| 9,000,133 B2 | 4/2015 | Bowdish et al. | |
| 9,085,623 B2 | 7/2015 | Rother et al. | |
| 9,150,661 B2 | 10/2015 | Bowdish et al. | |
| 9,180,186 B2 | 11/2015 | Faas McKnight et al. | |
| 9,249,229 B2 | 2/2016 | Bowdish et al. | |
| 2004/0198661 A1 | 10/2004 | Bowdish et al. | |
| 2005/0074452 A1 | 4/2005 | Bowdish et al. | |
| 2006/0057651 A1 | 3/2006 | Bowdish et al. | |

(Continued)

FOREIGN PATENT DOCUMENTS

| | | |
|---|---|---|
| WO | WO-2004060295 | 7/2004 |
| WO | 2007/037795 A2 | 4/2007 |

(Continued)

OTHER PUBLICATIONS

International Search Report and Written Opinion dated May 29, 2012 for Application No. PCT/US2012/023831.
Partial Supplementary European Search Report, EP 12741568.5, dated May 13, 2015, pp. 1-4.
Lian, D. et al., "Synergy of Novel Anti-CD200 Antibody and Cyclosporine Enhances Myeloid-Derived Suppressor Cell Frequency and Leads to Long-Term Heart Allograft Survival," American Journal of Transplantation, vol. 11, Poster Board No. Session: P110.5-IV, p. 476, XP002739069, Apr. 4, 2011.

(Continued)

*Primary Examiner* — Ilia Ouspenski
(74) *Attorney, Agent, or Firm* — Nelson Mullins Riley & Scarborough LLP; Jane E. Remillard, Esq.; Christopher L. Frank

(57) ABSTRACT

The present disclosure provides methods useful for prolonging the survival of an allograft organ in a recipient mammal. The methods include administration of an anti-CD200 antibody or a CD200-binding fragment of the antibody. The disclosure also provides biomarkers, a change in one or more of which indicates that an anti-CD200 antibody has produced a desired immunomodulatory effect in a mammal. Also featured are pharmaceutical compositions, kits, and solutions that contain at least one anti-CD200 antibody and are useful in the methods described herein.

23 Claims, 16 Drawing Sheets

(56) References Cited

U.S. PATENT DOCUMENTS

| | | | |
|---|---|---|---|
| 2010/0285030 A1* | 11/2010 | Bowdish et al. | 424/172.1 |
| 2010/0291085 A1* | 11/2010 | Rother et al. | 424/135.1 |
| 2013/0158236 A1 | 6/2013 | Bowdish et al. | |
| 2013/0189258 A1 | 7/2013 | Rother et al. | |
| 2013/0202602 A1 | 8/2013 | Faas McKnight et al. | |
| 2015/0368341 A1 | 12/2015 | Bowdish et al. | |

FOREIGN PATENT DOCUMENTS

| | | |
|---|---|---|
| WO | WO-2007084321 | 7/2007 |
| WO | 2009/014744 A1 | 1/2009 |
| WO | 2009/014745 A1 | 1/2009 |
| WO | WO-2009014744 | 1/2009 |
| WO | WO-2009014745 | 1/2009 |
| WO | 2009/037190 A2 | 3/2009 |

OTHER PUBLICATIONS

Supplementay European Search Report, EP 12741568, dated Sep. 23, 2015, 12 pages.

Mahadevan, D., et al., "First-in-Human Phase I Dose Escalation Study of a Humanized Anti-CD200 Antibody (Samalizumab) in Patients with Advanced Stage B Cell Chronic Lymphocytic Leukemia (B-CLL) or Multiple Myeloma (MM)," Blood, 116(21):2465-2467 (2010).

U.S. Appl. No. 12/087,683, filed Jan. 14, 2009, Katherine S. Bowdish.
U.S. Appl. No. 13/311,910, filed Dec. 6, 2011, Katherine S. Bowdish.
U.S. Appl. No. 13/771,911, filed Feb. 20, 2013, Katherine S. Bowdish.
U.S. Appl. No. 10/379,151, filed Mar. 4, 2003, Katherine S. Bowdish.
U.S. Appl. No. 10/736,188, filed Dec. 15, 2003, Katherine S. Bowdish.
U.S. Appl. No. 10/894,672, filed Jul. 20, 2004, Katherine S. Bowdish.
U.S. Appl. No. 12/221,134, filed Jul. 30, 2008, Katherine S. Bowdish.
U.S. Appl. No. 12/221,122, filed Jul. 30, 2008, Katherine S. Bowdish.
U.S. Appl. No. 12/715,303, filed Mar. 1, 2010, Katherine S. Bowdish.
U.S. Appl. No. 13/344,195, filed Jan. 5, 2012, Katherine S. Bowdish.
U.S. Appl. No. 10/996,316, filed Nov. 23, 2004, Katherine S. Bowdish.
U.S. Appl. No. 11/171,567, filed Jun. 30, 2005, Katherine S. Bowdish.
U.S. Appl. No. 11/985,322, filed Nov. 13, 2007, Katherine S. Bowdish.
U.S. Appl. No. 13/072,470, filed Mar. 25, 2011, Katherine S. Bowdish.
U.S. Appl. No. 12/286,759, filed Sep. 30, 2008, Katherine S. Bowdish.
U.S. Appl. No. 13/029,021, filed Feb. 16, 2011, Katherine S. Bowdish.
U.S. Appl. No. 10/433,207, filed May 30, 2003, Katherine S. Bowdish.
U.S. Appl. No. 13/533,546, filed Jun. 26, 2012, Russell P. Rother.
U.S. Appl. No. 14/080,457, filed Nov. 14, 2013, Russell P. Rother.
U.S. Appl. No. 12/452,772, filed Apr. 5, 2010, Yi Wang.
U.S. Appl. No. 13/521,671, filed Apr. 17, 2013, Susan Faas McKnight.
U.S. Appl. No. 13/578,367, filed Jan. 18, 2013, Russell P. Rother.
U.S. Appl. No. 12/670,379, filed Jul. 20, 2010, Russell P. Rother.
U.S. Appl. No. 14/630,262, filed Feb. 24, 2015, Katherine S. Bowdish.
U.S. Appl. No. 12/087,683, Aug. 5, 2011.
U.S. Appl. No. 12/087,683, May 24, 2011.
U.S. Appl. No. 12/087,683, Jan. 4, 2011.
U.S. Appl. No. 12/087,683, Sep. 23, 2010.
U.S. Appl. No. 13/311,910, Dec. 13, 2013.
U.S. Appl. No. 13/311,910, Jul. 1, 2013.
U.S. Appl. No. 13/771,911, Oct. 23, 2014.
U.S. Appl. No. 13/771,911, Jul. 18, 2014.
U.S. Appl. No. 10/379,151, Jun. 4, 2008.
U.S. Appl. No. 10/379,151, Mar. 19, 2008.
U.S. Appl. No. 10/379,151, Sep. 24, 2007.
U.S. Appl. No. 10/379,151, Mar. 28, 2007.
U.S. Appl. No. 10/379,151, Jul. 13, 2006.
U.S. Appl. No. 10/379,151, Mar. 27, 2006.
U.S. Appl. No. 10/736,188, Apr. 3, 2008.
U.S. Appl. No. 10/736,188, Jul. 30, 2007.
U.S. Appl. No. 10/736,188, Jul. 26, 2006.
U.S. Appl. No. 10/894,672, Feb. 24, 2014.
U.S. Appl. No. 10/894,672, Dec. 23, 2013.
U.S. Appl. No. 10/894,672, Dec. 28, 2009.
U.S. Appl. No. 10/894,672, May 12, 2009.
U.S. Appl. No. 10/894,672, Oct. 15, 2008.
U.S. Appl. No. 10/894,672, Mar. 19, 2008.
U.S. Appl. No. 10/894,672, Nov. 7, 2007.
U.S. Appl. No. 10/894,672, May 14, 2007.
U.S. Appl. No. 10/894,672, Feb. 1, 2007.
U.S. Appl. No. 12/221,134, May 29, 2009.
U.S. Appl. No. 12/221,134, Feb. 25, 2009.
U.S. Appl. No. 12/221,122, Dec. 1, 2009.
U.S. Appl. No. 12/221,122, Jul. 24, 2009.
U.S. Appl. No. 12/221,122, Apr. 30, 2009.
U.S. Appl. No. 12/221,122, Jan. 23, 2009.
U.S. Appl. No. 12/715,303, Oct. 26, 2011.
U.S. Appl. No. 12/715,303, Jul. 11, 2011.
U.S. Appl. No. 12/715,303, Nov. 8, 2010.
U.S. Appl. No. 12/715,303, Jul. 22, 2010.
U.S. Appl. No. 13/344,195, Apr. 9, 2014.
U.S. Appl. No. 13/344,195, Dec. 2, 2013.
U.S. Appl. No. 13/344,195, Oct. 8, 2013.
U.S. Appl. No. 10/996,316, May 28, 2008.
U.S. Appl. No. 10/996,316, May 19, 2008.
U.S. Appl. No. 10/996,316, May 12, 2008.
U.S. Appl. No. 10/996,316, Feb. 8, 2008.
U.S. Appl. No. 10/996,316, Nov. 7, 2007.
U.S. Appl. No. 10/996,316, May 14, 2007.
U.S. Appl. No. 10/996,316, Feb. 21, 2007.
U.S. Appl. No. 11/171,567, May 14, 2007.
U.S. Appl. No. 11/171,567, Feb. 14, 2007.
U.S. Appl. No. 11/985,322, Nov. 30, 2010.
U.S. Appl. No. 11/985,322, Jul. 30, 2010.
U.S. Appl. No. 11/985,322, Oct. 5, 2009.
U.S. Appl. No. 11/985,322, Jun. 11, 2009.
U.S. Appl. No. 13/072,470, Nov. 25, 2014.
U.S. Appl. No. 13/072,470, Jul. 17, 2014.
U.S. Appl. No. 13/072,470, Feb. 28, 2014.
U.S. Appl. No. 13/072,470, Jun. 22, 2012.
U.S. Appl. No. 13/072,470, Jan. 27, 2012.
U.S. Appl. No. 13/072,470, Sep. 8, 2011.
U.S. Appl. No. 12/286,759, Feb. 21, 2012.
U.S. Appl. No. 12/286,759, Oct. 21, 2011.
U.S. Appl. No. 12/286,759, May 10, 2011.
U.S. Appl. No. 13/029,021, May 14, 2014.
U.S. Appl. No. 13/029,021, Nov. 21, 2013.
U.S. Appl. No. 13/029,021, Jul. 20, 2012.
U.S. Appl. No. 13/029,021, Feb. 16, 2012.
U.S. Appl. No. 10/433,207, Mar. 25, 2008.
U.S. Appl. No. 10/433,207, Oct. 31, 2007.
U.S. Appl. No. 10/433,207, May 2, 2007.
U.S. Appl. No. 10/433,207, Jul. 12, 2006.
U.S. Appl. No. 10/433,207, Mar. 29, 2006.
U.S. Appl. No. 13/533,546, Sep. 23, 2013.
U.S. Appl. No. 13/533,546, May 2, 2013.
U.S. Appl. No. 13/533,546, Mar. 14, 2013.
U.S. Appl. No. 12/452,772, Nov. 12, 2014.
U.S. Appl. No. 12/452,772, Mar. 13, 2014.

(56) References Cited

OTHER PUBLICATIONS

U.S. Appl. No. 12/452,772, May 25, 2012.
U.S. Appl. No. 12/452,772, Oct. 13, 2011.
U.S. Appl. No. 12/452,772, Aug. 4, 2011.
U.S. Appl. No. 13/521,671, Mar. 11, 2015.
U.S. Appl. No. 13/521,671, Nov. 10, 2014.
U.S. Appl. No. 12/670,379, Mar. 26, 2012.
U.S. Appl. No. 12/670,379, Oct. 19, 2011.
U.S. Appl. No. 12/670,379, Jul. 26, 2011.
U.S. Appl. No. 10/894,672, Katherine S. Bowdish, filed Jul. 20, 2004, May 22, 2015.
U.S. Appl. No. 13/344,195, Katherine S. Bowdish, filed Jan. 5, 2012, May 22, 2015.
U.S. Appl. No. 13/521,671, Susan Faas McKnight, filed Apr. 17, 2013, Jun. 23, 2015.
U.S. Appl. No. 13/578,367, Russell P. Rother, filed Jan. 18, 2013, Jun. 11, 2015.
U.S. Appl. No. 13/578,367, Russell P. Rother, filed Jan. 18, 2013, Mar. 5, 2015.
U.S. Appl. No. 13/578,367, Russell P. Rother, filed Jan. 18, 2013, Jul. 17, 2014.
U.S. Appl. No. 13/578,367, Russell P. Rother, filed Jan. 18, 2013, Feb. 20, 2014.
U.S. Appl. No. 10/894,672, Katherine S. Bowdish, filed Jul. 20, 2004, Sep. 18, 2015.
U.S. Appl. No. 14/969,731, filed Dec. 15, 2015, Katherine S. Bowdish.
U.S. Appl. No. 14/827,693, filed Aug. 17, 2015, Susan Faas McKnight.
U.S. Appl. No. 14/739,862, filed Jun. 15, 2015, Russell P. Rother.
U.S. Appl. No. 13/578,367, Jun. 11, 2015.

* cited by examiner

USE OF AN ANTI-CD200 ANTIBODY FOR PROLONGING THE SURVIVAL OF ALLOGRAFTS

CROSS-REFERENCE TO RELATED APPLICATIONS

This Application is a national stage filing under 35 U.S.C. 371 of International Application No. PCT/US12/23831, filed on Feb. 3, 2012, which claims priority to U.S. Application Ser. No. 61/439,277, filed on Feb. 3, 2011, the entire contents of which is hereby incorporated by reference. International Application No. PCT/US12/23831 was published under PCT Article 21(2) in English.

TECHNICAL FIELD

The field of the invention is medicine, immunology, molecular biology, and protein chemistry.

BACKGROUND

Transplantation of cells, tissues, and organs has become very common and is often a life-saving procedure. Organ transplantation is the preferred treatment for most patients with chronic organ failure. Despite great improvement in treatments to inhibit rejection, however, rejection continues to be the single largest impediment to successful organ transplantation. Rejection includes not only acute rejection but also chronic rejection. One-year survival rates for transplanted kidneys average 88.3% with kidneys from deceased donors and 94.4% with kidneys received from living donors.

The corresponding five year survival rates for the transplanted kidneys are 63.3% and 76.5%. [OPTN/SRTR Annual Report (2002) Chapter 1 of the Annual Report produced by the Scientific Registry of Transplant Recipients (SRTR) in collaboration with the Organ Procurement and Transplantation Network (OPTN).] The one year survival rates are 80.2% and 76.5% for livers from deceased and living donors, respectively. The corresponding five year liver graft survival rates are 63.5% and 73.0% (OPTN/SRTR Annual Report, 2002). The use of immunosuppressant drugs, e.g., cyclosporine A and more recently tacrolimus, has dramatically improved the success rate of organ transplantation especially by preventing acute rejection. But as the numbers above show, there is still a need to improve the success rates, both short-term and especially long-term. For example, as seen from the above numbers for kidney and liver transplants, the five year failure rates for these transplanted organs are on the order of 25-35%.

In the year 2001 alone there were more than 23,000 patients who received an organ transplant of which approximately 19,000 were kidney or liver (OPTN/SRTR Annual Report, 2002). For this one year of transplants alone, with present techniques it can be expected that approximately 5,000-6,000 of these transplanted kidneys and livers will fail within five years. These numbers do not even include other transplanted organs or transplanted tissues or cells such as bone marrow.

There are multiple types of transplants. These are described in Abbas et al. (2000) *Cell Mol Immunol* (4th edition), pages 363-383 (W.B. Saunders Company, New York). A graft transplanted from one individual to the same individual is called an autologous graft or autograft. A graft transplanted between two genetically identical or syngeneic individuals is called a syngeneic graft. A graft transplanted between two genetically different individuals of the same species is called an allogeneic graft or allograft. A graft transplanted between individuals of different species is called a xenogeneic graft or xenograft. The molecules that are recognized as foreign on allografts are called alloantigens and those on xenografts are called xenoantigens. The lymphocytes or antibodies that react with alloantigens or xenoantigens are described as being alloreactive or xenoreactive, respectively.

Currently more than 40,000 kidney, heart, lung, liver and pancreas transplants are performed in the United States each year (Abbas et al., 2000). Other possible transplants include, but are not limited to, vascular tissue, eye, cornea, lens, skin, bone marrow, muscle, connective tissue, gastrointestinal tissue, nervous tissue, bone, stem cells, islets, cartilage, hepatocytes, and hematopoietic cells. Unfortunately, there are many more candidates for a transplant than there are donors. In view of the foregoing number of transplants needed and the limitations of existing therapies, it is clear that new, therapeutically efficacious methods for prolonging the survival of allografts are needed.

SUMMARY

The present disclosure relates to compositions and methods useful for modulating an immune response in a mammal. As elaborated on in the description and exemplified in the working examples, the inventors have discovered that an anti-CD200 antibody is therapeutically effective as a single-agent therapy (such therapy is also referred to herein as a "monotherapy") to substantially prolong the survival of a renal allograft in a recipient mammal. The benefits of this discovery to transplant recipients are numerous. For example, use of an anti-CD200 antibody as a monotherapy can improve the quality of life for a renal allograft recipient, as allograft rejection is generally treated with one or more immunosuppressive agents, many of which either alone or in combination can result in serious side-effects such as alopecia, bone marrow depletion, gastrointestinal upset, pruritis, thrombocytopenia, anemia, nephrotoxicity, pancreatitis, and infection. Even within narrow therapeutic dose ranges, immunosuppressive agents (e.g., calcineurin inhibitors such as cyclosporine A (CsA) and FK-506) can be, for example, extremely nephrotoxic. Calne et al. (1978) *Lancet* 2:1323-1327 and Gaston (2009) *Clin J Am Soc Nephrol* 4(12):2029-2034. Treatment with subtherapeutic dosages of CsA or FK-506 results in significantly lower risk of nephrotoxicity, but with a significant reduction in therapeutic benefit with respect to graft survival. See, e.g., Seron and Moreso (2004) *Transplant Proc* 36:257S. Given the limitations and side effects attendant to calcineurin therapies, for example, it is clearly of great value to identify new compounds capable of reducing the requirement of these inhibitors (whether in dose level or length of treatment) while maintaining a high level of therapeutic efficacy with respect to prolonging graft survival. The disclosure demonstrates that an anti-CD200 antibody is such a compound.

The ability to prolong renal allograft survival using an anti-CD200 antibody, in the absence of one or more additional immunosuppressive agents, offers renal allograft recipients the same or even greater therapeutic effect without many of the debilitating side-effects associated with immunosuppressive agent therapy (e.g., combination therapy). Moreover, the one or more additional immunosuppressive agents often must be administered to the patient chronically or, perhaps, indefinitely in order to maintain graft survival. As is clear from the disclosure and exemplified in the working examples, an anti-CD200 antibody monotherapy can, in some embodiments, be administered for seven to fourteen days after transplantation and yet still achieve long-term survival of the grafts even without need for further immunosuppressive therapy.

Notwithstanding the efficacy of anti-CD200 antibody monotherapy, the anti-CD200 antibodies described herein are also useful as a therapeutic platform—offering flexible, alternative therapeutic options for transplant patients. For example, the inventors have discovered that therapeutic administration of an anti-CD200 antibody to an allograft-bearing mammal can allow for early withdrawal (and/or a reduced dose amount) of one or more additional immunosuppressive agents being administered to the mammal, yet still maintain therapeutic efficacy. As described in the working examples, administration of an anti-CD200 antibody to an allograft organ-bearing mammal allows for one or both of an early withdrawal and a lower dosage of a concurrent calcineurin inhibitor therapy, yet still maintain therapeutic efficacy in prolonging the survival of the allograft. In another example, mycophenolate-free or -reduced therapeutic options are also provided herein.

The inventors also discovered that subcutaneous administration—or a more localized or depot delivery—of an anti-CD200 antibody to a mammal can prolong the survival of an allograft organ as effectively as systemic delivery of the antibody. As exemplified in the working examples, subcutaneous administration of an anti-CD200 antibody as a monotherapy can substantially prolong the survival of a renal allograft in recipient mammals as well as intravenous delivery of the antibody. The examples also provide the results of experiments in which subcutaneous administration of an anti-CD200 antibody, in combination with one or more additional immunosuppressive agents, can prolong the survival of allograft organs such as a heart. Many benefits are attendant to subcutaneous or depot delivery of an anti-CD200 antibody. For example, for therapeutic applications that require frequent and/or chronic administration, subcutaneous or depot delivery can allow for fewer administrations of the therapeutic overall (with a higher concentration of the therapeutic to be deposited at each interval slowly releasing the compound to the mammal). Secondly, subcutaneous (or depot) delivery, along with systemic forms of delivery, of an anti-CD200 antibody provides more patient choice regarding how and when the therapeutic is administered. For example, in some embodiments, it can be possible for a patient to self-administer an anti-CD200 antibody, avoiding the need, for example, to travel to a hospital for such medication or arrange for an in-home nurse visit, which can be both costly and inconvenient. Therefore, increased patient choice ultimately manifests an increased patient compliance by providing an easy self-administration alternative for patients bearing an allograft.

To this end, the disclosure provides aqueous solutions comprising an anti-CD200 antibody, and therapeutic kits containing the solutions, for use in applications in which subcutaneous administration of the antibody would be beneficial. The solutions can contain the anti-CD200 antibody at a concentration of at least 10 mg/mL.

Accordingly, in one aspect, the disclosure features a method for prolonging the survival of a renal allograft. The method comprises administering to a recipient mammal in need thereof an anti-CD200 antibody as a single agent (a monotherapy) in an amount effective to prolong the survival of a renal allograft in the recipient mammal. In some embodiments, the method can also include transplanting the renal allograft into the recipient mammal. In some embodiments, the methods can further comprise, prior to removal from the donor mammal from which the renal allograft was obtained, administering an anti-CD200 antibody to the donor mammal.

In some embodiments, the anti-CD200 antibody is administered to the recipient mammal for at least seven (e.g., at least eight, nine, 10, 11, 12, 13, 14, 15, 16, 17, 18, 19, 20, 21, 22, 23, 24, 25, 26, 27, 28, 29, 30, 31) days following transplantation of the renal allograft into the recipient mammal. In some embodiments, the anti-CD200 antibody is administered at least once per day for up to seven (e.g., up to eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) days following transplantation of the renal allograft into the recipient mammal. In some embodiments, the anti-CD200 antibody is administered at least once per day for at least seven, but less than 30 (e.g., less than 29, 28, 27, 26, 25, 24, 23, 22, 21, 20, 19, 18, 17, 16, 15, 14, 13, 12, 11, 10, 9, or 8) days following transplantation of the renal allograft into the recipient mammal. In some embodiments, the anti-CD200 antibody can be administered in a dose large enough to remain effective for at least two (e.g., at least two, three, four, five, six, seven, eight, nine, ten, 11, 12, 13, or 14) days following transplantation of an allograft to the recipient mammal, with the antibody being administered as often as necessary to maintain an effective dose (e.g., a single dose may be large enough to remain effective for 14 days, in which event only a single dose would be required once every 14 days or only once if an effective amount of the antibody is required for only 14 days). In some embodiments, an effective amount of the anti-CD200 antibody is maintained in the recipient mammal for at least seven (e.g., at least eight, nine, 10, 11, 12, 13, 14, 15, 16, 17, 18, 19, 20, 21, 22, 23, 24, 25, 26, 27, or 28 or more) days. As noted above, it is understood that a single dose of the anti-CD200 antibody can be sufficient to maintain an effective amount of the anti-CD200 antibody in the mammal for at least seven (e.g., at least eight, nine, 10, 11, 12, 13, 14, 15, 16, 17, 18, 19, 20, 21, 22, 23, 24, 25, 26, 27, or 28 or more) days.

Though the particular dosing schedule (e.g., amount, frequency, and/or interval) employed may vary from patient to patient, an anti-CD200 antibody described herein can be administered to a mammal (e.g., a patient) in need thereof under such a regimen so as to maintain an effective amount of the antibody in the mammal for at least seven (e.g., at least eight, nine, 10, 11, 12, 13, 14, 15, 16, 17, 18, 19, 20, 21, 22, 23, 24, 25, 26, 27, 28, 29, 30, 31) days following transplantation of the renal allograft into the recipient mammal.

In some embodiments, the anti-CD200 antibody is administered to the recipient mammal prior to, and following, transplantation of the renal allograft into the recipient mammal. For example, the anti-CD200 antibody can be administered to the recipient mammal for at least one week prior to transplantation of the renal allograft into the recipient mammal. In some embodiments, at least two (e.g., at least three, four, five, six, seven, eight, nine, or even 10 or more) doses of the anti-CD200 antibody are administered to the recipient mammal prior to transplantation of the renal allograft into the recipient mammal.

In some embodiments, the renal allograft is fully MHC mismatched with respect to the recipient mammal. In some embodiments, the recipient mammal is presensitized to the renal allograft. In some embodiments, the renal allograft is an ABO-mismatch with respect to the recipient mammal.

In some embodiments, the anti-CD200 antibody is intravenously administered to the recipient mammal. In some embodiments, the anti-CD200 antibody is subcutaneously administered to the recipient mammal. In some embodiments, the anti-CD200 antibody is intramuscularly administered to the recipient mammal.

In some embodiments, administration of the anti-CD200 antibody results in renal allograft survival for at least 100 days. In some embodiments, administration of the anti-CD200 antibody results in a renal allograft survival of at least six months (e.g., seven months, eight months, nine months, 10 months, 11 months, 12 months, 16 months, 18 months, 20 months, or 24 months or more). In some embodiments, administration of the anti-CD200 antibody results in long term renal allograft survival.

In some embodiments, the recipient mammal and the renal allograft donor are human.

In another aspect, the disclosure features a method for prolonging the survival of an allograft organ in a recipient mammal, which method comprises administering to an allograft organ recipient in need thereof: (a) one or more immunosuppressive agents; and (b) an anti-CD200 antibody, to thereby prolong the survival of the graft in the patient. In some embodiments, administration of the anti-CD200 antibody allows for a shorter duration of treatment with at least one of the one or more immunosuppressive agents, relative to the duration of treatment with the at least one immunosuppressive agent in the absence of the anti-CD200 antibody. In some embodiments, administration of the anti-CD200 antibody allows for a reduced dose level or amount requirement for at least one of the one or more immunosuppressive agents, relative to the dose level or amount of the at least one immunosuppressive agent in the absence of the anti-CD200 antibody.

In some embodiments, at least one of the immunosuppressive agents can be an IL-2 inhibitor. For example, in some embodiments, at least one of the immunosuppressive agents is an mTOR inhibitor such as rapamycin. In some embodiments, at least one of the immunosuppressive agents is a calcineurin inhibitor such as cyclosporine A or FK-506.

In some embodiments, administration of the anti-CD200 antibody to the recipient mammal shortens the duration of treatment with at least one immunosuppressive agent by at least 20%. In some embodiments, administration of the anti-CD200 antibody to the recipient mammal shortens the duration of treatment with at least one immunosuppressive agent by at least 50%.

In some embodiments, the methods described herein provide an alternative therapeutic strategy for patients sensitive to mycophenolate therapy, e.g., MMF therapy. In such embodiments, the specification provides a mycophenolate-free alternative that includes administering to the patient an anti-CD200 antibody and a calcineurin inhibitor (e.g., cyclosporine A or tacrolimus), e.g., wherein the inhibitor is administered in an amount and/or a frequency that is less than the corresponding amount or frequency of the calcineurin inhibitor required to treat the patient in the absence of the anti-CD200 antibody therapy.

In some embodiments, e.g., where a patient is sensitive to calcineurin inhibitors, the methods described herein provide calcineurin inhibitor-free alternative options for patients in which an anti-CD200 antibody is administered to the patient in conjunction with a mycophenolate containing compound (e.g., MMF). The mycophenolate compound can be administered to the patient in an amount and/or at a frequency that is less than the amount or frequency of the compound required to treat the patient in the absence of the anti-CD200 antibody therapy.

In another aspect, the disclosure features a method for prolonging the survival of an allograft in a recipient mammal, the method comprising chronically administering to the mammal (e.g., a human): (a) an anti-CD200 antibody described herein and (b) a mycophenolate-containing compound (e.g., MMF) to thereby prolong the survival of the allograft in the mammal. In some embodiments, the anti-CD200 antibody and/or mycophenolate-containing compound is chronically administered for at least seven days. In some embodiments, the anti-CD200 antibody or mycophenolate-containing compound is chronically administered for at least 14 days. In some embodiments, chronic administration of the anti-CD200 antibody allows for a reduced amount and/or frequency of administration of the mycophenolate-containing compound required to maintain an effective amount in the mammal, as compared to the amount and/or frequency of the compound required to maintain an effective amount in the absence of the antibody.

In another aspect, the disclosure features a method for prolonging the survival of an allograft in a recipient mammal, the method comprising chronically administering to the mammal (e.g., a human): (a) an anti-CD200 antibody described herein and (b) an IL-2 inhibitor (e.g., a calcineurin inhibitor such as cyclosporine A) to thereby prolong the survival of the allograft in the mammal. In some embodiments, the anti-CD200 antibody and/or IL-2 inhibitor is chronically administered for at least seven days. In some embodiments, the anti-CD200 antibody or IL-2 inhibitor is chronically administered for at least 14 days. In some embodiments, chronic administration of the anti-CD200 antibody allows for a reduced amount and/or frequency of administration of the IL-2 inhibitor required to maintain an effective amount in the mammal, as compared to the amount and/or frequency of the inhibitor required to maintain an effective amount in the absence of the antibody.

In another aspect, the disclosure features a method for prolonging the survival of an allograft in a recipient mammal, wherein the method comprises: after (and, optionally prior to and/or during) transplantation of the allograft, administering to the recipient mammal: (a) an anti-CD200 antibody and (b) one or more additional immunosuppressive agents, wherein the one or more additional immunosuppressive agents include a mycophenolate compound (e.g., MMF) and an IL-2 inhibitor (such as a calcineurin inhibitor, e.g., cyclosporine A) and wherein one or more of the additional immunosuppressive agents are administered in a lower dose and/or less frequently than the dose or frequency required for equivalent therapeutic efficacy in the absence of the anti-CD200 antibody. An equivalent therapeutic efficacy can be, e.g., the standard or historical efficacy observed in a patient population administered the one or more additional immunosuppressive agents in the absence of a concomitant anti-CD200 antibody therapy.

It is understood that in combination therapies described herein including an anti-CD200 antibody and one or more immunosuppressants, "one or more immunosuppressive agents" can be used interchangeably with the term "one or more additional immunosuppressive agents".

In yet another aspect, the disclosure features a method for prolonging the survival of an allograft organ in a recipient mammal, which method comprises administering to an allograft organ recipient mammal in need thereof: (a) one or more immunosuppressive agents; and (b) an anti-CD200 antibody, to thereby prolong the survival of the graft in the mammal, wherein the anti-CD200 antibody is subcutaneously administered to the recipient mammal or intravenously administered to the recipient mammal.

In some embodiments, administration of the anti-CD200 antibody allows a shorter duration of treatment with at least one of the one or more immunosuppressive agents, relative to the duration of treatment with the at least one immunosuppressive agent in the absence of the anti-CD200 antibody. In some embodiments, administration of the anti-CD200 antibody allows for a reduced dose level or amount requirement for at least one of the one or more immunosuppressive agents, relative to the dose level or amount of the at least one immunosuppressive agent in the absence of the anti-CD200 antibody.

In some embodiments of any of the methods described herein, the anti-CD200 antibody is subcutaneously administered to the recipient mammal. In some embodiments of any of the methods described herein, the anti-CD200 antibody is intravenously administered to the recipient mammal.

In some embodiments of any of the methods described herein, the methods can further comprise, prior to removal from the donor mammal from which the allograft organ was obtained, administering an anti-CD200 antibody to the donor mammal.

In some embodiments, the allograft is fully MHC mismatched with respect to the recipient mammal. In some embodiments, the recipient mammal is presensitized to the allograft. In some embodiments, the allograft is an ABO-mismatch with respect to the recipient mammal.

In some embodiments, at least one of the one or more immunosuppressive agents is selected from the group consisting of adriamycin, azathioprine, busulfan, cyclophosphamide, fludarabine, 5-fluorouracil, methotrexate, mycophenolate mofetil, mycophenolate sodium, a non-steroidal anti-inflammatory drug, and an IL-2 inhibitor (e.g., an mTOR inhibitor such as rapamycin) or a calcineurin inhibitor such as FK-506 or cyclosporine A).

In some embodiments, two or more immunosuppressive agents are administered to the recipient mammal. In some embodiments, at least two of the two or more immunosuppressive agents are cyclosporine A and cyclophosphamide, FK-506 and cyclophosphamide, or a calcineurin inhibitor (cyclosporine A or FK-506) and a mycophenolate compound (e.g., mycophenolate mofetil or mycophenolate sodium).

In yet another aspect, the disclosure features a method for transplanting an allograft organ into a recipient mammal. The method comprises: (a) prior to transplantation of an allograft organ into a recipient mammal, administering an anti-CD200 antibody to the recipient mammal; (b) transplanting the allograft organ into the recipient mammal; and (c) administering an anti-CD200 antibody to the recipient mammal following transplantation of the allograft organ.

In some embodiments, the anti-CD200 antibody is subcutaneously or intravenously administered to the recipient mammal. In some embodiments, the anti-CD200 antibody is administered as a single-agent therapy (a monotherapy).

In some embodiments, the methods can include, prior to removal from the donor mammal from which the allograft organ was obtained, administering an anti-CD200 antibody to the donor mammal.

In some embodiments, the allograft is fully MHC mismatched with respect to the recipient mammal. In some embodiments, the recipient mammal is presensitized to the allograft. In some embodiments, the allograft is an ABO-mismatch with respect to the recipient mammal.

In some embodiments, the methods can include administering to the recipient mammal one or more immunosuppressive agents such as any of the immunosuppressive agents described herein. For example, at least one of the one or more immunosuppressive agents is selected from the group consisting of adriamycin, azathioprine, busulfan, cyclophosphamide, fludarabine, 5-fluorouracil, methotrexate, mycophenolate mofetil, mycophenolate sodium, a non-steroidal anti-inflammatory drug, and an IL-2 inhibitor (e.g., an mTOR inhibitor such as rapamycin) or a calcineurin inhibitor such as FK-506 or cyclosporine A).

In some embodiments, two or more immunosuppressive agents are administered to the recipient mammal. In some embodiments, at least two of the two or more immunosuppressive agents are cyclosporine A and cyclophosphamide, FK-506 and cyclophosphamide, or a calcineurin inhibitor (cyclosporine A or FK-506) and a mycophenolate compound (e.g., mycophenolate mofetil or mycophenolate sodium).

In some embodiments, administration of the anti-CD200 antibody allows a shorter duration of treatment with at least one of the one or more immunosuppressive agents, relative to the duration of treatment with the at least one immunosuppressive agent in the absence of the anti-CD200 antibody. In some embodiments, administration of the anti-CD200 antibody allows for a reduced dose level or amount requirement for at least one of the one or more immunosuppressive agents, relative to the dose level or amount of the at least one immunosuppressive agent in the absence of the anti-CD200 antibody.

In some embodiments of any of the methods described herein, the allograft organ is selected from the group consisting of a kidney, a lung, a heart, a pancreas, vascular tissue, a liver or one or more lobes thereof, skin, an eye, gastrointestinal tissue, nervous tissue, muscle tissue, bone or cartilage, bone marrow, connective tissue, red blood cells, islet cells, a cornea, and a lens from an eye. The allograft organ is, in some embodiments, a heart or a kidney.

In some embodiments, the anti-CD200 antibody is administered to the recipient mammal for at least seven (e.g., at least eight, nine, 10, 11, 12, 13, 14, 15, 16, 17, 18, 19, 20, 21, 22, 23, 24, 25, 26, 27, 28, 29, 30, 31) days following transplantation of the allograft into the recipient mammal. In some embodiments, the anti-CD200 antibody is administered at least once per day for up to seven (e.g., up to eight, nine, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) days following transplantation of the allograft into the recipient mammal. In some embodiments, the anti-CD200 antibody is administered at least once per day for at least seven, but less than 30 (e.g., less than 29, 28, 27, 26, 25, 24, 23, 22, 21, 20, 19, 18, 17, 16, 15, 14, 13, 12, 11, 10, 9, or 8) days following transplantation of the allograft into the recipient mammal. In some embodiments of any of the methods described herein, anti-CD200 antibody is administered to the recipient mammal once every two days. In some embodiments of any of the methods described herein, the antibody can be administered at least once a week. In some embodiments of any of the methods described herein, the antibody can be administered at least once every two weeks (e.g., at least once every 12, 13, 14, 15, or 16 days).

In some embodiments of any of the methods described herein, at least one of the one or more immunosuppressive agents is chronically administered to the recipient mammal.

In some embodiments of any of the methods described herein, the anti-CD200 antibody inhibits the interaction between CD200 and CD200 receptor.

In some embodiments of any of the methods described herein, the anti-CD200 antibody comprises a variant heavy chain constant region that has reduced effector function, as compared to the corresponding non-variant form of the heavy chain constant region.

In some embodiments of any of the methods described herein, the anti-CD200 antibody is a whole antibody. In some embodiments of any of the methods described herein, the anti-CD200 antibody is a human antibody, a humanized antibody, a chimeric antibody, a rodent antibody, a deimmunized antibody, or a primatized antibody.

In some embodiments of any of the methods described herein, the anti-CD200 antibody is a CD200-binding fragment of a whole anti-CD200 antibody. The CD200-binding fragment can be one selected from the group consisting of a single-chain antibody, an Fab, an Fab', an F(ab')$_2$, an F(ab')$_3$, an Fv, an Fd, a minibody, a diabody, and a single domain antibody. In some embodiments of any of the methods described herein, the anti-CD200 antibody is samalizumab.

In some embodiments of any of the methods described herein, the recipient mammal is a human and the allograft organ is obtained from a human.

In yet another aspect, the disclosure features a method for prolonging the survival of an allograft organ in a recipient mammal, which method comprises administering to a recipient mammal bearing an allograft organ an anti-CD200 antibody in an amount and with a frequency sufficient to produce and maintain in the recipient mammal the occurrence of a desired immunomodulatory effect and thus prolong the survival of the allograft organ in the recipient mammal.

In another aspect, the disclosure features a method for prolonging the survival of an allograft in a recipient mammal, which method comprises: determining the relative dose amounts of (i) an anti-CD200 antibody effective to produce a desired immunomodulatory effect in a recipient mammal bearing an allograft organ; and administering to the recipient mammal the relative dose amount of the anti-CD200 antibody with a frequency sufficient to maintain in the recipient mammal the desired immunomodulatory effect.

In yet another aspect, the disclosure features a method for prolonging the survival of an allograft organ in a recipient mammal, which method comprises administering to a recipient mammal bearing an allograft organ: (a) an anti-CD200 antibody and (b) one or more immunosuppressive agents, wherein the antibody and one or more immunosuppressive agents are administered in an amount and with a frequency sufficient to produce and maintain in the recipient mammal the occurrence of a desired immunomodulatory effect and thus prolong the survival of the allograft organ in the recipient mammal.

In another aspect, the disclosure features a method for prolonging the survival of an allograft in a recipient mammal, which method comprises: determining the relative dose amounts of (i) an anti-CD200 antibody and (ii) one or more immunosuppressive agents, effective to produce a desired immunomodulatory effect in a recipient mammal bearing an allograft organ; and administering to the recipient mammal the relative dose amounts of the anti-CD200 antibody and one or more immunosuppressive agents with a frequency sufficient to maintain in the recipient mammal the desired immunomodulatory effect.

As detailed in the working examples, the inventors discovered that administration of an anti-CD200 antibody to transplant recipient mammals reduces the expression of SHIP (SH2-containing Inositol 5'-Phosphatase) by splenocytes in the mammals. SHIP is an intracellular phosphatase that, upon stimulation by PI3-kinase, represses the proliferation, survival, and activation of hematopoietic cells. Lioubin et al. (1996) *Mol Cell Biol* 14:5682-5691 and Liu et al. (1997) *J Biol Chem* 272:8983-8988.

SHIP-deficient mice reportedly exhibit an increased number of monocytes and macrophages, their hematopoietic progenitors having enhanced survival, proliferation, and differentiation. In addition, SHIP-deficient mice also fail to acutely reject MHC mismatched bone marrow and are resistant to the development of graft-versus-host disease (GVHD) after allogeneic bone marrow transplantation. Wang et al. (2002) *Science* 295:2094-2097. Furthermore, T cells from SHIP-deficient mice have an enhanced capacity to develop into Tregs. Kerr (2008) *Curr Stem Cell Res Ther* 3(2):99-106.

While the disclosure is not bound by any particular theory or mechanism of action, the inventors believe the therapeutic effect of an anti-CD200 antibody administered to allograft recipient mammals derives, at least in part, from a SHIP-dependent mechanism. That is, administration of an anti-CD200 antibody to an allograft-bearing mammal reduces SHIP expression by immune cells, which in turn results in, among other things, monocytes and macrophages, impaired antigen-specific T cell proliferation, enhanced Treg development, and a more pronounced Th1 cytokine phenotype. Accordingly, in some embodiments, an anti-CD200 antibody, with or without one or more additional immunosuppressive agents, can be administered to an allograft recipient in an amount and with a frequency sufficient to maintain reduced SHIP expression by immune cells in a biological sample obtained from the mammal. That is, the desired immunomodulatory effect can be reduced SHIP expression by a plurality of immune cells (e.g., T cells, B cells, granulocytes, monocytes, and/or macrophages) in a biological sample (e.g., a blood sample or spleen tissue sample) obtained from the mammal. The mechanism, again while not limiting the scope of the disclosure, provides insight as to why inhibiting CD200, an immunosuppressive protein, is useful for prolonging the survival of allografts in recipient mammals.

In some embodiments, the desired immunomodulatory effect is selected from the group consisting of: (i) a decrease in the expression of CD40 by CD11c$^+$CD49b$^-$ cells, relative to the expression level of CD40 by cells of the same histological type in the recipient mammal prior to administration of the anti-CD200 antibody and the one or more immunosuppressive agents; (ii) a decrease in the expression of MHC class II by CD11c$^+$CD49b$^-$ cells, relative to the expression level of MHC class II by cells of the same histological type in the recipient mammal prior to administration of the anti-CD200 antibody and the one or more immunosuppressive agents; (iii) a decrease in the expression of CD80 by CD11c$^+$CD49b$^-$ cells, relative to the expression level of CD80 by cells of the same histological type in the recipient mammal prior to administration of the anti-CD200 antibody and the one or more immunosuppressive agents; (iv) an increase in the expression of IL-12 by CD11c$^+$CD49b$^-$ cells, relative to the expression level of IL-12 by cells of the same histological type in the recipient mammal prior to administration of the anti-CD200 antibody and the one or more immunosuppressive agents; (v) an increase in the concentration of regulatory T cells, relative to the concentration of regulatory T cells of the same histological type in the recipient mammal prior to administration of the anti-CD200 antibody and the one or more immunosuppressive agents; (vi) an increase in the concentration of Gr-1$^+$CD11b$^+$CD45$^+$ cells, relative to the concentration of Gr-1$^+$CD11b$^+$CD45$^+$ cells of the same histological type in the recipient mammal prior to administration of the anti-CD200 antibody and the one or more immunosuppressive agents; (vii) a decrease in the concentration of F4/80$^+$CD45$^+$ cells, relative to the concentration of F4/80$^+$CD45$^+$ cells of the same histological type in the recipient mammal prior to administration of the anti-CD200 antibody and the one or more immunosuppressive agents; (viii) a decrease in the concentration of CD3$^+$CD25$^+$ T cells, relative to the concentration of CD3$^+$CD25$^+$ T cells of the same histological type in the recipient mammal prior to administration of the anti-CD200 antibody and the one or more immunosuppressive agents; (ix) a decrease in the concentration of CD3$^+$CD8$^+$ T cells, relative to the concentration of CD3$^+$CD8$^+$ T cells of the same histological type in the recipient mammal prior to administration of the anti-CD200 antibody and the one or more immunosuppressive agents; (x) an increase in the concentration of CD3$^+$CD200R$^+$ cells, relative to the concentration of CD3$^+$CD200R$^+$ cells of the same histological type in the recipient mammal prior to administration of the anti-CD200 antibody and the one or more immunosuppressive agents; (xi) a decrease in the concentration of CD19$^+$CD45$^+$ cells, relative to the concentration of CD19$^+$CD45$^+$ T cells of the same histological type in the recipient mammal prior to administration of the anti-CD200 antibody and the one or more immunosuppressive agents; and (xii) a decrease in the expression of SHIP by a plurality of immune cells (e.g., T cells, B cells, and/or macrophages) in a biological sample obtained from the recipient mammal. In some embodiments, the regulatory T cells are CD4$^+$CD25$^+$FoxP3$^+$ cells. In some embodiments, the CD11c$^+$CD49b$^-$ cells are antigen presenting cells (e.g., dendritic cells). In some embodiments, the concentration of a particular cell population discussed herein is the concentration of the cell population relative to the total splenocyte population. In some embodiments, a change in at least two of the above biomarkers indicates that a desired immunomodulatory effect occurred in the recipient mammal. In some embodiments, changes in at least three (e.g., at least four, at least five, at least six, at least seven, at least eight, or all) of the biomarkers indicates that an immunomodulatory effect has occurred in the recipient mammal.

In some embodiments, at least a 10 (e.g., at least an 11, 12, 13, 14, 15, 20, 25, 30, 35, 40, 45, 50, 55, 60, 65, 70, or 75 or more) % decrease in the expression of CD40 by CD11c$^+$CD49b$^-$ cells indicates that a desired immunomodulatory effect has occurred in the recipient mammal.

In some embodiments, at least a 10 (e.g., at least an 11, 12, 13, 14, 15, 20, 25, 30, 35, 40, 45, 50, 55, 60, 65, 70, or 75 or more) % decrease in the expression of MHC class II by CD11c$^+$CD49b$^-$ cells indicates that a desired immunomodulatory effect has occurred in the recipient mammal.

In some embodiments, at least a 50 (e.g., at least a 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 or more) % decrease in the expression of CD80 by CD11c$^+$CD49b$^-$ dendritic cells indicates that a desired immunomodulatory effect has occurred in the recipient mammal.

In some embodiments, at least a 50 (e.g., at least a 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 or more) % increase in the expression of IL-12 by CD11c$^+$CD49b$^-$ cells indicates that a desired immunomodulatory effect has occurred in the recipient mammal.

In some embodiments, at least a 50 (e.g., at least a 75, 100, 125, 150, 175, 200, 225, 250, 275, 300, 325, 350, 375, or 400 or more) % increase in the concentration of Gr-1$^+$CD11b$^+$CD45$^+$ cells indicates that a desired immunomodulatory effect has occurred in the recipient mammal.

In some embodiments, at least at least a 50 (e.g., at least a 75, 100, 125, 150, 175, 200, 225, 250, 275, 300, 325, 350, 375, or 400 or more) % increase in the concentration of regulatory T cells indicates that a desired immunomodulatory effect has occurred in the recipient mammal.

In some embodiments, a least a 50 (e.g., at least a 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 or more) % decrease in the concentration of F4/80$^+$CD45$^+$ cells indicates that a desired immunomodulatory effect has occurred in the recipient mammal.

In some embodiments, a least a 50 (e.g., at least a 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 or more) % decrease in the concentration of CD3$^+$CD25$^+$ T cells indicates that a desired immunomodulatory effect has occurred in the recipient mammal.

In some embodiments, at least a 10 (e.g., at least an 11, 12, 13, 14, 15, 20, 25, 30, 35, 40, 45, 50, 55, 60, 65, 70, or 75 or more) % decrease in the concentration of CD3$^+$CD8$^+$ T cells indicates that a desired immunomodulatory effect has occurred in the recipient mammal.

In some embodiments, at least a 5 (e.g., at least a 5, 6, 7, 8, 9, 10, 11, 12, 13, 14, 15, 20, 25, 30, 35, 40, 45, 50, 55, 60, 65, 70, or 75 or more) % increase in the concentration of CD3$^+$CD4$^+$ T cells indicates that a desired immunomodulatory effect has occurred in the recipient mammal.

In some embodiments, at least a 5 (e.g., at least a 5, 6, 7, 8, 9, 10, 11, 12, 13, 14, 15, 20, 25, 30, 35, 40, 45, 50, 55, 60, 65, 70, or 75 or more) % increase in the concentration of CD3$^+$CD200R$^+$ cells indicates that a desired immunomodulatory effect has occurred in the recipient mammal.

In some embodiments, a least a 50 (e.g., at least a 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 or more) % decrease in the concentration of CD19$^+$CD45$^+$ cells indicates that a desired immunomodulatory effect has occurred in the recipient mammal.

In some embodiments, at least a 20 (e.g., at least 25, 30, 35, 40, 45, 50, 55, 60, 65, 70, or 75) % reduction in SHIP expression by a plurality of immune cells (e.g., T cells, B cells, and/or macrophages) indicates that a desired immunomodulatory effect has occurred in the recipient mammal.

In some embodiments, at least one of the one or more immunosuppressive agents is selected from the group consisting of adriamycin, azathioprine, busulfan, cyclophosphamide, cyclosporine A, fludarabine, 5-fluorouracil, methotrexate, mycophenolate mofetil, mycophenolate sodium, a non-steroidal anti-inflammatory drug, rapamycin, and FK-506. For example, at least one of the one or more immunosuppressive agents is cyclosporine A.

In yet another aspect, the disclosure provides an aqueous solution comprising an anti-CD200 antibody at a concentration of at least, or equal to, approximately 10 (e.g., 11, 12, 13, 14, 15, 16, 17, 18, 19, 20, 25, 30, 35, 40, 45, 50, 55, 60, 65, 70, 75, 80, 85, 90, 95, or 100 or more) mg/mL.

In another aspect, the disclosure provides a kit comprising (i) any of the anti-CD200 antibody-containing aqueous solutions described herein; and (ii) a means for delivering the solution to a mammal.

In some embodiments, the means is suitable for subcutaneous or intramuscular delivery of the solution to the mammal. In some embodiments, the means is a syringe or an injection pen.

In some embodiments, the kits can further include one or more immunosuppressive agents for use in prolonging the survival of an allograft organ in a mammal. The agents can be selected from the group consisting of adriamycin, azathioprine, busulfan, cyclophosphamide, cyclosporine A, fludarabine, 5-fluorouracil, methotrexate, mycophenolate mofetil, mycophenolate sodium, a non-steroidal anti-inflammatory drug, rapamycin, and FK-506. In some embodiments, the kits comprise one or both of a calcineurin inhibitor (e.g., cyclosporine A or FK-506) and cyclophosphamide. In some embodiments, the kits contain one or both of a calcineurin inhibitor (e.g., cyclosporine A or FK-506) and a mycophenolate compound. In some embodiments, the kits comprise mycophenolate mofetil, mycophenolate sodium, rapamycin, or FK-506.

In yet another aspect, the disclosure features a kit comprising one or more containers, wherein each container comprises a sterile solution comprising an anti-CD200 antibody at a concentration of at least 10 mg/mL, and wherein each container comprises at least one pharmaceutical unit dosage form of the anti-CD200 antibody. In some embodiments, each container comprises between 0.05 mg to 10 mg of the anti-CD200 antibody. In some embodiments, the kits contain between about 1 mg and 100 mg of the anti-CD200 antibody. In some embodiments, each container has a volume of 0.1 mL to 1 mL, inclusive.

In some embodiments, at least one container comprises an aqueous solution suitable for subcutaneous injection to a mammal or for intramuscular injection to a mammal.

In some embodiments of any of the kits described herein, the anti-CD200 antibody inhibits the interaction between CD200 and CD200 receptor. The anti-CD200 antibody comprises a variant heavy chain constant region that has reduced effector function, as compared to the corresponding non-variant form of the heavy chain constant region. The anti-CD200 antibody can be a whole antibody. In some embodiments, the anti-CD200 antibody is a human antibody, a humanized antibody, a chimeric antibody, a rodent antibody, a deimmunized antibody, or a primatized antibody.

In some embodiments, the anti-CD200 antibody is a CD200-binding fragment of a whole anti-CD200 antibody. For example, the CD200-binding fragment is selected from the group consisting of a single-chain antibody, an Fab, an Fab', an F(ab')$_2$, an F(ab')$_3$, an Fv, an Fd, a minibody, a diabody, and a single domain antibody. In some embodiments, the anti-CD200 antibody is samalizumab.

In another aspect, the disclosure features a pre-filled syringe comprising a sterile solution comprising an anti-CD200 antibody at a concentration of at least 10 mg/mL. In some embodiments, the solution is formulated for subcutaneous administration. In some embodiments, the solution is formulated for intramuscular administration.

In some embodiments, the syringe comprises at least one pharmaceutical unit dosage form of the anti-CD200 antibody in the solution. In some embodiments, the syringe comprises between about 1 mg and 100 mg of the anti-CD200 antibody. In some embodiments, the pharmaceutical unit dosage form has a volume of no more than 1 mL (e.g., no more than 0.5 mL).

In some embodiments of any of the pre-filled syringes described herein, the anti-CD200 antibody inhibits the interaction between CD200 and CD200 receptor. The anti-CD200 antibody may comprise a variant heavy chain constant region that has reduced effector function, as compared to the corresponding non-variant form of the heavy chain constant region. The anti-CD200 antibody can be a whole antibody. In some embodiments, the anti-CD200 antibody is a human antibody, a humanized antibody, a chimeric antibody, a rodent antibody, a deimmunized antibody, or a primatized antibody.

In some embodiments, the anti-CD200 antibody is a CD200-binding fragment of a whole anti-CD200 antibody. For example, the CD200-binding fragment is selected from the group consisting of a single-chain antibody, an Fab, an Fab', an F(ab')$_2$, an F(ab')$_3$, an Fv, an Fd, a minibody, a diabody, and a single domain antibody. In some embodiments, the anti-CD200 antibody is samalizumab.

"Polypeptide," "peptide," and "protein" are used interchangeably and mean any peptide-linked chain of amino acids, regardless of length or post-translational modification. The CD200 proteins described herein can contain or be wild-type proteins or can be variants that have not more than 50 (e.g., not more than one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

The CD200 proteins described herein also include "antigenic peptide fragments" of the proteins, which are shorter than full-length CD200 proteins, but retain at least 10% (e.g., at least 10%, at least 15%, at least 20%, at least 25%, at least 30%, at least 35%, at least 40%, at least 50%, at least 55%, at least 60%, at least 70%, at least 80%, at least 90%, at least 95%, at least 98%, at least 99%, at least 99.5%, or 100% or more) of the ability of the full-length protein to induce an antigenic response in a mammal (see below under "Methods for Producing an Antibody"). Antigenic peptide fragments of a CD200 protein include terminal as well as internal deletion variants of the protein. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. Antigenic peptide fragments can be at least 6 (e.g., at least 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, or 200 or more) amino acid residues in length (e.g., at least 6 contiguous amino acid residues in any one of SEQ ID NOs:1 to 3). In some embodiments, an antigenic peptide fragment of a human CD200 protein is less than 225 (e.g., less than 200, 190, 180, 170, 160, 150, 140, 130, 120, 110, 100, 95, 90, 85, 80, 75, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, or 7) amino acid residues in length (e.g., less than 225 contiguous amino acid residues in any one of SEQ ID NOs:1 to 3). In some embodiments, an antigenic peptide fragment of a full-length CD200 protein is at least 6, but less than 225, amino acid residues in length.

In some embodiments, the human CD200 protein can have an amino acid sequence that is, or is greater than, 70 (e.g., 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100) % identical to the human CD200 protein having the amino acid sequence depicted in SEQ ID NO:1 or SEQ ID NO:2 (see below).

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

Amino acid sequences for exemplary human CD200 proteins as well as antigenic peptide fragments thereof are known in the art and are set forth below.

As used herein, an anti-CD200 antibody includes both whole antibodies and CD200-binding fragments of the whole antibodies. Whole antibodies include different antibody isotypes including IgM, IgG, IgA, IgD, and IgE antibodies. The term "antibody" includes a polyclonal antibody, a monoclonal antibody, a chimerized or chimeric antibody, a humanized antibody, a primatized antibody, a deimmunized human antibody, and a fully human antibody. The antibody can be made in or derived from any of a variety of species, e.g., mammals such as humans, non-human primates (e.g., monkeys, baboons, or chimpanzees), horses, cattle, pigs, sheep, goats, dogs, cats, rabbits, guinea pigs, gerbils, hamsters, rats, and mice. The antibody can be a purified or a recombinant antibody.

As used herein, the term "antibody fragment," "antigen-binding fragment," or similar terms refer to a fragment of an antibody that retains the ability to bind to an antigen (e.g., human CD200 or a fragment thereof as defined herein), e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies are also included in the definition of antibody and are compatible for use in the methods described herein. See, e.g., Todorovska et al. (2001) *J Immunol Methods* 248(1): 47-66; Hudson and Kortt (1999) *J Immunol Methods* 231 (1):177-189; Poljak (1994) *Structure* 2(12):1121-1123; Rondon and Marasco (1997) *Annual Review of Microbiology* 51:257-283, the disclosures of each of which are incorporated herein by reference in their entirety. Bispecific antibodies (including DVD-Ig antibodies; see below) are also embraced by the term "antibody." Bispecific antibodies are monoclonal, preferably human or humanized, antibodies that have binding specificities for at least two different antigens.

CD200-binding fragments of antibodies also include, e.g., single domain antibodies such as camelized single domain antibodies. See, e.g., Muyldermans et al. (2001) *Trends Biochem Sci* 26:230-235; Nuttall et al. (2000) *Curr Pharm Biotech* 1:253-263; Reichmann et al. (1999) *J Immunol Meth* 231:25-38; PCT application publication nos. WO 94/04678 and WO 94/25591; and U.S. Pat. No. 6,005,079, all of which are incorporated herein by reference in their entireties. In some embodiments, the disclosure provides single domain antibodies comprising two VH domains with modifications such that single domain antibodies are formed.

As used herein, the term "chronically" (e.g., to chronically administer a compound), or similar terms, refers to a method of administration in which an agent (e.g., an anti-CD200 antibody described herein and/or an immunosuppressive agent) is administered to a subject (e.g., a transplant patient) in an amount and with a frequency sufficient to maintain an effective amount of the agent in the subject for at least seven (e.g., at least eight, nine, 10, 11, 12, 13, 14, 15, 16, 17, 18, 19, 20, 21, 22, 23, 24) days. In some embodiments, an agent can be chronically administered to a subject for at least one (e.g., at least two, three, four, five, or six) month(s). In some embodiments, an agent can be chronically administered to a subject for a year or more.

Unless otherwise defined, all technical and scientific terms used herein have the same meaning as commonly understood by one of ordinary skill in the art to which this disclosure pertains. In case of conflict, the present document, including definitions, will control. Preferred methods and materials are described below, although methods and materials similar or equivalent to those described herein can also be used in the practice or testing of the presently disclosed methods and compositions. All publications, patent applications, patents, and other references mentioned herein are incorporated by reference in their entirety.

Other features and advantages of the present disclosure, e.g., methods for prolonging the survival of an allograft organ in a recipient mammal, will be apparent from the following description, the examples, and from the claims.

BRIEF DESCRIPTION OF THE DRAWINGS

FIG. 1 depicts the level of CD40 expression by $CD11c^+$ (gated on $CD49b^-$) dendritic cells obtained from mice from each of the groups.

FIG. 2 depicts the level of MHC class II expression by $CD11c^+$ (gated on $CD49b^-$) dendritic cells obtained from mice from each of the groups.

FIG. 3 depicts the level of CD80 expression by $CD11c^+$ (gated on $CD49b^-$) dendritic cells obtained from mice from each of the groups.

FIG. 4 depicts the level of intracellular IL-12 expression by $CD11c^+$ (gated on $CD49b^-$) dendritic cells obtained from mice from each of the groups.

FIG. 5 depicts the percentage of T regulatory $CD4^+CD25^+$ $FoxP3^+$ cells, relative to the total isolated splenocyte population, obtained from mice from each of the groups.

FIG. 6 depicts the percentage of $Gr-1^+CD11b^+CD45^+$ cells, relative to the total isolated splenocyte population, obtained from mice from each of the groups.

FIG. 7 depicts the percentage of $F4/80^+CD45^+$ cells, relative to the total isolated splenocyte population, obtained from mice from each of the groups.

FIG. 8 depicts the percentage of $CD3^+CD25^+$ cells, relative to the total isolated splenocyte population, obtained from mice from each of the groups.

FIG. 9 depicts the percentage of CD3⁺CD8⁺ cells, relative to the total isolated splenocyte population, obtained from mice from each of the groups.

FIG. 10 depicts the percentage of CD3⁺CD4⁺ cells, relative to the total isolated splenocyte population, obtained from mice from each of the groups.

FIG. 11 depicts the percentage of CD3⁺CD200R⁺ cells, relative to the total isolated splenocyte population, obtained from mice from each of the groups.

FIG. 12 depicts the percentage of CD19⁺CD45⁺ cells, relative to the total isolated splenocyte population, obtained from mice from each of the groups.

FIG. 13C depicts SHIP expression by spleen cells of mice that were not immunized with the allogeneic spleen cells. FIG. 13D depicts spleen cells from immunized mice that were not stained with a primary anti-SHIP antibody. Each experimental group represented above included three mice. A representative photograph from each group is provided.

DETAILED DESCRIPTION

The present disclosure provides anti-CD200 antibodies (including CD200-binding fragments of the antibodies), pharmaceutical compositions, and kits, each of which is useful for modulating an immune response in a mammal. As elaborated on in this section, the antibodies (or compositions or kits) can be used alone, or in combination, in methods for prolonging the survival of a graft in a recipient mammal (e.g., a human). While in no way intended to be limiting, suitable applications in which the antibodies, kits, and compositions can be used are set forth in this section and exemplified in the working Examples.

Anti-CD200 Antibodies

Figure 3:
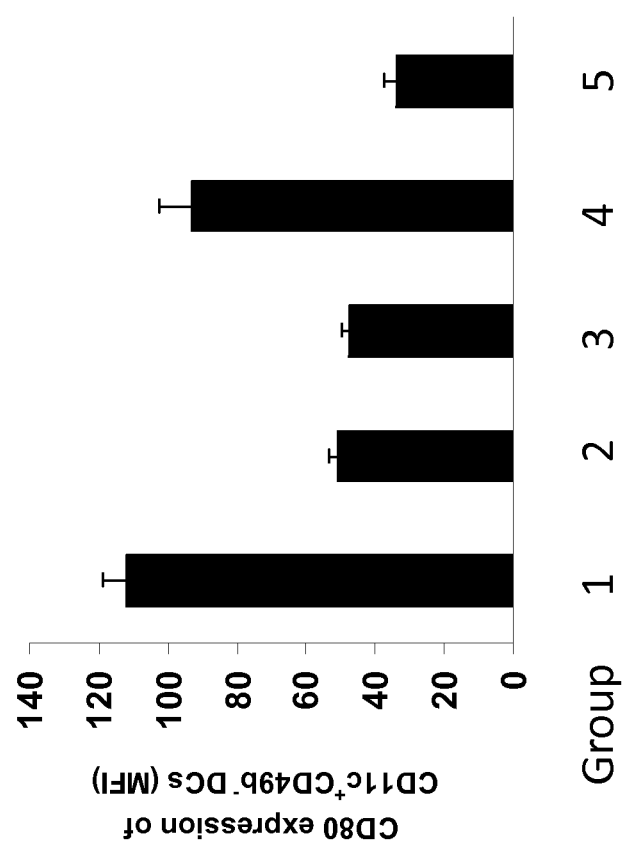

The disclosure features antibodies that bind to a human CD200 polypeptide (sometimes the antibodies are referred to herein as "anti-CD200 antibodies"). Also featured are antigen-binding (CD200-binding) fragments of the antibodies. In some embodiments, an anti-CD200 antibody described herein binds to an extracellular epitope within the human CD200 protein. For example, the anti-CD200 antibody can bind to an extracellular epitope in the human CD200 protein, which protein has the following amino acid sequence:
MERLVIRMPFSHLSTYSLVWVMAAVVLCTAQVQV-VTQDEREQLYTPASLKC SLQNAQEALIVTWQKK-KAVSPENMVTFSENHGVVIQPAYKDKINITQLGLQN STITFWNITLEDEGCYMCLFNTFGFGKISGTACLT-VYVQPIVSLHYKFSEDHLN ITCSATARPAPMVFWK-VPRSGIENSTVTLSHPNGTTSVTSILHIKDPKNQVGKE VICQVLHLGTVTDFKQTVNKGYWFSVPLLLSIVS-LVILLVLISILLYWKRHRNQ DREP (SEQ ID NO:1; GenBank Accession No. NP_005935.2). SEQ ID NO:1 depicts the amino acid sequence for a full-length, precursor human CD200 isoform A protein. In some embodiments, an anti-CD200 antibody described herein binds to an extracellular epitope in the human CD200 protein, which protein has the following amino acid sequence:
MERLTLTRTIGGPLLTATLLGKTTINDYQVIRMPFSHL-STYSLVWVMAAVVLC TAQVQVVTQDEREQLYT-PASLKCSLQNAQEALIVTWQKKKAVSPENMVTFS ENHGVVIQPAYKDKINITQLGLQNSTITFWNITLEDE-GCYMCLFNTFGFGKISG TACLTVYVQPIVSLHYKF-SEDHLNITCSATARPAPMVFWKVPRSGIENSTVTL SHPNGTTSVTSILHIKDPKNQVGKEVICQVLHLGT-VTDFKQTVNKGYWFSVPL LLSIVSLVILLVLISILLY-WKRHRNQDREP (SEQ ID NO:2; GenBank Accession No. NP_001004196.2). SEQ ID NO:2 depicts the amino acid sequence of a full-length CD200 isoform B protein. In some embodiments, the anti-CD200 antibody binds to an extracellular epitope present in a human CD200 protein which protein has the following amino acid sequence:
VIRMPFSHLSTYSLVWVMAAVVLCTAQVQVVTQ-DEREQLYTTASLKCSLQN AQEALIVTWQKKKAVS-PENMVTFSENHGVVIQPAYKDKINITQLGLQNSTITF WNITLEDEGCYMCLFNTFGFGKISGTACLTVYVQ-PIVSLHYKFSEDHLNITCS ATARPAPMVFWKVPRS-GIENSTVTLSHPNGTTSVTSILHIKDPKNQVGKEVIC QVLHLGTVTDFKQTVNKGYWFSVPLLLSIVSLVILLV-LISILLYWKRHRNQDR GELSQGVQKMT (SEQ ID NO:3; GenBank Accession No. CAA28943.1; FIG. 3 of McCaughan et al. (1987) *Immunogenetics* 25:329-335). SEQ ID NO:3 is an exemplary sequence for a full-length human CD200 protein.

In some embodiments, the anti-CD200 antibody can bind to the extracellular portion of an CD200 protein at an epitope within or overlapping with, e.g.: (i) amino acids 1 to 233 of the amino acid sequence depicted in SEQ ID NO:1; (ii) amino acids 1 to 258 of the amino acid sequence depicted in SEQ ID NO:2; or amino acids 1 to 229 of the amino acid sequence depicted in SEQ ID NO:3.

In some embodiments, the anti-CD200 antibody binds to an extracellular epitope within the human CD200 protein lacking the leader sequence. For example, an anti-CD200 antibody described herein can bind to a CD200 protein at an epitope within or overlapping with amino acids 31 to 233 of the amino acid sequence depicted in SEQ ID NO:1, which corresponds to the extracellular portion of the mature form of human CD200 isoform A less the amino terminal leader sequence. In some embodiments, an anti-CD200 antibody described herein can bind to a CD200 protein at an epitope within or overlapping with amino acids 56 to 258 of the amino acid sequence depicted in SEQ ID NO:2, which corresponds to the extracellular portion of the mature form of human CD200 isoform B less the amino terminal leader sequence. In some embodiments, an anti-CD200 antibody described herein can bind to a CD200 protein at an epitope within or overlapping with amino acids 27 to 229 of the amino acid sequence depicted in SEQ ID NO:3, which corresponds to the extracellular portion of the mature form of human CD200 less the amino terminal leader sequence.

An "epitope" refers to the site on a protein (e.g., a human CD200 protein) that is bound by an antibody. "Overlapping epitopes" include at least one (e.g., two, three, four, five, or six) common amino acid residue(s).

In some embodiments, the anti-CD200 antibody specifically binds to a human CD200 protein (e.g., the human CD200 protein having the amino acid sequence depicted in SEQ ID NO:1, SEQ ID NO:2, SEQ ID NO:3, or the extracellular domains of the mature forms of the CD200 proteins). The terms "specific binding" or "specifically binds" refer to two molecules forming a complex (e.g., a complex between an anti-CD200 antibody and a CD200 protein) that is relatively stable under physiologic conditions. Typically, binding is considered specific when the association constant ($K_a$) is higher than $10^6$ M$^{-1}$. Thus, an anti-CD200 antibody can specifically bind to a CD200 protein with a $K_a$ of at least (or greater than) $10^6$ (e.g., at least or greater than $10^7$, $10^8$, $10^9$, $10^{10}$, $10^{11}$ $10^{12}$, $10^{13}$, $10^{14}$, or $10^{15}$ or higher) M$^{-1}$. Examples of antibodies that specifically bind to a human CD200 protein are described in, e.g., U.S. Pat. Nos. 7,408,041; 7,427,665; 7,435,412; and 7,598,353, the disclosures of each of which are incorporated herein by reference in their entirety.

The amino acid sequence for several exemplary anti-CD200 antibodies are described in, e.g., U.S. Pat. No. 7,408,041. For example, the anti-CD200 antibody can comprise the amino acid sequence of the heavy and light chain variable regions of one of the Fab antibodies—d1B10, d1A5, d1B5, c2aB7, c1A10, or c2aA10—depicted in FIG. 23 of U.S. Pat. No. 7,408,041, the sequences depicted in FIG. 23 being incorporated herein by reference in their entirety. In some embodiments, an anti-CD200 antibody described herein contains a paired set of heavy chain CDRs and light chain CDRs of one of the Fab antibodies depicted in FIG. 23 of U.S. Pat. No. 7,408,041. For example, an anti-CD200 antibody described herein contains the paired set of CDRs from the d1B10 Fab antibody: a heavy chain CDR1 (HCDR1) comprising the following sequence: GFTFSGFAMS (SEQ ID NO:4); a heavy chain CDR2 (HCDR2) comprising the following sequence: SISSGGT-TYYLDSVKG (SEQ ID NO:5); a heavy chain CDR3 (HCDR3) comprising the following sequence: GNYYSGT-SYDY (SEQ ID NO:6); a light chain CDR1 (LCDR1) comprising the following sequence: RASESVDSYG-NSFMH (SEQ ID NO:7); a light chain CDR2 (LCDR2) comprising the following sequence: RASNLES (SEQ ID NO:8); and a light chain CDR3 (LCDR3) comprising the following sequence: QQSNEDPRT (SEQ ID NO:9).

In another example, an anti-CD200 antibody described herein can contain the paired set of CDRs from the d1A5 Fab antibody: (i) a HCDR1 comprising the following sequence: GFNIKDYYMH (SEQ ID NO:10); a HCDR2 comprising the following sequence: WIDPENGDTKYAP-KFQG (SEQ ID NO:11); a HCDR3 comprising the following sequence: KNYYVSNYNFFDV (SEQ ID NO:12); a LCDR1 comprising the following sequence: SASSS-VRYMY (SEQ ID NO:13); a LCDR2 comprising the following sequence: DTSKLAS (SEQ ID NO:14); and a LCDR3 comprising the following sequence: FQGSGYPLT (SEQ ID NO:15).

In another example, an anti-CD200 antibody described herein can comprise the paired set of CDRs from the d1B5 Fab antibody: a HCDR1 comprising the following amino acid sequence: GFNIKDYYIH (SEQ ID NO:16); a HCDR2 comprising the following amino acid sequence: WIDPEI-GATKYVPKFQG (SEQ ID NO:17); a HCDR3 comprising the following amino acid sequence: LYGNYDRYYAMDY (SEQ ID NO:18); a LCDR1 comprising the following amino acid sequence: KASQNVRTAVA (SEQ ID NO:19); a LCDR2 comprising the following amino acid sequence: LASNRHT (SEQ ID NO:20); and a LCDR3 comprising the following amino acid sequence: LQHWNYPLT (SEQ ID NO:21).

In another example, an anti-CD200 antibody described herein can contain the paired set of CDRs from the c2aB7 Fab antibody: a HCDR1 comprising the amino acid sequence: GYSFTDYIIL (SEQ ID NO:22); a HCDR2 comprising the amino acid sequence: HIDPYYGSSNYNLK-FKG (SEQ ID NO:23); a HCDR3 comprising the amino acid sequence: SKRDYFDY (SEQ ID NO:24); a LCDR1 comprising the amino acid sequence: KASQDINSYLS (SEQ ID NO:25); a LCDR2 comprising the amino acid sequence: RANRLVD (SEQ ID NO:26); and a LCDR3 comprising the amino acid sequence: LQYDEFPYT (SEQ ID NO:27). Samalizumab contains the aforementioned paired CDR set of the c2aB7 Fab antibody originally set forth in FIG. 23 of U.S. Pat. No. 7,408,041.

In yet another example, an anti-CD200 antibody described herein can contain a paired set of CDRs from the c1A10 Fab antibody: a HCDR1 comprising the amino acid sequence: GYTFTEYTMH (SEQ ID NO:28); a HCDR2 comprising the amino acid sequence: GVNPNNGGALYN-QKFKG (SEQ ID NO:29); a HCDR3 comprising the amino acid sequence: RSNYRYDDAMDY (SEQ ID NO:30); a LCDR1 comprising the amino acid sequence: KSSQSLL-DIDEKTYLN (SEQ ID NO:31); a LCDR2 comprising the amino acid sequence: LVSKLDS (SEQ ID NO:32); and a LCDR3 comprising the amino acid sequence: WQGTHF-PQT (SEQ ID NO:33).

And in yet another example, an anti-CD200 antibody described herein can contain a paired set of CDRs from the c2aA10 Fab antibody: a HCDR1 comprising the amino acid sequence: AFNIKDHYMH (SEQ ID NO:34); a HCDR2 comprising the amino acid sequence: WIDPESGDTEYAP-KFQG (SEQ ID NO:35); a HCDR3 comprising the amino acid sequence: FNGYQALDQ (SEQ ID NO:36); a LCDR1 comprising the amino acid sequence: TASSSVSSSYLH (SEQ ID NO:37); a LCDR2 comprising the amino acid sequence: STSNLAS (SEQ ID NO:38); and a LCDR3 comprising the amino acid sequence: RQYHRSPPIFT (SEQ ID NO:39).

Additional exemplary sets of CDRs of anti-CD200 antibodies are described in, e.g., U.S. Pat. No. 7,427,665. In some embodiments, the anti-CD200 antibody is samalizumab (Alexion Pharmaceuticals, Inc., Cheshire, Conn.).

Methods for determining whether an antibody binds to a protein antigen and/or the affinity for an antibody to a protein antigen are known in the art. For example, the binding of an antibody to a protein antigen can be detected and/or quantified using a variety of techniques such as, but not limited to, Western blot, dot blot, surface plasmon resonance (SPR) method (e.g., BIAcore system; Pharmacia Biosensor AB, Uppsala, Sweden and Piscataway, N.J.), or enzyme-linked immunosorbent assay (ELISA). See, e.g., Harlow and Lane (1988) "Antibodies: A Laboratory Manual" Cold Spring Harbor Laboratory Press, Cold Spring Harbor, N.Y.; Benny K. C. Lo (2004) "Antibody Engineering: Methods and Protocols," Humana Press (ISBN: 1588290921); Borrebaek (1992) "Antibody Engineering, A Practical Guide," W.H. Freeman and Co., NY; Borrebaek (1995) "Antibody Engineering," 2$^{nd}$ Edition, Oxford University Press, NY, Oxford; Johne et al. (1993) *J Immunol Meth* 160:191-198; Jonsson et al. (1993) *Ann Biol Clin* 51:19-26; and Jonsson et al. (1991) *Biotechniques* 11:620-627.

In some embodiments, the anti-CD200 antibody can crossblock binding of another antibody that binds to an epitope within, or overlapping with, a human CD200 protein. In some embodiments, the anti-CD200 antibody can crossblock binding of an antibody that binds to an epitope within, or overlapping with, a peptide fragment of a human CD200 protein. The peptide fragment can be a fragment of a human CD200 protein having the amino acid sequence depicted in, e.g., any one of SEQ ID NOs:1 to 3. As used herein, the term "crossblocking antibody" refers to an antibody that lowers the amount of binding of anti-CD200 antibody to an epitope on a CD200 protein relative to the amount of binding of the anti-CD200 antibody to the epitope in the absence of the antibody. Suitable methods for determining whether a first antibody crossblocks binding of a second antibody to an epitope are known in the art.

Methods for identifying the epitope to which a particular antibody (e.g., an anti-CD200 antibody) binds are also known in the art. For example, the binding epitope of an anti-CD200 antibody can be identified by measuring the binding of the antibody to several (e.g., three, four, five, six, seven, eight, nine, 10, 15, 20, or 30 or more) overlapping peptide fragments of a CD200 protein (e.g., several overlapping fragments of a protein having the amino acid sequence depicted in, e.g., any one of SEQ ID NOs:1 to 3). Each of the different overlapping peptides is then bound to a unique address on a solid support, e.g., separate wells of a multi-well assay plate. Next, the anti-CD200 antibody is interrogated by contacting it to each of the peptides in the assay plate for an amount of time and under conditions that allow for the antibody to bind to its epitope. Unbound anti-CD200 antibody is removed by washing each of the wells. Next, a detectably-labeled secondary antibody that binds to the anti-CD200 antibody, if present in a well of the plate, is contacted to each of the wells, and unbound secondary antibody is removed by washing steps. The presence or amount of the detectable signal produced by the detectably-labeled secondary antibody in a well is an indication that the anti-CD200 antibody binds to the particular peptide fragment associated with the well. See, e.g., Harlow and Lane (supra), Benny K. C. Lo (supra), and U.S. Patent Application Publication No. 20060153836, the disclosure of which is incorporated by reference in its entirety. A particular epitope to which an antibody binds can also be identified using BIAcore chromatographic techniques (see, e.g., Pharmacia BIAtechnology Handbook, "Epitope Mapping," Section 6.3.2, (May 1994); and Johne et al. (1993) *J Immunol Methods* 160:191-8).

In some embodiments, an anti-CD200 antibody, or a CD200-binding fragment thereof, described herein binds to a human CD200 polypeptide expressed on the surface of a cell. Methods for determining whether an antibody binds to a protein expressed on the surface of a cell are known in the art and described in, e.g., Petermann et al. (2007) *J Clin Invest* 117(12):3922-3929; Rijkers et al. (2008) *Mol Immunol* 45(4):1126-35; and Kretz-Rommel (2007) *J Immunol* 178(9):5595-5605.

In some embodiments, an anti-CD200 antibody or CD200-binding fragment thereof described herein inhibits the interaction between CD200 protein and the CD200 receptor. Methods for determining whether an agent (such as an anti-CD200 antibody) inhibits the interaction between CD200 and CD200R are known in the art and described in, e.g., Hatherly and Barclay (2004) *Eur J Immunol* 34(6): 1688-1694. In some embodiments, the antibody inhibits the interaction between CD200 and its receptor by at least 20 (e.g., at least 25, 30, 35, 40, 45, 50, 55, 60, 65, 70, 75, 80, 85, 90, 95, or even 100) % as compared the level of interaction between CD200 and its receptor in the absence of the antibody.

In some embodiments, the anti-CD200 antibody or CD200-binding fragment thereof inhibits the formation of osteoclasts in vitro and/or in vivo. Suitable methods for determining whether an antibody inhibits the formation of osteoclasts are known in the art and described in, e.g., PCT Publication No. WO 08/089,022 and Cui et al. (2007) *Proc Natl Acad Sci USA* 104(36):14436-14441. For example, murine bone marrow cells can be cultured in the presence of, e.g., RANKL and M-CSF in the presence or absence of an anti-CD200 antibody. A decrease in the percentage of osteoclasts formed from the bone marrow cells in the presence of the antibody as compared to the percentage of osteoclasts formed in the absence of the antibody indicates that the antibody inhibits osteoclast formation in vitro.

Since CD200 is expressed on normal cells such as endothelial cells it could be in some embodiments advantageous to administer a variant anti-CD200 antibody (or CD200-binding fragment thereof) with a constant region modified so that it does not mediate, or has decreased ability to mediate, antibody-dependent cell-mediated cytotoxicity (ADCC) or complement-dependent cytotoxicity (CDC). CD200 expression is also upregulated on some activated normal cells (e.g., activated T cells), rendering such cells vulnerable to killing by an anti-CD200 antibody with effector function. It may be advantageous to use an anti-CD200 antibody having diminished, or lacking, effector function to avoid killing of these cells by ADCC or CDC. The effector function of an anti-CD200 antibody can be eliminated by replacing an immunoglobulin constant region that has effector function (e.g., the IgG1 constant domain) for a constant region that does not have effector function (e.g., an IgG2/IgG4 fusion constant region). Additional methods for reducing or eliminating the effector function of an antibody heavy chain constant region are described below.

Methods for Producing an Antibody

Suitable methods for producing an antibody, or antigen-binding fragments thereof, in accordance with the disclosure are known in the art (see, e.g., U.S. Pat. No. 7,408,041 and PCT Application Publication No. WO 09/014,745) and described herein. For example, monoclonal anti-CD200 antibodies may be generated using CD200-expressing cells, a CD200 polypeptide, or an antigenic fragment of CD200 polypeptide, as an immunogen, thus raising an immune response in animals from which antibody-producing cells and in turn monoclonal antibodies may be isolated. The sequence of such antibodies may be determined and the antibodies or variants thereof produced by recombinant techniques. Recombinant techniques may be used to produce chimeric, CDR-grafted, humanized and fully human antibodies based on the sequence of the monoclonal antibodies as well as polypeptides capable of binding to human CD200.

Moreover, antibodies derived from recombinant libraries ("phage antibodies") may be selected using CD200-expressing cells, or polypeptides derived therefrom, as bait to isolate the antibodies or polypeptides on the basis of target specificity. The production and isolation of non-human and chimeric anti-CD200 antibodies are well within the purview of the skilled artisan.

Recombinant DNA technology can be used to modify one or more characteristics of the antibodies produced in non-human cells. Thus, chimeric antibodies can be constructed in order to decrease the immunogenicity thereof in diagnostic or therapeutic applications. Moreover, immunogenicity can be minimized by humanizing the antibodies by CDR grafting and, optionally, framework modification. See, U.S. Pat. Nos. 5,225,539 and 7,393,648, the contents of each of which are incorporated herein by reference.

Antibodies can be obtained from animal serum or, in the case of monoclonal antibodies or fragments thereof, produced in cell culture. Recombinant DNA technology can be used to produce the antibodies according to established procedure, including procedures in bacterial or preferably mammalian cell culture. The selected cell culture system preferably secretes the antibody product.

In another embodiment, a process for the production of an antibody disclosed herein includes culturing a host, e.g., *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic (e.g., bicistronic) DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibers, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane. After one to two weeks, ascitic fluid is taken from the animals.

The foregoing, and other, techniques are discussed in, for example, Kohler and Milstein, (1975) *Nature* 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules are described in the above references and also in, e.g.: WO97/08320; U.S. Pat. No. 5,427,908; U.S. Pat. No. 5,508,717; Smith (1985) *Science* 225:1315-1317; Parmley and Smith (1988) *Gene* 73:305-318; De La Cruz et al. (1988) *J Biol Chem* 263:4318-4322; U.S. Pat. No. 5,403,484; U.S. Pat. No. 5,223,409; WO88/06630; WO92/15679; U.S. Pat. No. 5,780,279; U.S. Pat. No. 5,571,698; U.S. Pat. No. 6,040,136; Davis et al. (1999) *Cancer Metastasis Rev* 18(4):421-5; Taylor et al. (1992) *Nucleic Acids Res* 20: 6287-6295; and Tomizuka et al. (2000) *Proc Natl Acad Sci USA* 97(2): 722-727, the contents of each of which are incorporated herein by reference in their entirety.

The cell culture supernatants are screened for the desired antibodies, preferentially by immunofluorescent staining of CD200-expressing cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g., by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with one or more surface polypeptides derived from a CD200-expressing cell line, or with Protein-A or -G.

Another embodiment provides a process for the preparation of a bacterial cell line secreting antibodies directed against a CD200 protein in a suitable mammal. For example a rabbit is immunized with pooled samples from CD200-expressing tissue or cells or CD200 polypeptide or fragments thereof. A phage display library produced from the immunized rabbit is constructed and panned for the desired antibodies in accordance with methods well known in the art (such as, e.g., the methods disclosed in the various references incorporated herein by reference).

Hybridoma cells secreting the monoclonal antibodies are also disclosed. The preferred hybridoma cells are genetically stable, secrete monoclonal antibodies described herein of the desired specificity, and can be expanded from deep-frozen cultures by thawing and propagation in vitro or as ascites in vivo.

In another embodiment, a process is provided for the preparation of a hybridoma cell line secreting monoclonal antibodies against a CD200 protein. In that process, a suitable mammal, for example a Balb/c mouse, is immunized with one or more polypeptides or antigenic fragments of CD200 or with one or more polypeptides or antigenic fragments derived from a CD200-expressing cell, the CD200-expressing cell itself, or an antigenic carrier containing a purified polypeptide as described. Antibody-producing cells of the immunized mammal are grown briefly in culture or fused with cells of a suitable myeloma cell line. The hybrid cells obtained in the fusion are cloned, and cell clones secreting the desired antibodies are selected. For example, spleen cells of Balb/c mice immunized with a CD200-expressing Chronic Lymphocytic Leukemia (CLL) cell line are fused with cells of the myeloma cell line PAI or the myeloma cell line Sp2/0-Ag 14. The obtained hybrid cells are then screened for secretion of the desired antibodies and positive hybridoma cells are cloned.

Methods for preparing a hybridoma cell line include immunizing Balb/c mice by injecting subcutaneously and/or intraperitoneally an immunogenic composition containing human CD200 protein (or an immunogenic fragment thereof) several times, e.g., four to six times, over several months, e.g., between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described supra, supplemented with a selection medium, for example HAT medium, at regular intervals in order to prevent normal myeloma cells from overgrowing the desired hybridoma cells.

The antibodies and fragments thereof can be "chimeric." Chimeric antibodies and antigen-binding fragments thereof comprise portions from two or more different species (e.g., mouse and human). Chimeric antibodies can be produced with mouse variable regions of desired specificity spliced onto human constant domain gene segments (for example, U.S. Pat. No. 4,816,567). In this manner, non-human antibodies can be modified to make them more suitable for human clinical application (e.g., methods for treating or preventing an immune associated disorder in a human subject).

The monoclonal antibodies of the present disclosure include "humanized" forms of the non-human (e.g., mouse) antibodies. Humanized or CDR-grafted mAbs are particularly useful as therapeutic agents for humans because they are not cleared from the circulation as rapidly as mouse antibodies and do not typically provoke an adverse immune reaction. Methods of preparing humanized antibodies are generally well known in the art. For example, humanization can be essentially performed following the method of Winter and co-workers (see, e.g., Jones et al. (1986) *Nature* 321: 522-525; Riechmann et al. (1988) *Nature* 332:323-327; and Verhoeyen et al. (1988) *Science* 239:1534-1536), by substituting rodent CDRs or CDR sequences for the corresponding sequences of a human antibody. Also see, e.g., Staelens et al. (2006) *Mol Immunol* 43:1243-1257. In some embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production. (See, e.g., Jakobovits et al. (1993) *Proc Natl Acad Sci USA* 90:2551; Jakobovits et al. (1993) *Nature* 362:255-258; Bruggemann et al. (1993) *Year in Immunol* 7:33; and Duchosal et al. (1992) *Nature* 355:258.) Transgenic mice strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein (e.g., a CD200 protein, fragments thereof, or cells expressing CD200 protein) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

In addition, human antibodies can be derived from phage-display libraries (Hoogenboom et al. (1991) *J Mol Biol* 227:381; Marks et al. (1991) *J Mol Biol* 222:581-597; and Vaughan et al. (1996) *Nature Biotech* 14:309 (1996)). Synthetic phage libraries can be created which use randomized combinations of synthetic human antibody V-regions. By selection on antigen fully human antibodies can be made in which the V-regions are very human-like in nature. See, e.g., U.S. Pat. Nos. 6,794,132; 6,680,209; and 4,634,666, and Ostberg et al. (1983) *Hybridoma* 2:361-367, the contents of each of which are incorporated herein by reference in their entirety.

For the generation of human antibodies, also see Mendez et al. (1998) *Nature Genetics* 15:146-156 and Green and Jakobovits (1998) *J Exp Med* 188:483-495, the disclosures of which are hereby incorporated by reference in their entirety. Human antibodies are further discussed and delineated in U.S. Pat. Nos. 5,939,598; 6,673,986; 6,114,598; 6,075,181; 6,162,963; 6,150,584; 6,713,610; and 6,657,103 as well as U.S. Patent Application Publication Nos. 20030229905 A1, 20040010810 A1, 20040093622 A1, 20060040363 A1, 20050054055 A1, 20050076395 A1, and 20050287630 A1. See also International Patent Application Publication Nos. WO 94/02602, WO 96/34096, and WO 98/24893, and European Patent No. EP 0 463 151 B1. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in, e.g., U.S. Pat. Nos. 5,545,807; 5,545,806; 5,625,825; 5,625,126; 5,633,425; 5,661,016; 5,770,429; 5,789,650; 5,814,318; 5,591,669; 5,612,205; 5,721,367; 5,789,215; 5,643,763; 5,569,825; 5,877,397; 6,300,129; 5,874,299; 6,255,458; and 7,041,871, the disclosures of which are hereby incorporated by reference. See also European Patent No. 0 546 073 B1, International Patent Application Publication Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of each of which are hereby incorporated by reference in their entirety. See further Taylor et al. (1992) *Nucleic Acids Res* 20: 6287; Chen et al. (1993) *Int Immunol* 5:647; Tuaillon et al. (1993) *Proc Natl Acad Sci USA* 90: 3720-4; Choi et al. (1993) *Nature Genetics* 4: 117; Lonberg et al. (1994) *Nature* 368: 856-859; Taylor et al. (1994) *Int Immunol* 6: 579-591; Tuaillon et al. (1995) *J Immunol* 154: 6453-65; Fishwild et al. (1996) *Nature Biotechnol* 14: 845; and Tuaillon et al. (2000) *Eur J Immunol* 10: 2998-3005, the disclosures of each of which are hereby incorporated by reference in their entirety.

In certain embodiments, de-immunized anti-CD200 antibodies or antigen-binding fragments thereof are provided. De-immunized antibodies or antigen-binding fragments thereof are antibodies that have been modified so as to render the antibody or antigen-binding fragment thereof non-immunogenic, or less immunogenic, to a given species (e.g., to a human). De-immunization can be achieved by modifying the antibody or antigen-binding fragment thereof utilizing any of a variety of techniques known to those skilled in the art (see, e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art, such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized anti-CD200 antibodies described herein include de-immunized antigen-binding fragments, Fab, Fv, scFv, Fab' and F(ab')$_2$, monoclonal antibodies, murine antibodies, engineered antibodies (such as, for example, chimeric, single chain, CDR-grafted, humanized, and artificially selected antibodies), synthetic antibodies and semi-synthetic antibodies.

In some embodiments, a recombinant DNA comprising an insert coding for a heavy chain variable domain and/or for a light chain variable domain of an anti-CD200 antibody or a CD200 protein-expressing cell line is produced. The term DNA includes coding single stranded DNAs, double stranded DNAs consisting of said coding DNAs and of complementary DNAs thereto, or these complementary (single stranded) DNAs themselves.

Furthermore, a DNA encoding a heavy chain variable domain and/or a light chain variable domain of anti-CD200 antibodies can be enzymatically or chemically synthesized to contain the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted, inserted, or exchanged with one or more other amino acids. Preferably said modification(s) are outside the CDRs of the heavy chain variable domain and/or the CDRs of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain murine variable domain of an anti-CD200 antibody-expressing cell line fused to a human constant domain IgG, for example γ1, γ2, γ3 or γ4, in particular embodiments γ1 or γ4, may be used. Recombinant DNAs including an insert coding for a light chain murine variable domain of an antibody fused to a human constant domain κ or λ, preferably κ, are also provided.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent.

Accordingly, the monoclonal antibodies or antigen-binding fragments of the disclosure can be naked antibodies or antigen-binding fragments that are not conjugated to other agents, for example, a therapeutic agent or detectable label. Alternatively, the monoclonal antibody or antigen-binding fragment can be conjugated to an agent such as, for example, a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an anti-CD200 antibody or antigen-binding fragment (e.g., Fab, Fv, single-chain (scFv), Fab', and F(ab')$_2$) is linked to a molecule that increases the half-life of the antibody or antigen-binding fragment (see above).

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as E. coli gpt (Mulligan and Berg (1981) Proc Natl Acad Sci USA, 78:2072-2076) or Tn5 neo (Southern and Berg (1982) J Mol Appl Genet 1:327-341). The selectable marker gene can be either linked to the DNA gene sequences to be expressed, or introduced into the same cell by co-transfection (Wigler et al. (1979) Cell 16:777-785). A second class of vectors utilizes DNA elements which confer autonomously replicating capabilities to an extrachromosomal plasmid. These vectors can be derived from animal viruses, such as bovine papillomavirus (Sarver et al. (1982) Proc Natl Acad Sci USA, 79:7147-7151), polyoma virus (Deans et al. (1984) Proc Natl Acad Sci USA 81:1292-1296), or SV40 virus (Lusky and Botchan (1981) Nature 293:79-81).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama and Berg (1983) Mol Cell Biol 3:280-289; Cepko et al. (1984) Cell 37:1053-1062; and Kaufman (1985) Proc Natl Acad Sci USA 82:689-693.

As is evident from the disclosure, the anti-CD200 antibodies can be used in therapies (e.g., therapies for an immune associated disorder), including combination therapies.

In the therapeutic embodiments of the present disclosure, bispecific antibodies are contemplated. Bispecific antibodies are monoclonal, preferably human or humanized, antibodies that have binding specificities for at least two different antigens. In the present case, one of the binding specificities is for the human CD200 antigen and the other one is for any other antigen.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello (1983) Nature 305:537-539). Antibody variable domains with the desired binding specificities (antibody-antigen combining sites) can be fused to immunoglobulin constant domain sequences. The fusion preferably is with an immunoglobulin heavy-chain constant domain, including at least part of the hinge, $C_H2$, and $C_H3$ regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, e.g., Suresh et al. (1986) Methods Enzymol 121:210-228; PCT Publication No. WO 96/27011; Brennan et al. (1985) Science 229:81-83; Shalaby et al. J Exp Med (1992) 175:217-225; Kostelny et al. (1992) J Immunol 148(5):1547-1553; Hollinger et al. (1993) Proc Natl Acad Sci USA 90:6444-6448; Gruber et al. (1994) J Immunol 152:5368-5474; and Tutt et al. (1991) J Immunol 147:60-69. Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. See, e.g., Kostelny et al. (1992) J Immunol 148(5):1547-1553. The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al. (1993) Proc Natl Acad Sci USA 90:6444-6448 has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (scFv) dimers has also been reported. See, e.g., Gruber et al. (1994) *J Immunol* 152:5368-5374. Alternatively, the antibodies can be "linear antibodies" as described in, e.g., Zapata et al. (1995) *Protein Eng* 8(10): 1057-1062. Briefly, these antibodies comprise a pair of tandem Fd segments ($V_H$-$C_H$1-$V_H$-$C_H$1) which form a pair of antigen binding regions. Linear antibodies can be bispecific or monospecific.

The disclosure also embraces variant forms of bispecific antibodies such as the tetravalent dual variable domain immunoglobulin (DVD-Ig) molecules described in Wu et al. (2007) *Nat Biotechnol* 25(11):1290-1297. The DVD-Ig molecules are designed such that two different light chain variable domains (VL) from two different parent antibodies are linked in tandem directly or via a short linker by recombinant DNA techniques, followed by the light chain constant domain. Methods for generating DVD-Ig molecules from two parent antibodies are further described in, e.g., PCT Publication Nos. WO 08/024,188 and WO 07/024, 715, the disclosures of each of which are incorporated herein by reference in their entirety.

Effector Functions

The interaction of antibodies and antibody-antigen complexes with cells of the immune system affects a variety of responses, referred to herein as effector functions. Exemplary effector functions include Fc receptor binding, phagocytosis, down-regulation of cell surface receptors (e.g., B cell receptor; BCR), etc. Other effector functions include ADCC, whereby antibodies bind Fc receptors on natural killer (NK) cells or macrophages leading to cell death, and CDC, which is cell death induced via activation of the complement cascade (reviewed in Daeron (1997) *Annu Rev Immunol* 15:203-234; Ward and Ghetie (1995) *Therapeutic Immunol* 2:77-94; and Ravetch and Kinet (1991) *Annu Rev Immunol* 9:457-492). Such effector functions generally require the Fc region to be combined with a binding domain (e.g., an antibody variable domain) and can be assessed using various assays as herein disclosed.

Several antibody effector functions, including ADCC, are mediated by Fc receptors (FcRs), which bind the Fc region of an antibody. In ADCC, NK cells or macrophages bind to the Fc region of the antibody complex and promote lysis of the target cell. The cross-linking of FcRs on NK cells triggers perforin/granzyme-mediated cytotoxicity, whereas in macrophages this cross-linking promotes the release of mediators such as nitric oxide (NO), TNF-α, and reactive oxygen species. For CD200-positive target cells, an anti-CD200 antibody binds to the target cell and the Fc region directs effector function to the target cell. The affinity of an antibody for a particular FcR, and hence the effector activity mediated by the antibody, may be modulated by altering the amino acid sequence and/or post-translational modifications of the Fc and/or constant region of the antibody.

FcRs are defined by their specificity for immunoglobulin isotypes; Fc receptors for IgG antibodies are referred to as FcγR, for IgE as FcεR, for IgA as FcαR and so on. Three subclasses of FcγR have been identified: FcγRI (CD64), FcγRII (CD32) and FcγRIII (CD16). Because each FcγR subclass is encoded by two or three genes, and alternative RNA splicing leads to multiple transcripts, a broad diversity in FcγR isoforms exists. The three genes encoding the FcγRI subclass (FcγRIA, FcγRIB and FcγRIC) are clustered in region 1q21.1 of the long arm of chromosome 1; the genes encoding FcγRII isoforms (FcγRIIA, FcγRIIB and FcγRIIC) and the two genes encoding FcγRIII (FcγRIIIA and FcγRIIIB) are all clustered in region 1q22. These different FcR subtypes are expressed on different cell types (reviewed in Ravetch and Kinet (1991) *Annu Rev Immunol* 9:457-492). For example, in humans, FcγRIIIB is found only on neutrophils, whereas FcγRIIIA is found on macrophages, monocytes, natural killer (NK) cells, and a subpopulation of T-cells. Notably, FcγRIIIA is the only FcR present on NK cells, one of the cell types implicated in ADCC.

FcγRI, FcγRII and FcγRIII are immunoglobulin superfamily (IgSF) receptors; FcγRI has three IgSF domains in its extracellular domain, while FcγRII and FcγRIII have only two IgSF domains in their extracellular domains. Another type of Fc receptor is the neonatal Fc receptor (FcRn). FcRn is structurally similar to major histocompatibility complex (MHC) and consists of an α-chain noncovalently bound to β2-microglobulin.

The binding site on human and murine antibodies for FcγR have been previously mapped to the so-called "lower hinge region" consisting of residues 233-239 (EU index numbering as in Kabat et al. (1991) Sequences of Proteins of Immunological Interest, 5th Ed. Public Health Service, National Institutes of Health, Bethesda, Md.). Woof et al. (1986) *Molec Immunol* 23:319-330; Duncan et al. (1988) *Nature* 332:563; Canfield and Morrison (1991) *J Exp Med* 173:1483-1491; Chappel et al. (1991) *Proc Natl Acad Sci USA* 88:9036-9040. Of residues 233-239, P238 and S239 have been cited as possibly being involved in binding.

Other previously cited areas possibly involved in binding to FcγR are: G316-K338 (human IgG) for human FcγRI (by sequence comparison only; no substitution mutants were evaluated) (Woof et al. (1986) *Molec Immunol* 23:319-330); K274-R301 (human IgG1) for human FcγRIII (based on peptides) (Sarmay et al. (1984) *Molec Immunol* 21:43-51); Y407-R416 (human IgG) for human FcγRIII (based on peptides) (Gergely et al. (1984) *Biochem Soc Trans* 12:739-743 (1984)); as well as N297 and E318 (murine IgG2b) for murine FcγRII (Lund et al. (1992) *Molec Immunol* 29:53-59).

Human effector cells are leukocytes which express one or more FcRs and perform effector functions. In certain embodiments, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils. Effector cells may be isolated from a native source thereof, e.g. from blood or PBMCs.

In CDC, the antibody-antigen complex binds complement, resulting in the activation of the complement cascade and generation of the membrane attack complex. Activation of the classical complement pathway is initiated by the binding of the first component of the complement system (C1q) to antibodies (of the appropriate subclass) which are bound to their cognate antigen; thus the activation of the complement cascade is regulated in part by the binding affinity of the immunoglobulin to C1q protein. C1q and two serine proteases, C1r and C1s, form the complex C1, the first component of the CDC pathway. C1q is a hexavalent molecule with a molecular weight of approximately 460,000 and a structure in which six collagenous "stalks" are connected to six globular head regions. Burton and Woof (1992) *Advances in Immunol* 51:1-84. To activate the complement cascade, it is necessary for C1q to bind to at least two molecules of IgG1, IgG2, or IgG3, but only one molecule of IgM, attached to the antigenic target (Ward and Ghetie (1995) *Therapeutic Immunol* 2:77-94). To assess complement activation, a CDC assay, e.g. as described in Gazzano-Santoro et al. (1996) *J Immunol Methods* 202:163, can be performed.

It has been proposed that various residues of the IgG molecule are involved in binding to C1q including the Glu318, Lys320 and Lys322 residues on the CH2 domain, amino acid residue 331 located on a turn in close proximity to the same beta strand, the Lys235 and Gly237 residues located in the lower hinge region, and residues 231 to 238 located in the N-terminal region of the CH2 domain. See, e.g., Xu et al. (1993) *J Immunol* 150:152 A; PCT publication no. WO 94/29351; Tao et al. (1993) *J Exp Med* 178:661-667; Brekke et al. (1994) *Eur J Immunol* 24:2542-2547; Burton et al. (1980) *Nature* 288:338-344; and U.S. Pat. Nos. 5,648, 260 and 5,624,821. It has further been proposed that the ability of IgG to bind C1q and activate the complement cascade also depends on the presence, absence or modification of the carbohydrate moiety positioned between the two CH2 domains (which is normally anchored at Asn297). See, e.g., Ward and Ghetie (1995) *Therapeutic Immunology* 2:77-94. In certain embodiments, one or more of these residues may be modified, substituted, or removed or one or more amino acid residues may be inserted so as to enhance or decrease CDC activity of the anti-CD200 antibodies provided herein.

Methods for Decreasing or Eliminating Effector Function

Effector functions involving the constant region of the target-specific antibody may be modulated by altering properties of the constant or Fc region. Altered effector functions include, for example, a modulation in one or more of the following activities: ADCC, CDC, apoptosis, binding to one or more Fc-receptors, and pro-inflammatory responses. Modulation refers to an increase, decrease, or elimination of an effector function activity exhibited by a subject antibody as compared to the activity of a second antibody. In certain embodiments, the second antibody is an antibody possessing a naturally-occurring effector function that has not been modified. In particular embodiments, modulation includes situations in which an activity is abolished or completely absent. Further, in some instances, a non-variant antibody may exhibit effector function activity similar or equivalent to the activity of the chC2aB7-hG1 or the hB7V3V2-hG1 antibodies disclosed herein.

A variant constant region with altered FcR binding affinity and/or ADCC activity and/or altered CDC activity is a polypeptide which has either enhanced or diminished FcR binding activity and/or ADCC activity and/or CDC activity compared to the native or parent polypeptide or to a polypeptide comprising a native sequence or constant region. A polypeptide variant which displays increased binding to an FcR binds at least one FcR with greater affinity than the parent polypeptide. A polypeptide variant which displays decreased binding to an FcR binds at least one FcR with lower affinity than a parent polypeptide. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, a variant anti-CD200 antibody that displays altered ADCC and/or CDC activity may exhibit either increased or reduced ADCC and/or CDC activity compared to the native or parent polypeptide. For example, in some embodiments, the anti-CD200 antibody comprising a variant constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the native form of the constant region. An anti-CD200 antibody comprising a variant constant region displaying reduced ADCC and/or CDC may exhibit reduced or no ADCC and/or CDC activity as exemplified herein.

A native sequence Fc or constant region comprises an amino acid sequence identical to the amino acid sequence of an Fc or constant chain region found in nature. A variant or altered Fc or constant region comprises an amino acid sequence which differs from that of a native sequence heavy chain region by virtue of at least one amino acid modification, insertion, or deletion, for example. In certain embodiments, the variant or altered constant region has at least one amino acid substitution, insertion, and/or deletion, compared to a native sequence constant region or to the constant region of a parent polypeptide, e.g. from about one to about one hundred amino acid substitutions, insertions, and/or deletions in a native sequence constant region or in the constant region of the parent polypeptide. In some embodiments, the variant or altered constant region herein will possess at least about 70% homology (similarity) or identity with a native sequence constant region and/or with a constant region of a parent polypeptide, and in some instances at least about 75% and in other instances at least about 80% homology or identity therewith, and in other embodiments at least about 85%, 90% or 95% homology or identity therewith. The variant or altered constant region may also contain one or more amino acid deletions or insertions. Additionally, the variant constant region may contain one or more amino acid substitutions, deletions, or insertions that results in altered post-translational modifications, including, for example, an altered glycosylation pattern.

Antibodies or antigen-binding fragments thereof with altered or no effector functions may be generated by engineering or producing antibodies with variant constant, Fc, or heavy chain regions; recombinant DNA technology and/or cell culture and expression conditions may be used to produce antibodies with altered function and/or activity. For example, recombinant DNA technology may be used to engineer one or more amino acid substitutions, deletions, or insertions in regions (such as, for example, Fc or constant regions) that affect antibody function including effector functions. Alternatively, changes in post-translational modifications, such as, e.g., glycosylation patterns, may be achieved by manipulating the cell culture and expression conditions by which the antibody is produced. Suitable methods for introducing one or more substitutions, additions, or deletions into an Fc region of an antibody are well known in the art and include, e.g., standard DNA mutagenesis techniques as described in, e.g., Sambrook et al. (1989) "Molecular Cloning: A Laboratory Manual, $2^{nd}$ Edition," Cold Spring Harbor Laboratory Press, Cold Spring Harbor, N.Y.; Harlow and Lane (1988), supra; Borrebaek (1992), supra; Johne et al. (1993), supra; PCT publication no. WO 06/53301; and U.S. Pat. No. 7,704,497.

Accordingly, certain aspects and methods of the present disclosure relate to anti-CD200 antibodies with altered effector functions that comprise one or more amino acid substitutions, insertions, and/or deletions. In some embodiments, such a variant anti-CD200 antibody exhibits reduced or no effector function. In some embodiments, a variant antibody comprises a hybrid constant region, or a portion thereof, such as a G2/G4 hybrid constant region (see e.g., Burton et al. (1992) *Adv Immun* 51:1-18; Canfield et al.

(1991) *J Exp Med* 173:1483-1491; and Mueller et al. (1997) *Mol Immunol* 34(6):441-452). For example (and in accordance with Kabat numbering), the IgG1 and IgG4 constant regions contain $G_{249}G_{250}$ residues whereas the IgG2 constant region does not contain residue 249, but does contain $G_{250}$. In a G2/G4 hybrid constant region, where the 249-250 region comes from the G2 sequence, the constant region can be further modified to introduce a glycine residue at position 249 to produce a G2/G4 fusion having $G_{249}/G_{250}$.

In addition to using a G2/G4 construct as described above, anti-CD200 antibodies with reduced effector function may be produced by introducing other types of changes in the amino acid sequence of certain regions of the antibody. Such amino acid sequence changes include but are not limited to the Ala-Ala mutation described in, e.g., PCT Publication nos. WO 94/28027 and WO 98/47531; and Xu et al. (2000) *Cell Immunol* 200:16-26. Thus, in some embodiments, anti-CD200 antibodies with mutations within the constant region including the Ala-Ala mutation may be used to reduce or abolish effector function. According to these embodiments, the constant region of an anti-CD200 antibody comprises a mutation to an alanine at position 234 or a mutation to an alanine at position 235. Additionally, the constant region may contain a double mutation: a mutation to an alanine at position 234 and a second mutation to an alanine at position 235. In one embodiment, the anti-CD200 antibody comprises an IgG4 framework, wherein the Ala-Ala mutation would describe a mutation(s) from phenylalanine to alanine at position 234 and/or a mutation from leucine to alanine at position 235. In another embodiment, the anti-CD200 antibody comprises an IgG1 framework, wherein the Ala-Ala mutation would describe a mutation(s) from leucine to alanine at position 234 and/or a mutation from leucine to alanine at position 235. An anti-CD200 antibody may alternatively or additionally carry other mutations, including the point mutation K322A in the CH2 domain (Hezareh et al. (2001) *J Virol* 75:12161-8). An antibody with said mutation(s) in the constant region may furthermore be a blocking or non-blocking antibody.

Additional substitutions that, when introduced into a heavy chain constant region, result in decreased effector function are set forth in, e.g., Shields et al. (2001) *J Biol Chem* 276(9):6591-6604. See particularly Table 1 ("Binding of human IgG1 variants to human FcRn and FcγR) of Shields et al., the disclosure of which is incorporated herein by reference in its entirety. By screening a library of anti-IgE antibodies, each antibody of the library differing by one or more substitutions in the heavy chain constant region, for binding to a panel of Fc receptors (including FcRn, FcγRI, FcγRIIA, FcγRIIB, and FcγRIIIA), the authors identified a number of substitutions that modulate specific Fc-Fc receptor interactions. For example, a variant IgG2a heavy chain constant region in which the CH2 domain contains a D265A substitution (heavy chain amino acid numbering according to Kabat et al. (supra)) results in a complete loss of interaction between the variant constant region and IgG Fc receptors FcγRIIB, FcγRIII, FcγRI, and FcγRIV. Shields et al. (2001) at page 6595, Table 1. See also Baudino et al. (2008) *J Immunol* 181:6664-6669 (supra).

Changes within the hinge region also affect effector functions. For example, deletion of the hinge region may reduce affinity for Fc receptors and may reduce complement activation (Klein et al. (1981) *Proc Natl Acad Sci USA* 78: 524-528). The present disclosure therefore also relates to antibodies with alterations in the hinge region.

In some embodiments, anti-CD200 antibodies may be modified to either enhance or inhibit complement dependent cytotoxicity (CDC). Modulated CDC activity may be achieved by introducing one or more amino acid substitutions, insertions, or deletions in an Fc region of the antibody. See, e.g., U.S. Pat. No. 6,194,551. Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See, e.g., Caron et al. (1992) *J Exp Med* 176:1191-1195 and Shopes (1992) *Immunol* 148:2918-2922; PCT publication nos. WO 99/51642 and WO 94/29351; Duncan and Winter (1988) *Nature* 322:738-40; and U.S. Pat. Nos. 5,648,260 and 5,624,821. Homodimeric antibodies with enhanced anti-tumor activity may also be prepared using heterobifunctional cross-linkers as described in Wolff et al. (1993) *Cancer Research* 53:2560-2565. Alternatively, an antibody can be engineered which has dual Fc regions and may thereby have enhanced complement lysis and ADCC capabilities. See, e.g., Stevenson et al. (1989) *Anti-Cancer Drug Design* 3:219-230.

Another potential means of modulating effector function of antibodies includes changes in glycosylation, which is summarized in, e.g., Raju (2003) *BioProcess International* 1(4):44-53. According to Wright and Morrison, the microheterogeneity of human IgG oligosaccharides can affect biological functions such as CDC and ADCC, binding to various Fc receptors, and binding to C1q protein. (1997) *TIBTECH* 15:26-32. Glycosylation patterns of antibodies can differ depending on the producing cell and the cell culture conditions (Raju, supra). Such differences can lead to changes in both effector function and pharmacokinetics. See, e.g., Israel et al. (1996) *Immunology* 89(4):573-578; Newkirk et al. (1996) *Clin Exp Immunol* 106(2):259-264. Differences in effector function may be related to the IgG's ability to bind to the Fcγ receptors (FcγRs) on the effector cells. Shields et al. have shown that IgG, with variants in amino acid sequence that have improved binding to FcγR, can exhibit up to 100% enhanced ADCC using human effector cells. (2001) *J Biol Chem* 276(9):6591-6604. While these variants include changes in amino acids not found at the binding interface, both the nature of the sugar component as well as its structural pattern may also contribute to the differences observed. In addition, the presence or absence of fucose in the oligosaccharide component of an IgG can improve binding and ADCC. See, e.g., Shields et al. (2002) *J Biol Chem* 277(30):26733-26740. An IgG that lacked a fucosylated carbohydrate linked to $Asn^{297}$ exhibited normal receptor binding to the FcγRI receptor. In contrast, binding to the FcγRIIIA receptor was improved 50-fold and accompanied by enhanced ADCC, especially at lower antibody concentrations.

Shinkawa et al. demonstrated that an antibody to the human IL-5 receptor produced in a rat hybridoma showed more than 50% higher ADCC when compared to the antibody produced in Chinese hamster ovary cells (CHO) (Shinkawa et al. (2003) *J Biol Chem* 278(5):3466-73). Monosaccharide composition and oligosaccharide profiling showed that the rat hybridoma-produced IgG had a lower content of fucose than the CHO-produced protein. The authors concluded that the lack of fucosylation of an IgG1 has a critical role in enhancement of ADCC activity.

A different approach was taken by Umana et al. who changed the glycosylation pattern of chCE7, a chimeric IgG1 anti-neuroblastoma antibody. ((1999) *Nat Biotechnol* 17(2):176-180). Using tetracycline, they regulated the activity of a glycosyltransferase enzyme (GnTIII) which bisects oligosaccharides that have been implicated in ADCC activity. The ADCC activity of the parent antibody was barely above background level. Measurement of ADCC activity of the chCE7 produced at different tetracycline levels showed an optimal range of GnTIII expression for maximal chCE7 in vitro ADCC activity. This activity correlated with the level of constant region-associated, bisected complex oligosaccharide. Newly optimized variants exhibited substantial ADCC activity. Similarly, Wright and Morrison produced antibodies in a CHO cell line deficient in glycosylation and showed that antibodies produced in this cell line were incapable of complement-mediated cytolysis. (1994) *J Exp Med* 180:1087-1096. Thus, as known alterations that affect effector function include modifications in the glycosylation pattern or a change in the number of glycosylated residues, the present disclosure relates to a CD200 antibody wherein glycosylation is altered to either enhance or decrease effector function(s) including ADCC and CDC. Altered glycosylation includes a decrease or increase in the number of glycosylated residues as well as a change in the pattern or location of glycosylated residues.

Still other approaches exist for altering the effector function of antibodies. For example, antibody-producing cells can be hypermutagenic, thereby generating antibodies with randomly altered polypeptide residues throughout an entire antibody molecule. See, e.g., PCT publication no. WO 05/011735. Hypermutagenic host cells include cells deficient in DNA mismatch repair. Antibodies produced in this manner may be less antigenic and/or have beneficial pharmacokinetic properties. Additionally, such antibodies may be selected for properties such as enhanced or decreased effector function(s).

It is further understood that effector function may vary according to the binding affinity of the antibody. For example, antibodies with high affinity may be more efficient in activating the complement system compared to antibodies with relatively lower affinity (Marzocchi-Machado et al. (1999) *Immunol Invest* 28:89-101). Accordingly, an antibody may be altered such that the binding affinity for its antigen is reduced (e.g., by changing the variable regions of the antibody by methods such as substitution, addition, or deletion of one or more amino acid residues). An anti-CD200 antibody with reduced binding affinity may exhibit reduced effector functions, including, for example, reduced ADCC and/or CDC.

Antibody Conjugates

The antibodies described herein can be modified, e.g., prior to expression or following their expression or purification. The modifications can be covalent or non-covalent modifications. Such modifications can be introduced into the antibodies by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies.

In some embodiments, the antibodies can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, or a luminescent label. Suitable heterologous polypeptides include, e.g., an antigenic tag (e.g., FLAG, polyhistidine, hemagglutinin (HA), glutathione-S-transferase (GST), or maltose-binding protein (MBP)) for use in purifying the antibodies. Heterologous polypeptides also include polypeptides that are useful as diagnostic or detectable markers, for example, luciferase, green fluorescent protein (GFP), or chloramphenicol acetyl transferase (CAT). Where the heterologous moiety is a polypeptide, the moiety can be incorporated into an antibody described herein as a fusion protein.

Suitable radioactive labels include, e.g., $^{32}P$, $^{33}P$, $^{14}C$, $^{125}I$, $^{131}I$, $^{35}S$, and $^3H$. Suitable fluorescent labels include, without limitation, fluorescein, fluorescein isothiocyanate (FITC), green fluorescence protein (GFP), DyLight 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}I$ in meta-[$^{125}I$]iodophenyl-N-hydroxysuccinimide ([$^{125}I$]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an anti-CD200 antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodiments, the fluorophores can be conjugated to a heterobifunctional cross-linker moiety such as sulfo-SMCC.

Suitable conjugation methods involve incubating an antibody protein with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the antibodies can be modified, e.g., with a moiety that improves the stabilization and/or retention of the antibodies in circulation, e.g., in blood, serum, or other tissues. For example, an anti-CD200 antibody can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476. The stabilization moiety can improve the stability, or retention of, the antibody by at least 1.5 (e.g., at least 2, 5, 10, 15, 20, 25, 30, 40, or 50 or more) fold.

In some embodiments, the antibodies described herein can be glycosylated. In some embodiments, an antibody described herein can be subjected to enzymatic or chemical treatment, or produced from a cell, such that the antibody has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361.

Pharmaceutical Compositions and Formulations

The compositions containing an anti-CD200 antibody can be formulated as a pharmaceutical composition, e.g., for administration to a recipient mammal to prolong the survival of an allograft organ. The pharmaceutical compositions will generally include a pharmaceutically acceptable carrier. As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt. See, e.g., Berge et al. (1977) *J Pharm Sci* 66:1-19.

The compositions can be formulated according to standard methods. Pharmaceutical formulation is a well-established art, and is further described in, e.g., Gennaro (2000) "Remington: The Science and Practice of Pharmacy," 20$^{th}$ Edition, Lippincott, Williams & Wilkins (ISBN: 0683306472); Ansel et al. (1999) "Pharmaceutical Dosage Forms and Drug Delivery Systems," 7$^{th}$ Edition, Lippincott Williams & Wilkins Publishers (ISBN: 0683305727); and Kibbe (2000) "Handbook of Pharmaceutical Excipients American Pharmaceutical Association," 3$^{rd}$ Edition (ISBN: 091733096X). In some embodiments, a composition can be formulated, for example, as a buffered solution at a suitable concentration and suitable for storage at 2-8° C. In some embodiments, a composition can be formulated for storage at a temperature below 0° C. (e.g., −20° C. or −80° C.).

The pharmaceutical compositions can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application. For example, compositions containing an anti-CD200 antibody intended for systemic or local delivery can be in the form of injectable or infusible solutions. Accordingly, the compositions can be formulated for administration by a parenteral mode (e.g., intravenous, subcutaneous, intraperitoneal, or intramuscular injection).

"Parenteral administration," "administered parenterally," and other grammatically equivalent phrases, as used herein, refer to modes of administration other than enteral and topical administration, usually by injection, and include, without limitation, intravenous, intranasal, intraocular, pulmonary, intramuscular, intraarterial, intrathecal, intracapsular, intraorbital, intracardiac, intradermal, intrapulmonary, intraperitoneal, transtracheal, subcutaneous, subcuticular, intraarticular, subcapsular, subarachnoid, intraspinal, epidural, intracerebral, intracranial, intracarotid and intrasternal injection and infusion (see below).

The compositions can be formulated as a solution, microemulsion, dispersion, liposome, or other ordered structure suitable for stable storage at high concentration. Sterile injectable solutions can be prepared by incorporating an antibody described herein in the required amount in an appropriate solvent with one or a combination of ingredients enumerated above, as required, followed by filtered sterilization. Generally, dispersions are prepared by incorporating an anti-CD200 antibody described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of the antibody described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts and gelatin.

In certain embodiments, the anti-CD200 antibody can be prepared with a carrier that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) "Sustained and Controlled Release Drug Delivery Systems," Marcel Dekker, Inc., New York.

In some embodiments, an anti-CD200 antibody described herein can be modified, e.g., with a moiety that improves its stabilization and/or retention in circulation, e.g., in blood, serum, or other tissues. The stabilization moiety can improve the stability, or retention of, the antibody by at least 1.5 (e.g., at least 2, 5, 10, 15, 20, 25, 30, 40, or 50 or more) fold.

In some embodiments, an anti-CD200 antibody is present in unit dosage form, which can be particularly suitable for self-administration. A formulated product of the present disclosure can be included within a container, typically, for example, a vial, cartridge, prefilled syringe or disposable pen. A doser such as the doser device described in U.S. Pat. No. 6,302,855 may also be used, for example, with an injection system of the present disclosure.

An injection system of the present disclosure may employ a delivery pen as described in U.S. Pat. No. 5,308,341. Pen devices, most commonly used for self-delivery of insulin to patients with diabetes, are well known in the art. Such devices can comprise at least one injection needle (e.g., a 31 gauge needle of about 5 to 8 mm in length), are typically pre-filled with one or more therapeutic unit doses of a therapeutic solution, and are useful for rapidly delivering the solution to a subject with as little pain as possible.

One medication delivery pen includes a vial holder into which a vial of insulin or other medication may be received. The vial holder is an elongate generally tubular structure with proximal and distal ends. The distal end of the vial holder includes mounting means for engaging a double-ended needle cannula. The proximal end also includes mounting means for engaging a pen body which includes a driver and dose setting apparatus. A disposable medication (e.g., anti-CD200 antibody) containing vial for use with the prior art vial holder includes a distal end having a pierceable elastomeric septum that can be pierced by one end of a double-ended needle cannula. The proximal end of this vial includes a stopper slidably disposed in fluid tight engagement with the cylindrical wall of the vial. This medication delivery pen is used by inserting the vial of medication into the vial holder. A pen body then is connected to the proximal end of the vial holder. The pen body includes a dose setting apparatus for designating a dose of medication to be delivered by the pen and a driving apparatus for urging the stopper of the vial distally for a distance corresponding to the selected dose. The user of the pen mounts a double-ended needle cannula to the distal end of the vial holder such that the proximal point of the needle cannula pierces the septum on the vial. The patient then selects a dose and operates the pen to urge the stopper distally to deliver the selected dose. The dose selecting apparatus returns to zero upon injection of the selected dose. The patient then removes and discards the needle cannula, and keeps the prior art medication delivery pen in a convenient location for the next required medication administration. The medication in the vial will become exhausted after several such administrations of medication. The patient then separates the vial holder from the pen body. The empty vial may then be removed and discarded. A new vial can be inserted into the vial holder, and the vial holder and pen body can be reassembled and used as explained above. Accordingly, a medication delivery pen generally has a drive mechanism for accurate dosing and ease of use.

A dosage mechanism such as a rotatable knob allows the user to accurately adjust the amount of medication that will be injected by the pen from a prepackaged vial of medication. To inject the dose of medication, the user inserts the needle under the skin and depresses the knob once as far as it will depress. The pen may be an entirely mechanical device or it may be combined with electronic circuitry to accurately set and/or indicate the dosage of medication that is injected into the user. See U.S. Pat. No. 6,192,891.

In some embodiments, the needle of the pen device is disposable and the kits include one or more disposable replacement needles. Pen devices suitable for delivery of the any one of the presently featured antibody solutions are also described in, e.g., U.S. Pat. Nos. 6,277,099; 6,200,296; and 6,146,361, the disclosures of each of which are incorporated herein by reference in their entirety. A microneedle-based pen device is described in, e.g., U.S. Pat. No. 7,556,615, the disclosure of which is incorporated herein by reference in its entirety. See also the Precision Pen Injector (PPI) device, Molly™, manufactured by Scandinavian Health Ltd.

The present disclosure also presents controlled-release or extended-release formulations suitable for chronic and/or self-administration of a medication. The various formulations can be administered to a patient in need of treatment (e.g., a recipient of an allograft) with the medication (e.g., an antibody of the present disclosure and at least one immunosuppressive agent) by intravenous administration as a bolus or by continuous infusion over a period of time.

In some embodiments, an anti-CD200 antibody is formulated for sustained-release, extended-release, timed-release, controlled-release, or continuous-release administration. In some embodiments, depot formulations are used to administer the antibody to the subject in need thereof. In this method, the antibody is formulated with one or more carriers providing a gradual release of active agent over a period of a number of hours or days. Such formulations are often based upon a degrading matrix which gradually disperses in the body to release the active agent.

One formulation suitable for depot injection of an anti-CD200 antibody relies upon a polymeric depot system. The polymer can be a biodegradable polymer such as poly(lactic acid) (PLA) and/or poly(lactic-co-glycolic acid) (PLGA) and may be in the form of a solution in a solvent, a pre-polymer mixed with an initiator, encapsulated polymer particles or polymer microspheres. The polymer or polymer particles entrap the active agent and are gradually degraded releasing the agent by slow diffusion and/or as the matrix is absorbed. Examples of such systems include those described in U.S. Pat. Nos. 4,938,763; 5,480,656; and 6,113,943, and can result in delivery of active agents over a period of up to several months.

Another depot system was set forth in U.S. Pat. No. 5,807,573, which system is lipid-based—a diacylglycerol, a phospholipid and optionally water, glycerol, ethylene glycol or propylene glycol. Suitable depot formulations are also described in, e.g., U.S. patent application publication no. 20060165800 (describing an injectable depot gel composition for systemic and local delivery of a beneficial agent to a subject over a short duration of time); Bari et al. (2010) *Int J Pharm Sci Rev Res* 3(1):1-10 (describing prolonged release formulations suitable for parenteral delivery of a therapeutic protein into a mammal); and U.S. patent application publication no. 20090010928, which describes depot antibody formulations, including, e.g., a composition comprising monoclonal antibody at 5 mg/mL, formulated in aqueous buffer consisting of 50 mM L-histidine, 150 mM NaCl, adjusted to pH 6.0 with HCl.

Anti-CD200 antibody compositions can be prepared in dosage unit form for ease of administration and uniformity of dosage. "Dosage unit form," as used herein refers to physically discrete units suited as unitary dosages for the subject to be treated; each unit containing a predetermined quantity of active compound calculated to produce the desired therapeutic effect in association with the selected pharmaceutical carrier.

The disclosure provides aqueous solutions comprising an antibody (such as samalizumab) that binds to CD200. In some embodiments, the solutions can be high concentration solutions of an anti-CD200 antibody. Such solutions are sometimes referred to herein as "high concentration antibody solutions." As used herein, a "high concentration" of an anti-CD200 antibody in an aqueous solution is a concentration of the antibody that is at least, equal to, or greater than, 10 (e.g., at least, equal to, or greater than, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, or 250) mg/mL. In some embodiments, the anti-CD200 antibody is present in the solution at a concentration of more than 200 (e.g., more than 200, 205, 210, 215, 220, 225, 230, 235, 240, 245, 250, 255, 260, 265, 270, 275, 280, 285, or 290) mg/mL. In some embodiments, the antibody is present in the solution at a concentration of, e.g., 10 mg/mL to 200 mg/mL, 20 mg/mL to 200 mg/mL, 30 mg/mL to 200 mg/mL, 40 mg/mL to 200 mg/mL, 50 mg/mL to 200 mg/mL, 60 mg/mL to 200 mg/mL, 70 mg/mL to 200 mg/mL, 80 mg/mL to 200 mg/mL, 90 mg/mL to 200 mg/mL, 100 mg/mL to 200 mg/mL, 110 mg/mL to 200 mg/mL, 120 mg/mL to 200 mg/mL, 130 mg/mL to 200 mg/mL, 140 mg/mL to 200 mg/mL, 150 mg/mL to 200 mg/mL, 10 mg/mL to 100 mg/mL, 20 mg/mL to 100 mg/mL, 30 mg/mL to 100 mg/mL, 40 mg/mL to 100 mg/mL, 50 mg/mL to 100 mg/mL, 60 mg/mL to 100 mg/mL, 70 mg/mL to 100 mg/mL, 80 mg/mL to 100 mg/mL, 90 mg/mL to 100 mg/mL, 10 mg/mL to 150 mg/mL, 20 mg/mL to 150 mg/mL, 30 mg/mL to 150 mg/mL, 40 mg/mL to 150 mg/mL, 50 mg/mL to 150 mg/mL, 60 mg/mL to 150 mg/mL, 70 mg/mL to 150 mg/mL, 80 mg/mL to 150 mg/mL, 90 mg/mL to 150 mg/mL, 100 mg/mL to 150 mg/mL, 110 mg/mL to 150 mg/mL, 120 mg/mL to 150 mg/mL, 40 mg/mL to 50 mg/mL, 10 mg/mL to 250 mg/mL, 20 mg/mL to 250 mg/mL, 30 mg/mL to 250 mg/mL, 40 mg/mL to 250 mg/mL, 50 mg/mL to 250 mg/mL, 60 mg/mL to 250 mg/mL, 70 mg/mL to 250 mg/mL, 80 mg/mL to 250 mg/mL, 90 mg/mL to 250 mg/mL, 100 mg/mL to 250 mg/mL, 110 mg/mL to 250 mg/mL, 120 mg/mL to 250 mg/mL, 130 mg/mL to 250 mg/mL, 140 mg/mL to 250 mg/mL, 150 mg/mL to 250 mg/mL, 160 mg/mL to 250 mg/mL, 170 mg/mL to 250 mg/mL, 180 mg/mL to 250 mg/mL, 190 mg/mL to 250 mg/mL, 200 mg/mL to 250 mg/mL, greater than 200 mg/mL (e.g., at least 201 mg/mL) to 250 mg/mL, or greater than 200 mg/mL (e.g., 201 mg/mL or greater) to 300 mg/mL.

In some embodiments, an anti-CD200 antibody is for use, and formulated as such, as a monotherapy. In some embodiments, an anti-CD200 antibody can be formulated with, or for use with, one or more additional active agents. For example, the one or more additional active agents can be useful for prolonging the survival of an allograft organ in a mammal. Such agents include, e.g., the monoclonal anti-CD3 antibody OKT3, anti-thymocyte globulin (ATG), cyclosporine A, or tacrolimus (FK 506). Additionally, glucocorticoids and/or azathioprine (or other purine analogs) may be administered to the host prior to transplant. Drugs used to aid in preventing or inhibiting transplant rejection include, but are not limited to, ATG or ALG, OKT3, daclizumab, basiliximab, corticosteroids, 15-deoxyspergualin, LF15-0195, cyclosporine, tacrolimus, purine analogs such as azathioprine, methotrexate, a mycophenolate compound (e.g., mycophenolate mofetil or mycophenolate sodium), 6-mercaptopurine, bredinin, brequinar, leflunomide, cyclophosphamide, sirolimus, anti-CD4 monoclonal antibodies, CTLA4-Ig, rituxan, anti-CD154 monoclonal antibodies, anti-LFA1 monoclonal antibodies, anti-LFA-3 monoclonal antibodies, anti-CD2 monoclonal antibodies, and anti-CD45 antibodies.

The numerous drugs utilized to delay graft rejection (i.e., to prolong graft survival) work in a variety of ways. Cyclosporine A is one of the most widely used immunosuppressive drugs for inhibiting graft rejection. It is an inhibitor of interleukin-2 or IL-2 (it prevents mRNA transcription of interleukin-2). More directly, cyclosporine inhibits calcineurin activation that normally occurs upon T cell receptor stimulation. Calcineurin dephosphorylates NFAT (nuclear factor of activated T cells), thereby enabling NFAT to enter the nucleus and bind to interleukin-2 promoter. By blocking this process, cyclosporine A inhibits the activation of the CD4$^+$ T cells and the resulting cascade of events which would otherwise occur. Tacrolimus is another immunosuppressant that acts by inhibiting the production of interleukin-2 via calcineurin inhibition. Rapamycin (sirolimus), SDZ RAD, and interleukin-2 receptor blockers are drugs that inhibit the action of interleukin-2 and therefore prevent the cascade of events described above Inhibitors of purine or pyrimidine biosynthesis are also used to inhibit graft rejection. These inhibitors prevent DNA synthesis and thereby inhibit cell division including T cell proliferation. The result is the inhibition of T cell activity by preventing the formation of new T cells Inhibitors of purine synthesis include azathioprine, methotrexate, mycophenolate mofetil (MMF), mycophenolate sodium (Novartis), and mizoribine (bredinin) Inhibitors of pyrimidine synthesis include brequinar sodium and leflunomide.

Cyclophosphamide is an inhibitor of both purine and pyrimidine synthesis. Yet another method for inhibiting T cell activation is to treat the recipient with antibodies to T cells. OKT3 is a murine monoclonal antibody against CD3 which is part of the T cell receptor. This antibody initially activates T cells through the T cell receptor, then induces apoptosis of the activated T cell.

Numerous other drugs and methods for delaying allotransplant rejection are known to and used by persons of skill in the art. One approach is to deplete T cells, e.g., by irradiation. Depletion of T cells has often been used in bone marrow transplants, especially if there is a partial mismatch of major HLA. Administration to the recipient of an inhibitor (blocker) of the CD40 ligand-CD40 interaction and/or a blocker of the CD28-B7 interaction has also been used (U.S. Pat. No. 6,280,957). PCT application publication no. WO 01/37860 discloses the administration of an anti-CD3 antibody and IL-5 to inhibit the Th1 immune response. PCT application publication no. WO 00/27421 teaches a method for prophylaxis or treatment of corneal transplant rejection by administering a tumor necrosis factor-α antagonist. Glotz et al. (2002) *Am J Transplant* 2:758-760 show that administration of intravenous immunoglobulins (IVIg) can induce a profound and sustained decrease in the titers of anti-HLA antibodies thereby allowing survival of an HLA-mismatched organ. Similar protocols have included plasma exchanges (Xaube et al. (1984) *Lancet* 1:824-828) or immunoadsorption techniques coupled to immunosuppressive agents (Hiesse et al. (1992) *Nephrol Dial Transplant* 7:944-951) or a combination of these methods (Montgomery et al., 2000 *Transplantation* 70:887-895). Changelian et al. (2003) *Science* 302:875-878 disclose a model in which immunosuppression is caused by an oral inhibitor of Janus kinase 3 (JAK3), which is an enzyme necessary for the proper signaling of cytokine receptors which use the common gamma chain (γc) (Interleukins-2, -4, -7, -9, -15, -21), the result being an inhibition of T cell activation.

Antisense nucleic acids against ICAM-1 have been used alone or in combination with a monoclonal antibody specific for leukocyte-function associated antigen 1 (LFA-1) in a study of heart allograft transplantation (Stepkowski, supra). Similarly, an anti-ICAM-1 antibody has been used in combination with anti-LFA-1 antibody to treat heart allografts (Stepkowski, supra). Antisense oligonucleotides have additionally been used in conjunction with cyclosporine in rat heart or kidney allograft models, resulting in a synergistic effect to prolong the survival of the grafts (Stepkowski, supra). Chronic transplant rejection has been treated by administering an antagonist of TGF-β, which is a cytokine involved in differentiation, proliferation, and apoptosis (U.S. patent application publication no. 2003/0180301).

When the anti-CD200 antibody is to be used in combination with a second active agent, or when two or more different anti-CD200 antibodies are to be used, the agents can be formulated separately or together. For example, the respective pharmaceutical compositions can be mixed, e.g., just prior to administration, and administered together or can be administered separately, e.g., at the same or different times (see below).

As described above, a composition can be formulated such that it includes a therapeutically effective amount of an anti-CD200 antibody or the composition can be formulated to include a sub-therapeutic amount of the antibody and a sub-therapeutic amount of one or more additional active agents such that the components in total are therapeutically effective for prolonging the survival of an allograft in a mammal. In some embodiments, a composition can be formulated to include two or more anti-CD200 antibodies, each at sub-therapeutic doses, such that the antibodies in combination are at a concentration that is therapeutically effective for prolonging graft survival. Methods for determining a therapeutically effective dose of an anti-CD200 antibody are known in the art and described herein.

Biological Samples and Sample Collection

Suitable biological samples for use in the methods described herein include any biological fluid, population of cells, or tissue or fraction thereof, which includes one or more white blood cell populations. A biological sample can be, for example, a specimen obtained from a subject (e.g., a mammal such as a human) or can be derived from such a subject. For example, a sample can be a tissue section obtained by biopsy, or cells that are placed in or adapted to tissue culture. A biological sample can also be a biological fluid such as urine, whole blood or a fraction thereof (e.g., plasma), saliva, semen, sputum, cerebral spinal fluid, tears, or mucus. A biological sample can be further fractionated, if desired, to a fraction containing particular cell types. For example, a whole blood sample can be fractionated into serum or into fractions containing particular types of blood cells such as red blood cells or white blood cells (leukocytes). If desired, a biological sample can be a combination of different biological samples from a subject such as a combination of a tissue and fluid sample. In some embodiments, the biological sample comprises spleen tissue or splenic immune cell populations.

The biological samples can be obtained from a subject, e.g., a recipient mammal bearing an allograft organ such as an allograft kidney or heart. Any suitable methods for obtaining the biological samples can be employed, although exemplary methods include, e.g., phlebotomy, swab (e.g., buccal swab), lavage, or fine needle aspirate biopsy procedure. Non-limiting examples of tissues susceptible to fine needle aspiration include lymph node, lung, thyroid, breast, and liver. Biological samples can also be obtained from bone marrow. Samples can also be collected, e.g., by microdissection (e.g., laser capture microdissection (LCM) or laser microdissection (LMD)), bladder wash, smear (PAP smear), or ductal lavage.

Methods for obtaining and/or storing samples that preserve the activity or integrity of cells in the biological sample are well known to those skilled in the art. For example, a biological sample can be further contacted with one or more additional agents such as appropriate buffers and/or inhibitors, including protease inhibitors, the agents meant to preserve or minimize changes in the cells (e.g., changes in osmolarity or pH) or denaturation of cell surface proteins (e.g., GPI-linked proteins) or GPI moieties on the surface of the cells. Such inhibitors include, for example, chelators such as ethylenediamine tetraacetic acid (EDTA), ethylene glycol tetraacetic acid (EGTA), protease inhibitors such as phenylmethylsulfonyl fluoride (PMSF), aprotinin, and leupeptin. Appropriate buffers and conditions for storing or otherwise manipulating whole cells are described in, e.g., Pollard and Walker (1997), "Basic Cell Culture Protocols," volume 75 of *Methods in molecular biology*, Humana Press; Masters (2000) "Animal cell culture: a practical approach," volume 232 of *Practical approach series*, Oxford University Press; and Jones (1996) "Human cell culture protocols," volume 2 of *Methods in molecular medicine*, Humana Press.

A sample also can be processed to eliminate or minimize the presence of interfering substances. For example, a biological sample can be fractionated or purified to remove one or more materials (e.g., cells) that are not of interest. Methods of fractionating or purifying a biological sample include, but are not limited to, flow cytometry, fluorescence activated cell sorting, and sedimentation.

Biomarkers and Applications

The inventors have identified and provided herein several biomarkers, a change in one or more of which being consistent with the production of a desired immunomodulatory effect by an anti-CD200 antibody administered to a recipient mammal bearing an allograft organ. That is, a change in one or more of the identified biomarkers is correlated with prolonged allograft survival in a recipient mammal. The biomarkers are recited below in this section and exemplified in the working examples.

A "desired immunomodulatory effect," an "anti-CD200 antibody-associated immunomodulatory effect," and grammatically similar terms, as used herein, refer to a measurable, desirable immunological effect in a mammal attributable to the biological activity of an anti-CD200 antibody administered to the mammal. For example, the inventors have observed that following administration of an anti-CD200 antibody (e.g., in combination with at least one immunosuppressive agent) to a mammal, the concentration of regulatory T cells increases, whereas the concentration of $CD3^+CD4^+$ and $CD3^+CD8^+$ T cells decreases in recipient mammals bearing allografts. Also observed was that upon administration of an anti-CD200 antibody, the expression level of CD40, MHC class II, and CD80, by $CD11c^+$ ($CD49b^-$) cells (e.g., $CD11c^+$ ($CD49b^-$) antigen presenting cells) decreases, whereas the intracellular expression level of IL-12 increased in this subset. Additional changes in the concentration of several immune cell populations (e.g., $F4/80^+CD45^+$, $CD3^+CD25^+$, $CD3^+CD200R^+$, and $CD19^+$ $CD45^+$ cells) were also observed in allograft recipient mammals treated with an anti-CD200 antibody. While not being bound by any particular theory or mechanism of action, the inventors believe that monitoring a mammal treated with an anti-CD200 antibody (and optionally one or more immunosuppressive agents) for a change (e.g., an increase or decrease) in one or more of these biomarkers is useful for, among other things, determining whether the anti-CD200 antibody is capable of producing a biological effect in the mammal to whom the antibody is administered. Moreover, monitoring changes in one or more of the biomarkers is also useful for identifying a dose—a threshold dose (or a dosing schedule)—of an anti-CD200 antibody, such as samalizumab, that by virtue of its immunomodulatory effect in the mammal, is sufficient to achieve a clinically-meaningful effect in the disease (i.e., sufficient to prolong the survival of an allograft in a recipient mammal).

Thus, in accordance with the present disclosure, to determine whether an anti-CD200 antibody (e.g., a variant anti-CD200 antibody that has reduced or no effector function) has produced a desired immunomodulatory effect (e.g., an anti-CD200 antibody-associated immunomodulatory effect) in a mammal (e.g., a human), a practitioner can measure, e.g., the concentration of regulatory T cells (e.g., $CD4^+$ $CD25^+FoxP3^+$ cells) in a biological sample from a mammal administered an anti-CD200 antibody. An increase in the concentration of the cells in the sample as compared to the concentration of cells of the same histological type in a control sample indicates that the anti-CD200 antibody has produced a desired immunomodulatory effect in the mammal. In some embodiments, the practitioner need not measure first-hand the concentration of the regulatory T cells in the biological sample. For example, a practitioner (e.g., a medical professional or a diagnostic scientist or technician) provided with information regarding: (i) the concentration of regulatory T cells in a biological sample from an allograft recipient mammal administered the antibody and (ii) a control cell concentration can determine whether the antibody has produced a desired immunomodulatory effect in the human using the information, e.g., comparing the concentration of regulatory T cells in the biological sample with the concentration of such cells in the control sample, wherein an increase in the concentration of the regulatory T cells in the biological sample as compared to a control concentration of the cells indicates that the anti-CD200 antibody has produced a desired immunomodulatory effect in the human.

Similarly, methods for determining whether a desired immunomodulatory effect has occurred in the mammal can include, e.g., determining the concentration of $Gr\text{-}1^+CD11b^+$ $CD45^+$ cells in a biological sample obtained from an allograft recipient mammal treated with an anti-CD200 antibody (and optionally with at least one immunosuppressive agent), wherein an increase in the concentration of the $Gr\text{-}1^+CD11b^+CD45^+$ cells as compared to a control concentration of $Gr\text{-}1^+CD11b^+CD45^+$ cells, indicates that the anti-CD200 antibody has produced a desired immunomodulatory effect in the recipient mammal.

Methods for determining whether a desired immunomodulatory effect has occurred in the mammal can include, e.g., determining the concentration of $F4/80^+CD45^+$ cells in a biological sample obtained from an allograft recipient mammal treated with an anti-CD200 antibody (and optionally with at least one immunosuppressive agent), wherein a reduction in the concentration of the $F4/80^+CD45^+$ cells as compared to a control concentration of $F4/80^+CD45^+$ cells, indicates that the anti-CD200 antibody has produced a desired immunomodulatory effect in the recipient mammal.

Methods for determining whether a desired immunomodulatory effect has occurred in the mammal can include, e.g., determining the concentration of $CD3^+CD25^+$ cells in a biological sample obtained from an allograft recipient mammal treated with an anti-CD200 antibody (and optionally with at least one immunosuppressive agent), wherein a reduction in the concentration of the $CD3^+CD25^+$ cells as compared to a control concentration of $CD3^+CD25^+$ cells, indicates that the anti-CD200 antibody has produced a desired immunomodulatory effect in the recipient mammal.

Methods for determining whether a desired immunomodulatory effect has occurred in the mammal can include, e.g., determining the concentration of $CD3^+CD8^+$ cells or $CD3^+CD8^+$ cells in a biological sample obtained from an allograft recipient mammal treated with an anti-CD200 antibody (and optionally with at least one immunosuppressive agent), wherein a reduction in the concentration of one or both of these cell populations as compared to a control concentration of the cells, indicates that the anti-CD200 antibody has produced a desired immunomodulatory effect in the recipient mammal.

In some embodiments, to determine whether an anti-CD200 antibody (e.g., a variant anti-CD200 antibody that has reduced or no effector function) has produced a desired immunomodulatory effect in a recipient mammal (and thereby the mammal has been administered a dose of the antibody sufficient to affect the treatment of the mammal via, among other things, its immunomodulatory activity), a practitioner can measure the concentration of $CD3^+CD200R^+$ cells in a biological sample from a mammal administered an anti-CD200 antibody. An increase in the concentration of $CD3^+CD200R^+$ cells in the biological sample as compared to the concentration of cells of the same histological type in a control sample indicates that the anti-CD200 antibody has produced a desired immunomodulatory effect in the mammal. While not being bound by any particular theory or mechanism of action, the inventors believe that an increase in the concentration of $CD3^+CD200R^+$ cells is potentially a compensatory response by these cells to the anti-CD200 antibody. Thus, the concentration of $CD3^+CD200R^+$ cells serves as an indirect biomarker to monitor (or detect) the immunomodulatory effect of an anti-CD200 antibody in the mammal to which the anti-CD200 antibody is administered.

It is understood that the methods for determining whether a desired immunomodulatory effect has occurred in a recipient mammal can involve an analysis of two or more (e.g., two, three, four, five, six, seven, eight, or nine) of the biomarker cell populations disclosed herein.

Methods for measuring the concentration of specific cell populations (e.g., $CD4^+CD25^+FoxP3^+$ regulatory T cells) are well known in the art and include, among other methods, flow cytometry. See, e.g., Chen et al. (2009) *Mol Immunol* 46(10):1951-1963. In some embodiments, a practitioner can interrogate a biological sample obtained from a post-treatment patient (a patient to which an anti-CD200 antibody has already been administered) for the concentration of cells of a particular subset of cells. For example, a practitioner can determine the concentration of $CD3^+CD4^+$ T cells and/or the concentration of activated $CD3^+/CD8^+$ T cells present in a biological sample from a post-treatment patient. In each of these two cases, a reduction in the concentration of the cells of the given subset, as compared to control concentration of cells of the same histological type, indicates that the anti-CD200 antibody has produced in the human a desired immunomodulatory effect.

As described above, determining whether an anti-CD200 antibody (e.g., a variant anti-CD200 antibody with decreased or no effector function) has produced a desired immunomodulatory effect in a human can be performed by comparing the concentration of cells of a specific subtype in a biological sample obtained from a patient following administration of the anti-CD200 antibody (the post-treatment $CD4^+CD25^+FoxP3^+$ regulatory T cell concentration) to the concentration of cells of the same histological type in a control sample. In some embodiments, control sample is obtained from the patient prior to administering to the patient the anti-CD200 antibody. In some embodiments, the control sample can be (or can be based on), e.g., a collection of samples obtained from one or more (e.g., two, three, four, five, six, seven, eight, nine, 10, 15, 20, 25, 30, 35, or 40 or more) healthy individuals that have not been administered an anti-CD200 antibody (e.g., a control concentration of cells of the same histological type can be an average of the concentration of the cells in one or more control samples obtained from patients who have not been administered an anti-CD200 antibody). In some embodiments, the control sample can be or can be based on, e.g., a collection of samples obtained from one or more (e.g., two, three, four, five, six, seven, eight, nine, 10, 15, 20, 25, 30, 35, or 40 or more) allograft recipient mammals, but who have not been administered an anti-CD200 antibody. For example, to determine whether an anti-CD200 antibody has produced a desired immunomodulatory effect in a human administered the antibody, a practitioner can compare the post-treatment concentration to the typical concentration, or average concentration, of cells of the same histological type present in humans who have not been administered an anti-CD200 antibody or at least do not have a detectable level of an anti-CD200 antibody in a biological sample obtained from the humans.

In some embodiments, determining whether an anti-CD200 antibody (e.g., a variant anti-CD200 antibody having reduced or no effector function) has produced a desired immunomodulatory effect in a human can be performed by querying whether the post-treatment cell concentration falls within a predetermined range indicative of the occurrence of a desired immunomodulatory effect by an anti-CD200 antibody in a human. In some embodiments, determining whether an anti-CD200 antibody has produced a desired immunomodulatory effect in a human can include querying if the post-treatment cell concentration for a given histological type of cell falls above or below a predetermined cut-off value. A cut-off value is typically the concentration of cells of a given histological type above or below which is considered indicative of a certain phenotype—namely the occurrence of a desired immunomodulatory effect in a human produced by an anti-CD200 antibody.

In some embodiments, to determine whether an anti-CD200 antibody (e.g., a variant anti-CD200 antibody that has reduced or no effector function) has produced a desired immunomodulatory effect in the human (and thereby the human has been administered a dose of the antibody sufficient to affect the treatment of the patient via, among other things, its immunomodulatory activity), a practitioner can quantify the expression of CD40, CD80, MHC class II, and/or intracellular IL-12 by antigen presenting cells (e.g., CD11c$^+$CD49b$^-$ cells) in a biological sample from an allograft recipient mammal administered an anti-CD200 antibody. A reduction in the expression level of CD40, CD80, or MHC class II by CD11c$^+$CD49b$^-$ cells in the biological sample as compared to the corresponding expression level by cells of the same histological type in a control sample indicates that the anti-CD200 antibody has produced a desired immunomodulatory effect in the recipient mammal. In contrast, an increase in the intracellular expression level of IL-12 by CD11c$^+$CD49b$^-$ cells in the biological sample as compared to the corresponding expression level by cells of the same histological type in a control sample indicates that the anti-CD200 antibody has produced a desired immunomodulatory effect in the human.

As described above, the practitioner need not measure first-hand the expression level of a given antigen by cells in the blood sample. For example, a practitioner provided with information regarding: (i) the expression level of CD40 by CD11c$^+$CD49b$^-$ cells in a biological sample from the recipient mammal administered the antibody and (ii) the expression level of CD40 by cells of the same histological type in a control sample can determine whether the antibody has produced a desired immunomodulatory effect in the recipient mammal using the information, e.g., comparing the expression level of CD40 by CD11c$^+$CD49b$^-$ cells in the biological sample with the expression level of CD40 by such cells in the control sample, wherein a reduction in the level of CD40 expression by the CD11c$^+$CD49b$^-$ cells in the biological sample as compared to expression level of CD40 by cells of the same histological type in the control sample indicates that the anti-CD200 antibody has produced a desired immunomodulatory effect in the human.

In some embodiments, a practitioner can detect and/or quantitate the level of SHIP expression by immune cells in a biological sample obtained from the recipient mammal as a measure of whether a desired immunomodulatory effect has been produced in the human. In some embodiments, the biological sample is a blood sample. In some embodiments, the biological sample comprises or is cells from a spleen biopsy.

In some embodiments, a reduction in SHIP expression by a plurality of immune cells (e.g., T cells, B cells, macrophages, subsets of any of the foregoing, or a population comprising one or more of the foregoing) by at least 10 (e.g., at least 15, 20, 25, 30, 35, 40, 45, 50, 55, 60, 65, 70, or 75 or more) % indicates that the anti-CD200 antibody has produced a desired immunomodulatory effect in the human.

Suitable methods for quantifying the expression level of SHIP, CD40, CD80, MHC class II, and/or IL-12 by cells (e.g., splenocytes or leukocytes such as T cells) are known in the art and described herein. For example, such methods include Western blotting, dot blotting, and flow cytometry, which are useful for quantifying expression of protein, or reverse transcriptase polymerase chain reaction (RT-PCR) and Northern blotting analysis for quantifying expression of mRNA. See, e.g., Walker et al. (2009) *Exp Neurol* 215(1): 5-19; Rijkers et al. (2008) *Mol Immunol* 45(4):1126-1135; and Voehringer et al. (2004) *J Biol Chem* 279(52):54117-54123. See generally Sambrook et al. (1989) "Molecular Cloning: A Laboratory Manual, $2^{nd}$ Edition," Cold Spring Harbor Laboratory Press, Cold Spring Harbor, N.Y. and Ausubel et al. (1992) "Current Protocols in Molecular Biology," Greene Publishing Associates. Suitable methods for detecting and/or quantitating the expression level of SHIP by immune cells are further exemplified in the working examples.

As described above, in some embodiments, the control sample is a biological sample obtained from the subject recipient mammal prior to administering to the mammal the anti-CD200 antibody. In some embodiments, the control expression level can be based on, e.g., the average expression level of expression of a given antigen by cells of the same histological type obtained from one or more (e.g., two, three, four, five, six, seven, eight, nine, 10, 15, 20, 25, 30, 35, or 40 or more) healthy individuals that have not been administered an anti-CD200 antibody. The control expression level can be based on, e.g., the average expression level of a given antigen by cells of the same histological type obtained from one or more (e.g., two, three, four, five, six, seven, eight, nine, 10, 15, 20, 25, 30, 35, or 40 or more) recipient mammals bearing allografted organs, but who have not been administered an anti-CD200 antibody.

In some embodiments, determining whether an anti-CD200 antibody (e.g., a variant anti-CD200 antibody having decreased or no effector function) has produced a desired immunomodulatory effect in a human can be performed by querying whether the post-treatment expression level of an antigen falls within a predetermined range indicative of the occurrence of an immunomodulatory effect by an anti-CD200 antibody in a human. In some embodiments, determining whether an anti-CD200 antibody has produced a desired immunomodulatory effect in a human can include querying if the post-treatment expression level of a given antigen by a given histological type of leukocytes falls above or below a predetermined cut-off value. In this case, the cut-off value is typically the level of expression (e.g., mRNA or protein expression) by CD11c⁺CD49b⁻ cells above or below which is considered indicative of a certain phenotype—namely the occurrence of a desired immunomodulatory effect in a human produced by an anti-CD200 antibody.

Any of the above described biomarker-based methods can include administering an anti-CD200 antibody to a recipient mammal in an amount and with a frequency to produce and/or maintain in the recipient mammal a desired immunomodulatory effect to thereby prolong the survival of the allograft in the mammal.

Methods for Treatment

The disclosure also features methods for prolonging the survival of an allograft organ in a recipient mammal. In some embodiments, the methods can include administering to a recipient mammal in need thereof an anti-CD200 antibody as a single agent in an amount effective to prolong the survival of a renal allograft in the recipient mammal. In some embodiments, the methods can include administering to a recipient mammal in need thereof an anti-CD200 antibody in combination with one or more immunosuppressive agents to thereby prolong the survival of an allograft.

The compositions can be administered to a subject, e.g., a human subject, using a variety of methods that depend, in part, on the route of administration. The route can be, e.g., intravenous injection or infusion (IV), subcutaneous injection (SC), intraperitoneal (IP), or intramuscular (IM) injection. Certain inhibitors, e.g., small molecules, can be orally administered to a subject.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. (See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety.) The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

A suitable dose of an anti-CD200 antibody described herein, which dose is capable of prolonging the survival of an allograft in a recipient mammal, can depend on a variety of factors including, e.g., the age, sex, and weight of a subject to be treated and the particular antibody used. For example, a different dose of an anti-CD200 antibody may be required to treat a recipient mammal bearing a cardiac allograft as compared to the dose of an antibody that is required to treat the same subject bearing a renal allograft. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will depend upon the judgment of the treating medical practitioner (e.g., doctor or nurse).

An antibody described herein can be administered as a fixed dose, or in a milligram per kilogram (mg/kg) dose. In some embodiments, the dose can also be chosen to reduce or avoid production of antibodies or other host immune responses against one or more of the active antibodies in the composition. While in no way intended to be limiting, exemplary dosages of an antibody include, e.g., 1-100 µg/kg, 0.5-50 µg/kg, 0.1-100 µg/kg, 0.5-25 µg/kg, 1-20 µg/kg, and 1-10 µg/kg, 1-100 mg/kg, 0.5-50 mg/kg, 0.1-100 mg/kg, 0.5-25 mg/kg, 1-20 mg/kg, and 1-10 mg/kg. Exemplary dosages of an antibody described herein include, without limitation, 0.1 µg/kg, 0.5 µg/kg, 1.0 µg/kg, 2.0 µg/kg, 4 µg/kg, and 8 µg/kg, 0.1 mg/kg, 0.5 mg/kg, 1.0 mg/kg, 2.0 mg/kg, 4 mg/kg, and 8 mg/kg.

A pharmaceutical composition can include a therapeutically effective amount of an antibody described herein. Such effective amounts can be readily determined by one of ordinary skill in the art based, in part, on the effect of the administered antibody, or the combinatorial effect of the antibody and one or more additional active agents, if more than one agent is used. A therapeutically effective amount of an antibody described herein can also vary according to factors such as the disease state, age, sex, and weight of the individual, and the ability of the antibody (and one or more additional active agents) to elicit a desired response in the individual, e.g., amelioration of at least one condition parameter, e.g., amelioration of at least one symptom of allograft rejection. A therapeutically effective amount is also one in which any toxic or detrimental effects of the composition are outweighed by the therapeutically beneficial effects.

Suitable human doses of an anti-CD200 antibody described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

The terms "therapeutically effective amount" or "therapeutically effective dose," or similar terms used herein are intended to mean an amount of an agent that will elicit the desired biological or medical response. In some embodiments, a composition described herein contains a therapeutically effective amount of an anti-CD200 antibody. In some embodiments, the composition contains any of the antibodies described herein and one or more (e.g., two, three, four, five, six, seven, eight, nine, 10, or 11 or more) additional therapeutic agents such that the composition as a whole is therapeutically effective. For example, a composition can contain an anti-CD200 antibody described herein and an immunosuppressive agent, wherein the antibody and agent are each at a concentration that when combined are therapeutically effective for prolonging the survival of an allograft in a recipient mammal.

Toxicity and therapeutic efficacy of such compositions can be determined by known pharmaceutical procedures in cell cultures or experimental animals (e.g., animal models of allograft rejection). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An anti-CD200 antibody that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies lies generally within a range of circulating concentrations of the anti-CD200 antibody that include the $ED_{50}$ with little or no toxicity. The dosage may vary within this range depending upon the dosage form employed and the route of administration utilized. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography or by ELISA.

A "subject," as used herein, can be any mammal. For example, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the subject is an infant (e.g., a human infant). In some embodiments, the subject is a female.

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment (such as treatment with a composition comprising an anti-CD200 antibody.

In some embodiments, the anti-CD200 antibody can be administered to the recipient mammal for at least seven (e.g., at least eight, nine, ten, 11, 12, 13, or 14) days following transplantation of an allograft to the recipient mammal. In some embodiments, the anti-CD200 antibody can be administered to the recipient mammal at least once per day. In some embodiments, the anti-CD200 antibody can be administered by continuous infusion, e.g., by way of a pump. In some embodiments, the anti-CD200 antibody can be administered in a dose large enough to remain effective for at least two (e.g., at least two, three, four, five, six, seven, eight, nine, ten, 11, 12, 13, or 14) days following transplantation of an allograft to the recipient mammal, with the antibody being administered as often as necessary to maintain an effective dose (e.g., a single dose may be large enough to remain effective for 14 days, in which event only a single dose would be required once every 14 days or only once if an effective amount of the antibody is required for only 14 days). In some embodiments, the anti-CD200 antibody can be administered to the recipient mammal prior to transplantation of the allograft organ. For example, an anti-CD200 antibody can be administered to a recipient mammal, e.g., at least once per day or once per week prior to transplantation of the allograft organ.

In some embodiments, the mammal is a human. In some embodiments, the allograft is MHC mismatched. In some embodiments, the MHC mismatched allograft is an HLA mismatched allograft. In some embodiments, the recipient mammal is ABO mismatched to the allograft organ.

The donor allograft organ can be, e.g., a kidney, a lung, a heart, a pancreas, vascular tissue, a liver, skin, an eye, a hand, a finger, gastrointestinal tissue, nervous tissue, muscle tissue (e.g., smooth or skeletal muscle tissue), bone or cartilage, bone marrow (e.g., hematopoietic cells), connective tissue, or red blood cells. In some embodiments, the donor graft organ can be a portion of a full organ, e.g., one or more lobes of a liver, islet cells from a pancreas, or the cornea or lens of an eye.

In some embodiments, the methods can include administering to a recipient mammal in need thereof an anti-CD200 antibody in combination with one or more (e.g., one, two, three, four, or five or more) immunosuppressive agents to thereby prolong the survival of an allograft. Suitable immunosuppressive agents for use in the methods are described herein and known in the art.

In some embodiments, an immunomodulatory treatment method such as plasmapheresis, splenectomy, or immunoadsorption, can be used in combination with the anti-CD200 antibody therapy.

In some embodiments, administration of the anti-CD200 antibody allows for a shorter duration of treatment with at least one of the one or more immunosuppressive agents, relative to the duration of treatment with the at least one immunosuppressive agent in the absence of the anti-CD200 antibody. For example, administration of the anti-CD200 antibody to the recipient mammal can reduce the duration of treatment with at least one immunosuppressive agent by at least about 20% (e.g., at least about 25%, 30%, 35%, 40%, 45%, 50%, 55%, 60%, 65%, 70%, 75%, 80%, 85%, 90% or more). In some embodiments, administration of the anti-CD200 antibody allows for a reduced amount of at least one immunosuppressive agent, relative to the amount of the agent in the absence of the anti-CD200 antibody, required to prolong the survival of an allograft in a recipient mammal. For example, administration of the anti-CD200 antibody to the recipient mammal can reduce by at about 20% (e.g., at least about 25%, 30%, 35%, 40%, 45%, 50%, 55%, 60%, 65%, 70%, 75%, 80%, 85%, 90% or more) the amount of at least one immunosuppressive agent necessary to affect increased survival of the allograft organ in a recipient mammal. In some embodiments, administration of the anti-CD200 antibody allows for a shorter duration of treatment and reduced amount of at least one immunosuppressive agent, relative to in the absence of the anti-CD200 antibody, required to prolong the survival of an allograft organ.

As used herein, increased survival includes, e.g., at least about 10% (e.g., at least about 15%, 20%, 25%, 30%, 40%, 45%, 50%, 60%, 70%, 80%, 90%, 100%, 110%, 120%, 130%, 140%, 150% or more than 200%) increase in the survival of an allograft organ as compared to relative allograft organ survival in the absence of treatment with an anti-CD200 antibody (and, in some embodiments, a combination therapy of the antibody and one or more immunosuppressive agents). In some embodiments, administration of an anti-CD200 antibody as a monotherapy (or in combination with one or more immunosuppressive agents) can increase the survival of an allograft in a recipient mammal by at least about 1.5 (e.g., at least about 2, 3, 4, 5, 6, 7, 8, 9, or 10 or more) fold as compared to the relative organ allograft survival in a recipient mammal in the absence of treatment. Survival time can be measured, e.g., in days, weeks, months, or years. In some embodiments, administration of an anti-CD200 antibody in accordance with any of the methods described herein can prolong the survival of an allograft organ in a recipient mammal by at least six months, seven months, eight months, nine months, 10 months, 12 months, 18 months, 24 months, or 36 months.

In some embodiments, administration of an anti-CD200 antibody as a monotherapy to a recipient mammal bearing a renal allograft can lead to long-term survival of the allograft organ. Long term survival of an allograft can be, e.g., at least about 5 years, at least about 7.5 years, at least about 10 years, or at least about 15 years or more following transplantation of the allograft organ.

In some embodiments, the methods described herein can include, after administering the anti-CD200 antibody, monitoring the mammal for a change in the condition of the allograft. Monitoring a mammal for an improvement in allograft survival, as defined herein, means evaluating the subject for a change in a graft rejection parameter, e.g., an improvement in one or more symptoms of the disease. In some embodiments, the evaluation is performed at least 1 hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The human can be evaluated in one or more of the following periods: prior to beginning of treatment; during the treatment; or after one or more elements of the treatment have been administered. Evaluating can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a disorder described herein.

In some embodiments, monitoring the progress and/or effectiveness of a therapeutic treatment includes monitoring the level of CD200 expression before and after treatment. For example, pre-treatment levels of CD200 can be ascertained and, after at least one administration of the therapy, levels of CD200 can again be determined. A decrease in CD200 levels can be indicative of an effective treatment (see below). Measurement of CD200 levels can be used by the practitioner as a guide for increasing dosage amount or frequency of the therapy. It should of course be understood that CD200 levels can be directly monitored or, alternatively, any marker that correlates with CD200 can be monitored.

In some embodiments, e.g., embodiments involving kidney allografts, the methods can include monitoring kidney function before, during, and/or after treatment with an anti-CD200 antibody. Suitable methods for monitoring kidney function are known in the art and include, e.g., monitoring hemoglobin, serum creatinine, proteinuria, blood glucose, and serum lipids in the recipient mammal. See, e.g., Marcen et al. (2010) *NDT Plus* 3 (supplement 2):ii2-ii8; Fiebiger et al. (2004) *Health Qual Life Outcomes* 2:2; and Tinti et al. (2010) *Transplant Proc* 42(1):4047-4048. Suitable methods for monitoring the function of other allograft organs, e.g., heart, lung, liver, or skin, are also well known in the art of medicine.

In some embodiments, after it is determined that an anti-CD200 antibody has produced a desired immunomodulatory effect in a recipient mammal, a medical practitioner may elect to administer to the mammal the anti-CD200 antibody in an amount and with a frequency sufficient to maintain the occurrence of the immunomodulatory effect to thereby prolong the survival of the allograft. Methods for therapeutically administering an anti-CD200 antibody to a human are well known in the art and described in, e.g., U.S. Pat. No. 7,408,041.

It is believed to be beneficial to administer an anti-CD200 antibody to a recipient mammal in an amount and with a frequency sufficient to sustain the changes in the one or more biomarkers described herein. Methods for detecting expression or a change in expression or a change in the concentration of a given cell population are well known in the art (e.g., Western blot, immunohistochemistry, and flow cytometry techniques) and described herein. For example, following the administration of an anti-CD200 antibody to a human, the level of CD40 expression by CD11c$^+$ (CD49b$^-$) cells can be determined by flow cytometry analysis of cells present in a biological sample obtained from a recipient mammal. The CD40 expression level by CD11c$^+$ (CD49b$^-$) cells post-treatment can be compared to a control expression level and/or the level of CD40 expression of the cell of the same histological type prior to treatment with the antibody, wherein a reduction in the level of CD40 expression by the cells indicates that the anti-CD200 antibody has been administered to the recipient mammal in an amount and with a frequency sufficient to reduce CD40 expression by the cells.

Through an iterative process, a medical practitioner can determine the appropriate dose amount, and frequency of administration of each dose, required to maintain the occurrence of an immunomodulatory effect in the mammal. For example, a medical practitioner can administer to a recipient mammal at least two (e.g., at least three, four, five, six, seven, or eight or more) times an anti-CD200 antibody in an amount that reduces (or is at least expected to reduce) the level of expression of CD40 by the CD11c$^+$CD49b$^-$ antigen presenting cells. The at least two doses should be spaced apart in time by at least one (e.g., at least two, three, four, five, six, seven, eight, nine, 10, 11, 12, 13, or even 14) day(s). Biological samples (e.g., blood or tissue samples (e.g., spleen tissue samples)) containing immune cell populations of interest are obtained from the mammal at various times, e.g., prior to the first anti-CD200 antibody administration, between the first dose and at least one additional dose, and at least one biological sample collection following the second dose. In some embodiments, biological samples may be collected at least two times between doses and/or at least one time after the final dose administered to the recipient mammal. The subject cells in each biological sample obtained are then interrogated for expression of a specific antigen (e.g., CD40, CD80, MHC class II, or IL-12) or quantified to determine their concentration, ultimately to determine whether the amount and/or the frequency of administration of the anti-CD200 antibody are sufficient to maintain an immunomodulatory effect in the recipient mammal.

Kits

The disclosure also features therapeutic kits containing, among other things, one or more of the anti-CD200 antibodies described herein. The antibodies can be in solution or, e.g., in dry form (e.g., lyophilized or freeze-dried form). Kits comprising a dry form of one or more anti-CD200 antibodies can also include, e.g., one or more solutions useful for solubilizing the antibody such as pharmaceutically acceptable buffers, carriers, excipients, etc. The therapeutic kits can contain, e.g., a suitable means for delivery of one or more anti-CD200 antibodies to a patient in need thereof, e.g., a mammal afflicted with, suspected of having, or at risk for developing, an inflammatory disorder. In some embodiments, the kits contain a suitable means for delivery of the antibodies to a mammal bearing an allografted organ or to the donor mammal from which the allograft organ was obtained. In some embodiments, the means is suitable for invasive (e.g., intravascular (e.g., intravenous), subcutaneous, or intramuscular) delivery of the solution to a mammal. In some embodiments, the means is suitable for subcutaneous delivery of the antibody or antigen-binding fragment thereof to the subject. For example, the means can be a syringe or an osmotic pump. In some embodiments, the kit contains a means that is pre-loaded with an anti-CD200 antibody solution to be administered to a mammal. For example, a therapeutic kit can contain a syringe pre-filled with an aqueous solution (e.g., a pen device containing the solution) described herein or the kit can contain a pump (e.g., an osmotic pump) and one or more disposable cassettes configured for use with the pump, the cassettes pre-filled with an aqueous solution described herein. In some embodiments, the means for delivering the high concentration solution is a pen device for drug delivery.

In some embodiments, for example, in embodiments where an anti-CD200 antibody is to be administered to a mammal in combination with one or more immunosuppressive agents, the kit can include one or more additional immunosuppressants such as any recited herein. For example, a therapeutic kit can include, without limitation, adriamycin, azathioprine, busulfan, cyclophosphamide, cyclosporine A, fludarabine, 5-fluorouracil, methotrexate, mycophenolate mofetil, mycophenolate sodium, a non-steroidal anti-inflammatory drug, an mTOR inhibitor such as rapamycin, and/or FK-506. In some embodiments, the kits can include one or more IL-2 inhibitors such as any of those described herein.

The following examples are intended to illustrate, not limit, the invention.

EXAMPLES

Example 1

Single-Agent Therapy for Prolonging Renal Allograft Survival

Allograft rejection is generally treated with one or more immunosuppressive agents, e.g., calcineurin inhibitors, many of which either alone or in combination can result in serious adverse drug interactions and side-effects including, but not limited to: alopecia, bone marrow depletion, gastrointestinal upset, pruritis, thrombocytopenia, anemia, nephrotoxicity, pancreatitis, and infection. Moreover, in order to maintain graft survival in patients it is often necessary to continue to administer the one or more immunosuppressants chronically, sometimes for the life of the patient. Thus, it is of great value to identify novel compounds capable of prolonging with fewer adverse effects the survival of grafts in recipient mammals as an alternative to current immunosuppressive therapies.

The present study involved the evaluation of an anti-CD200 antibody as a monotherapy for prevention, delay, or reduction in the severity of renal allograft rejection using a fully-MHC mismatched life-supporting renal transplantation mouse model. The subject murine, monoclonal anti-CD200 antibody binds to mouse CD200 and inhibits the interaction between mouse CD200 and its CD200 receptor. The amino acid sequence of the variable region of this antibody is set forth in PCT application publication no. WO 09/014,745 (particularly, e.g., FIG. 10, OX90mG2a), the disclosure of which is incorporated herein by reference in its entirety. This murine anti-CD200 antibody is effectorless—comprising a variant IgG2a heavy chain constant region in which the CH2 domain contains a D265A substitution (heavy chain amino acid numbering according to Kabat et al. (supra)). The substitution results in a complete loss of interaction between the variant constant region and IgG Fc receptors FcγRIIB, FcγRIII, FcγRI, and FcγRIV. See, e.g., Baudino et al. (2008) *J Immunol* 181:6664-6669 (supra). In addition, the FcγRI binding site of the antibody was made nonfunctional by substituting the leucine at position 236 with a glutamic acid residue. The C1q binding site was made nonfunctional by substituting glutamic acid 319, lysine 321 and lysine 323 with alanine residues (Steurer et al. (1995) *J Immunol* 155:1165). Furthermore, asparagine at position 298 of the heavy chain was changed to glutamine to eliminate the conserved N-linked glycosylation site. In accordance with the instant disclosure, the murine anti-CD200 antibody is one containing a variant heavy chain constant region having reduced effector function relative to the non-variant form of the heavy chain constant region. The control antibody used in the experiment described in this section is a murine monoclonal antibody, which does not bind to CD200. The control antibody, like the anti-CD200 antibody, comprises a variant IgG2a heavy chain constant region in which the CH2 domain contains a D265A substitution, thereby rendering the control antibody "effectorless."

In the studies described in this section, BALB/c mice were renal allograft recipients and C57BL/6 mice were donors of the renal allografts. The mice were approximately 10 weeks old, weighing approximately 22-23 grams at the time of surgery. Left renal transplants were performed in this study. After bilateral nephrectomies in the recipient, the harvested C57BL/6 donor graft was revascularized with end-to-side anastomoses between the donor renal artery and the recipient abdominal aorta. The donor renal vein and recipient inferior vena cava were also joined. Subsequently, an end-to-end ureteric anastomosis was made. Graft rejection leading to death was the indicator for the endpoint of rejection, while mice with long-term surviving grafts were euthanized at postoperative day (POD) 100. Given the time constraints on the number of individual surgeries that can be performed during a single day, the surgeries, even within experimental groups of mice, were staggered over several days. However, all surgeries were performed by the same microsurgeon to ensure consistency.

The study included six groups of eight mice, each mouse bearing a life-supporting renal allograft. The groups were treated under the following dosing schedules, with dosing beginning at the time of transplant: (1) graft-bearing mice intravenously administered 75 μg of the anti-CD200 antibody each day for 14 days; (2) graft-bearing mice intravenously administered each day for 14 days 75 μg of an effectorless control antibody, which does not bind to CD200 but contains the aforementioned mutations including the D265A substitution; (3) graft-bearing mice subcutaneously administered the anti-CD200 antibody each day for 14 days; (4) graft-bearing mice subcutaneously administered each day for 14 days 75 μg of the effectorless control antibody; (5) graft-bearing mice intravenously administered 75 μg of the anti-CD200 antibody each day for seven days; and (6) graft-bearing mice intravenously administered 75 μg of the control antibody each day for seven days.

The results of the experiment, by experimental Group, are set forth in Table 1.

TABLE 1

Results of Single Agent Administration of an Anti-CD200 Antibody

| Group | Individual Survival† (days) | Mean Survival (days) |
|---|---|---|
| 1 | >100, >100, >100, >100, >100, >100, >100, >100 | >100 |
| 2 | 29, 35, 37, 37, 38, 40, 42, 43 | 37.6 ± 4.4 |
| 3 | >100, >100, >100, >100, >100, >100, >100, >100 | >100 |
| 4 | 31, 36, 37, 38, 38, 40, 46, 47 | 39.1 ± 5.3 |
| 5 | >100, >100, >100, >100, >100, >100, >100, >100 | >100 |
| 6 | 33, 35, 37, 37, 38, 41, 43, 46 | 34.1 ± 4.6 |

†Each number in this column represents the survival measured in days for an individual mouse of a given group.
A numeric value annotated with a ">" refers to a subject mouse that continues to survive beyond the number of days indicated.

As shown in Table 1, graft-bearing mice from each of the three groups treated with the control antibody died as a result of graft rejection less than 40 days after transplantation −34.1±4.6, 39.1±5.3, and 37.6±4.4 for Groups 6, 4, and 2 mice, respectively. In contrast, all mice from Groups 1, 3, and 5 survived to the study end point: >100 days.

The results of this experiment indicate that an anti-CD200 antibody administered as a single agent therapy prolongs renal allograft survival in mice. The results also indicate that administration of an anti-CD200 antibody as a single agent for a limited duration (e.g., daily for between seven to 14 days), rather than chronically beyond 14 days or for the duration of the time the allograft organ is resident in the recipient, is effective to condition the allograft organ for survival in the host.

Example 2

Single-Agent Therapy for Prolonging Renal Allograft Survival in Presensitized Recipients A series of experiments, similar to those described in Example 1, were performed to evaluate the ability of the above-described therapeutic anti-CD200 antibody as a single agent to prolong renal allograft survival in a presensitized recipient mammal. In these experiments, the presensitization was induced by prior immunization of donor splenocytes to the recipient mammals.

For these experiments BALB/c recipient mice were pre-sensitized by injecting intraperitoneally recipient mice with $5 \times 10^6$ C57BL/6 mouse donor splenocytes 14 days prior to renal transplantation from the same donor (using the method of Pruitt and Bollinger (1991) *J Surg Res* 50(4):350-355). This model is designed to mimic presensitized transplantation in humans, especially in relation to accelerated humoral rejection. In general, presensitization can occur not only as a result of having received an earlier allograft, but can also be caused by having received multiple blood transfusions or in women who have been pregnant. Besides such presensitization methods, allografts with an ABO mismatch will be rapidly attacked and rejected because of preformed antibodies to the ABO antigens unless steps are taken to prevent such an attack.

The study included four groups of five to seven mice, each mouse bearing a life-supporting renal allograft. The groups were treated under the following dosing schedules in Table 2, with dosing beginning at the time of transplant.

TABLE 2

| Group | N | Treatment (Concurrent) | | |
|---|---|---|---|---|
| | | Antibody[1] | MMF[2] | FK-506[3] |
| 1 | 5 | α-CD200*, 75 µg per day for 14 days | NA | NA |
| 2 | 5 | Control Ab, 75 µg per day for 14 days | NA | NA |
| 3 | 6 | α-CD200*, 75 µg per day for 14 days | 80 mg/kg per day for 14 days | NA |
| 4 | 7 | α-CD200*, 75 µg per day for 14 days | NA | 8 mg/kg per day for 14 days |

[1]The antibody, whether the anti-CD200 antibody or control antibody, was subcutaneously administered to the recipient mammal.
[2]"MMF" refers to mycophenolate mofetil and was administered orally.
[3]FK-506 was administered orally.
*Murine monoclonal anti-CD200 antibody described in Example 1.
"Control Ab" refers to the control antibody described in Example 1.
N refers to the number of renal allograft-bearing mice in each group.

The interim results of this ongoing experiment are provided in Table 3.

TABLE 3

Results* of Single Agent Administration of an Anti-CD200 Antibody using the Pre-sensitized Model

| Group | Individual Survival† (days) | Mean Survival Time | P value (T-test) |
|---|---|---|---|
| 1 | 37, 38, 41, 42, 45 | 40.6 ± 1.4 | vs Group 2, P = 0.009 |
| 2 | 13, 13, 14, 14, 15 | 13.8 ± 0.4 | |
| 3 | 65, 67, 70, 72, 77, 80 | 71.8 ± 2.4 | vs Group 1, P = 0.043; vs Group 5, P = 0.0034 |
| 4 | 33*, 40, 56, 60, 62, 64, 65 | 54.3 ± 4.8 | vs Group 1, P = 0.149 |

†Each number in this column represents the survival measured in days for an individual mouse of a given group.
*The mouse died on day 33.

As evidenced by the initial results provided in Table 3, all five of the mice under evaluation in Group 2 (presensitized graft-bearing mice treated with the control antibody) survived no longer than 15 days. In contrast, the mean graft survival of Group 1 graft-bearing mice under observation was 40.6±1.4 days. Similarly, the mean graft survival times observed for the grafts of Groups 3 and 4 mice were 71.8±2.4 and 54.3±4.8, respectively. These results indicate that treatment of presensitized renal allograft-bearing mice with an anti-CD200 antibody as a single agent can prolong the survival of the renal allografts in the mice. The results also underscore that subcutaneous delivery of an anti-CD200 antibody to a recipient mammal bearing a renal allograft is a therapeutically viable route of administration.

Example 3

Therapeutic Equivalency of an IgG2a Anti-CD200 Antibody and an Effectorless Anti-CD200 Antibody An experiment was performed to evaluate the therapeutic efficacy—in prolonging the survival of an allograft—of an effectorless anti-CD200 antibody as compared to an anti-CD200 antibody that possesses effector function (in this case an IgG2a antibody).

The studies described in this section examined graft survival in a C57BL/6 to BALB/c fully MHC-mismatched mouse heart transplantation model. Each experimental group included 4-6 animals. Some of the experimental groups were treated with antibodies. Antibody 1 is a murine, monoclonal anti-CD200 antibody that binds to mouse CD200 and inhibits the interaction between mouse CD200 and its CD200 receptor. Antibody 1, the anti-CD200 antibody described in Example 1, is effectorless. Antibody 2, the control antibody described in Example 1, is a murine monoclonal antibody, which does not bind to CD200. Antibody 2 also comprises a variant IgG2a heavy chain constant region in which the CH2 domain contains a D265A substitution, thereby rendering the control antibody "effectorless." Antibody 3 is a murine monoclonal antibody that shares a variable region with Antibody 1. Antibody 3 contains a non-variant form of the heavy chain IgG2a constant region and thus possesses effector function. Antibody 4 is a control, murine monoclonal antibody that shares a variable region with Antibody 2. Antibody 4 also contains a non-variant form of the IgG2a heavy chain constant region and thus possesses effector function.

The mice of each group were treated as follows, with dosing beginning at the time of transplant:

Group 1: graft-bearing mice were untreated;

Group 2: graft-bearing mice were subcutaneously administered cyclosporine A each day of the study at a dose of 15 mg/kg;

Group 3: graft-bearing mice were subcutaneously administered cyclosporine A each day of the study at a dose of 5 mg/kg;

Group 4: Antibody 3 was intravenously administered to each graft-bearing mouse once per day for 14 days at a dose of 100 µg and, concurrently, the mice were also subcutaneously administered cyclosporine A each day of the study at a dose of 15 mg/kg;

Group 5: Antibody 4 was intravenously administered to each graft-bearing mouse once per day for 14 days at a dose of 100 µg and, concurrently, the mice were also subcutaneously administered cyclosporine A each day of the study at a dose of 15 mg/kg;

Group 6: Antibody 1 was intravenously administered to each graft-bearing mouse once per day for 14 days at a dose of 100 µg and, concurrently, the mice were also subcutaneously administered cyclosporine A each day of the study at a dose of 15 mg/kg Group 7: Antibody 1 was intravenously administered to each graft-bearing mouse once per day for 14 days at a dose of 100 µg and, concurrently, the mice were also subcutaneously administered cyclosporine A each day of the study at a dose of 5 mg/kg; and Group 8: Antibody 2 was intravenously administered to each graft-bearing mouse once per day for 14 days at a dose of 100 µg and, concurrently, the mice were also subcutaneously administered cyclosporine A each day of the study at a dose of 15 mg/kg;

The results of this experiment are set forth in Table 4.

TABLE 4

| Group | Individual Survival† (days) | Mean Survival (days) |
|---|---|---|
| 1 | 8, 8, 9, 9 | Historical data 8.5 ± 0.6 |
| 2 | 14, 15, 15, 16, 16, 17 | Historical data 15.5 ± 1.1 |
| 3 | 9, 10, 10, 10, 11, 11 | Historical data 10.2 ± 0.8 |
| 4 | 100(A), 100(A), 100(A-), 100(A-), 100(B) | >100 |
| 5 | 15, 16, 16, 17, 17 | 16.2 ± 0.8 |
| 6 | 100(A), 100(A), 100(B), 100(B), 100(B) | >100 |
| 7 | 58, 59, 61, 61, 63 | 60.4 ± 2.0 |
| 8 | 15, 15, 16, 17, 17 | 16 ± 1 |

†Each number in this column represents the survival measured in days for an individual mouse of a given group.
A numeric value annotated with a ">" refers to a subject mouse that continued to survive beyond the number of days indicated.
The degree of pulsation was scored as: "A", beating strongly; "B", mild decline in the intensity of pulsation; "C", noticeable decline in the intensity of pulsation; or "D", complete session of cardiac impulses. "A-" indicates a qualitative degree of pulsation between "A" and "B".

As shown in Table 3, the grafts of Group 4 mice—those treated with a combination therapy of Antibody 1 and 15 mg/ml/day CsA—and the grafts of Group mice—those treated with a combination therapy of Antibody 3 and 15 mg/ml/day CsA—continued to survive in the recipient mice at the time of sacrifice at 100 days post-transplantation. In contrast, allografts in untreated recipient mice had a mean survival time of 8.5 days. Grafts of recipient mice treated with CsA alone (at 15 mg/ml/day) survived, on average, only to approximately day 15. Administration of either control antibody—Antibody 2 or Antibody 4—in combination with 15 mg/kg/day of CsA only maintained survival of allograft hearts to approximately day 16.

In addition to having a markedly extended survival in recipient mice, the cardiac grafts in the mice of Groups 4 and 6 were, by qualitative assessment of pulsation, functioning well. That is, all of the grafts were either beating strongly or only exhibiting mild signs of decline in the intensity of pulsation.

The results of this experiment indicate that therapeutic administration of an anti-CD200 antibody can prolong the survival of an allograft, regardless of whether the antibody possesses, or lacks, effector function. The results also indicate that intravenous administration is a therapeutically effective route of delivery for an anti-CD200 antibody in the treatment of allograft rejection in mammals.

Example 4

Administration of an Anti-CD200 Antibody Allows Early Withdrawal of Immunosuppressive Therapies Even with narrow therapeutic dose ranges, calcineurin inhibitors such as Cyclosporine A (CsA) and FK-506 can be extremely nephrotoxic. Calne et al. (1978) *Lancet* 2:1323-1327 and Gaston (2009) *Clin J Am Soc Nephrol* 4(12):2029-2034. Treatment with subtherapeutic levels of CsA or FK-506 results in significantly lower risk of nephrotoxicity, but with a significant reduction in therapeutic benefit with respect to graft survival. See, e.g., Seron and Moreso (2004) *Transplant Proc* 36:257 S. Given the limitations and side effects attendant to calcineurin therapies, it is clearly of value to identify new compounds capable of reducing the requirement of these inhibitors (whether in dose level or length of treatment) while maintaining a high level of therapeutic efficacy with respect to prolonging graft survival.

1.

An experiment was performed to evaluate whether use of an anti-CD200 antibody can reduce the length of time in which CsA must be administered to a recipient mammal to prolong the survival of an allograft. As described in Example 3, these studies examined graft survival in a C57BL/6 to BALB/c fully MHC-mismatched mouse heart transplantation model. Each experimental group included five (5) animals. The five experimental groups were treated as follows, with dosing beginning at the time of transplant:

Group 1: Antibody 1 (from Example 3) was subcutaneously administered to each graft-bearing mouse once per day for 14 days at a dose of 100 µg and, thereafter, twice per week at the same dose for the remainder of the study; concurrently, the mice were also subcutaneously administered CsA for 42 days at a dose of 15 mg/kg;

Group 2: Antibody 1 was subcutaneously administered to each graft-bearing mouse once per day for 7 days at a dose of 100 µg and, thereafter, twice per week at the same dose for remainder of the study; concurrently, the mice were also subcutaneously administered CsA for 28 days at a dose of 15 mg/kg and, thereafter, once per day at a dose of 5 mg/kg;

Group 3: Antibody 2 (from Example 3) was subcutaneously administered to each graft-bearing mouse once per day for 14 days at a dose of 100 µg and, thereafter, twice per week at the same dose for remainder of the study; concurrently, the mice were also subcutaneously administered CsA for 42 days at a dose of 15 mg/kg;

Group 4: Antibody 1 was subcutaneously administered to each graft-bearing mouse once per day for 14 days at a dose of 100 µg and, thereafter, twice per week at the same dose for the remainder of the study; concurrently, the mice were also subcutaneously administered CsA for 28 days at a dose of 15 mg/kg and, thereafter, once per day at a dose of 5 mg/kg; and Group 5: Antibody 1 was subcutaneously administered to each graft-bearing mouse once per day for 14 days at a dose of 100 µg and, thereafter, twice per week at the same dose for remainder of the study; concurrently, the mice were also subcutaneously administered CsA for the first 14 days at a dose of 15 mg/kg.

The results of this experiment are set forth in Table 5.

TABLE 5

| Group | Individual Survival† (days) | Mean Survival (days) |
|---|---|---|
| 1 | 100(A-), 100(B), 100(B-), 100(B-), 100(B-) | >100 |
| 2 | 100(A), 100(A), 100(A-), 100(A-), 100(A-) | >100 |
| 3 | 15, 15, 17, 18, 20 | 17 ± 2.1 |
| 4 | 100(A), 100(A), 100(A), 100(A), 100(A) | >100 |
| 5 | 29, 35, 36, 37, 42 | 35.8 ± 4.7 |

†Each number in this column represents the survival measured in days for an individual mouse of a given group.
A numeric value annotated with a ">" refers to a subject mouse that continues to survive beyond the number of days indicated.
The degree of pulsation was scored as: "A", beating strongly; "B", mild decline in the intensity of pulsation; "C", noticeable decline in the intensity of pulsation; or "D", complete session of cardiac impulses. "A-" indicates a qualitative degree of pulsation between "A" and "B". "B-" indicates a qualitative degree of pulsation between "B" and "C".

As shown in Table 5, cardiac allografts of Group 3 mice treated with Antibody 2, the control antibody, and CsA exhibited a mean survival time of approximately 17 days. In contrast, the allografts of Group 1 mice, which mice were treated with the anti-CD200 antibody (Antibody 1), continued to thrive at the time of sacrifice at 100 days post-transplantation. Grafts of mice treated with Antibody 1 in combination with CsA at 15 mg/kg/day for the entire study also thrived until the time of sacrifice (100 days), in contrast to the historical mean survival of cardiac allografts treated with CsA alone of 15.5 days (see Example 3, Table 4).

The cardiac allografts of Group 1 mice, which mice were only treated for 42 days with CsA, also continued to thrive at the time of sacrifice. Similarly, the grafts of Group 2 mice, which treatment group involved reduction of the dose of CsA from 15 mg/kg to 5 mg/kg at day 29, also remained viable at the time of sacrifice. Moreover, the grafts of Group 5 mice, who were treated with CsA for only 14 days, exhibited a mean survival time of approximately 35.8 days—a survival time twice as long as chronic CsA treatment at 15 mg/kg/day (Example 3, Table 4, Group 2) and three time as long as chronic CsA treatment at 5 mg/kg/day (Example 3, Table 4, Group 3).

In total, these results indicate that administration of an anti-CD200 antibody is effective to reduce the amount of CsA administered and/or the length of time CsA is administered to recipient mammals, while preserving the graft survival benefits observed in higher doses or more frequent administration of CsA. That is, the results indicate that an anti-CD200 antibody is useful for reducing the requisite therapeutic dose of calcineurin inhibitors such as CsA, while maintaining a high level of therapeutic efficacy with respect to prolonging graft survival.

2.

An experiment was also performed to evaluate whether use of an anti-CD200 antibody can reduce the duration or amount of mycophenolate mofetil that is necessary to prolong the survival of an allograft in a recipient mammal. First, a pilot experiment was performed to determine the dose of, and duration of, mycophenolate mofetil required to prolong allograft survival in mice. As described in Example 3, these studies examined graft survival in a C57BL/6 to BALB/c fully MHC-mismatched mouse heart transplantation model. Each experimental group included five (5) animals. The three experimental groups were treated as follows:

Group 1-PE (pilot experiment): cardiac allograft-bearing mice were orally administered mycophenolate mofetil at a dose of 120 mg/kg each day of the study beginning at the time of transplant;

Group 2-PE: cardiac allograft-bearing mice were orally administered mycophenolate mofetil at a dose of 80 mg/kg each day of the study beginning at the time of transplant; and Group 3-PE: cardiac allograft-bearing mice were orally administered FK-506 at a dose of 16 mg/kg for each day of the study beginning at the time of transplant.

The results of this experiment are provided below in Table 6A.

TABLE 6A

| Group | Individual Survival† (days) | Mean Survival (days) |
|---|---|---|
| 1PE | 20, 21, 22, 23, 25 | 22.2 ± 1.9 |
| 2PE | 18, 19, 20, 22, 22 | 20.2 ± 1.8 |
| 3PE | 23, 25, 25, 26, 27 | 25.2 ± 1.5 |

†Each number in this column represents the survival measured in days for an individual mouse of a given group.

As shown in Table 6A, mean survival time for cardiac allografts in mice treated with the FK-506 regimen (Group 3PE) was approximately 25.2 days. The mean survival time for cardiac allografts in mice treated with a high dose (120 mg/kg; Group 1PE) of mycophenolate mofetil was approximately 22.2 days, whereas mice treated with an intermediate dose (80 mg/kg; Group 2PE) of mycophenolate mofetil maintained their cardiac allografts for approximately 20.2 days.

To determine whether therapeutic administration of an anti-CD200 antibody was effective to reduce the duration and/or amount of immunosuppressant required to prolong a cardiac allograft, the following experiment was performed using the C57BL/6 to BALB/c fully MHC-mismatched mouse heart transplantation model. Each experimental group included five (5) animals. The five experimental groups were treated as follows, with treatment beginning at the time of transplant:

Group 1: Antibody 1 (from Example 3) was subcutaneously administered to each graft-bearing mouse once per day for 14 days at a dose of 100 µg; concurrently, the mice were also orally administered mycophenolate mofetil at 80 mg/kg per day for the entire study;

Group 2: Antibody 2 (from Example 3) was subcutaneously administered to each graft-bearing mouse once per day for 14 days at a dose of 100 µg; concurrently, the mice were also orally administered mycophenolate mofetil at 80 mg/kg per day for the entire study;

Group 3: Antibody 1 (from Example 3) was subcutaneously administered to each graft-bearing mouse once per day for 14 days at a dose of 100 µg; concurrently, the mice were (a) subcutaneously administered cyclosporine A at a dose of 15 mg/kg per day for 28 days and (b) orally administered mycophenolate mofetil at a dose of 80 mg/kg per day for the entire study; and Group 4: Antibody 2 (from Example 3) was subcutaneously administered to each graft-bearing mouse once per day for 14 days at a dose of 100 µg; concurrently, the mice were (a) subcutaneously administered cyclosporine A at a dose of 15 mg/kg per day for 28 days and (b) orally administered mycophenolate mofetil at a dose of 80 mg/kg per day for the entire study.

The results of this experiment are set forth in Table 6B.

TABLE 6B

| Group | Individual Survival† (days) | Mean Survival (days) |
|---|---|---|
| 1 | 62, 63, 63, 64, 65 | 63.4 ± 1.1 |
| 2 | 18, 19, 21, 23, 24 | 21 ± 2.1 |
| 3 | 100(A), 100(A), 100(A), 100(A), 100(A-) | >100 |
| 4 | 36, 39, 40, 41, 41 | 39.4 ± 2.1 |

†Each number in this column represents the survival measured in days for an individual mouse of a given group.
A numeric value annotated with a ">" refers to a subject mouse that continues to survive beyond the number of days indicated.
The degree of pulsation was scored as: "A", beating strongly; "B", mild decline in the intensity of pulsation; "C", noticeable decline in the intensity of pulsation; or "D", complete session of cardiac impulses. "A-" indicates a qualitative degree of pulsation between "A" and "B".

With respect to mycophenolate mofetil, cardiac allografts of Group 1 mice treated with the Antibody 2, the control antibody, and 80 mg/kg per day of MMF exhibited a mean survival time of approximately 21 days, which is similar to the survival time of cardiac grafts treated with only MMF (approximately 20.2 days; see Group 2PE results above). In contrast, the cardiac allografts of mice treated with an anti-CD200 antibody (Antibody 1) and MMF survived over three times as long (approximately 63.4 days). The increased allograft survival time in mice treated with an anti-CD200 antibody was also nearly three times longer than in mice treated with a high dose (120 mg/kg) of MMF (see Table 6A, Group 1PE). These results indicate that therapeutic administration of an anti-CD200 antibody is effective to reduce the amount of MMF, while greatly increasing the survival time of allografts in recipient mammals.

Example 5

Cell Populations as Biomarkers of Efficacy of an Anti-CD200 Antibody Therapy

Early detection of rejection is a major focus of medicine and research in the care of transplant recipients. Detection of allograft organ rejection prior to the onset of organ dysfunction can provide an opportunity for successful treatment of this condition using, e.g., one or more immunosuppressive therapies. It is similarly important to determine whether a compound is therapeutically efficacious, and/or continues to be efficacious, as early as possible to avoid irreversible loss of function of the allograft organ. Early determination can provide the medical practitioner with time and options for altering the dose amount or frequency of a current medication and/or prescribing a new therapy to the patient, which may offer more therapeutic success in preventing graft rejection.

An experiment was performed to study the characteristics of certain immune cell populations in recipient mice bearing a cardiac allograft organ and treated with an anti-CD200 antibody. As administration of an anti-CD200 antibody in combination with at least one immunosuppressive agent can prolong the survival of a cardiac allograft (see above), the experiment sought to characterize the cell populations that are indicative of a pro-graft survival immunomodulatory effect in the recipient mammals. While not bound by any particular theory or mechanism of action, it was believed that changes in such cell populations in animals exhibiting prolonged graft survival could be useful tools for determining therapeutic efficacy or likelihood of therapeutic efficacy in other recipient mammals treated with an anti-CD200 antibody.

The following cell populations were investigated:
(1) $CD11c^+$ $CD49b^-$ dendritic cells, which are dendritic cells selected for using CD11c/CD49b⁻ bead-guided cell sorting;
(2) $CD4^+CD25^+FoxP3^+$ cells, which are regulatory T (Treg) cells. Treg cells are a subset of T cells with the ability to suppress harmful immunological reactions to self and foreign antigens;
(3) $Gr-1^+CD11b^+CD45^+$ cells are myeloid cells, also referred to as myeloid-derived suppressor cells or (MDSCs) [Gabrilovich et al. (2007) *Cancer Res* 67(1):425-426], which are a heterogeneous cellular population containing macrophages, granulocytes, immature dendritic cells, and early myeloid precursors;
(4) $F4/80^+CD45^+$ cells (a macrophage population within an isolated splenocyte population);
(5) $CD3^+CD25^+$ cells, which are a lymphocyte subpopulation;
(6) $CD3^+CD8^+$ cells, which are cytotoxic T cells;
(7) $CD3^+CD4^+$ cells, which are so-called helper T cells;
(8) $CD3^+CD200R^+$ cells, which are a CD200R positive T cell population; and
(9) $CD19^+CD45^+$ cells, which represent a mixed population of pro-B to mature B cells (during development) and follicular dendritic cells.

In addition, CD40, MHC class II, CD80, and IL-12 expression were evaluated on a $CD11c^+CD49b^-$ dendritic cell population.

As described in Examples 3 and 4 above, the present study involved treating cardiac allograft recipient mice (the C57BL/6 to BALB/c fully MHC-mismatched mouse heart transplantation model). Each experimental group included three (3) animals.

The groups of mice were treated as follows (see also Example 4(1), above), with treatment beginning at time of transplant:
Group 1: Antibody 2 (control antibody, Example 3) was intravenously administered to each graft-bearing mouse once per day for 14 days at a dose of 100 µg;
Group 2: Antibody 1 (anti-CD200 antibody lacking effector function, Example 3) was intravenously administered to each graft-bearing mouse once per day for 14 days at a dose of 100 µg;
Group 3: graft-bearing mice were subcutaneously administered CsA each day of the study at a dose of 15 mg/kg for 14 days;
Group 4: Antibody 2 (Example 3) was intravenously administered to each graft-bearing mouse once per day for 14 days at a dose of 100 µg, and, concurrently, the mice were also subcutaneously administered CsA each day of the study at a dose of 15 mg/kg for 14 days; and
Group 5: Antibody 1 (Example 3) was intravenously administered to each graft-bearing mouse once per day for 14 days at a dose of 100 µg, and, concurrently, the mice were also subcutaneously administered CsA each day of the study at a dose of 15 mg/kg for 14 days.

At day 14, mice were sacrificed. Spleens were harvested from the mice and cells isolated for analysis using flow cytometry methods. The methods employed the use of a panel of detectably-labeled monoclonal antibodies, each of which is specific for a given antigen and bears a different fluorophore. Cell populations from each of the three mice from each group were evaluated independently. The results of the characterization of the above-described cell populations are set forth below.

CD40 Expression by CD11$^+$ CD49b$^-$ Dendritic Cells

Using flow cytometry, the level of CD40 expression by CD11$^+$ CD49b$^-$ cells (dendritic cells) obtained from each mouse (N1, N2, and N3) was evaluated. CD40 is a co-stimulatory molecule found on dendritic cells, for example, whose engagement by CD40 ligand results in dendritic cell activation. While not being bound to any particular theory or mechanism of action, a reduction in the level of CD40 by antigen presenting cells (APCs), such as dendritic cells, and thus a reduction in APC activation, would likely inhibit or reduce an anti-graft immune response in a recipient mammal.

Figure 1:
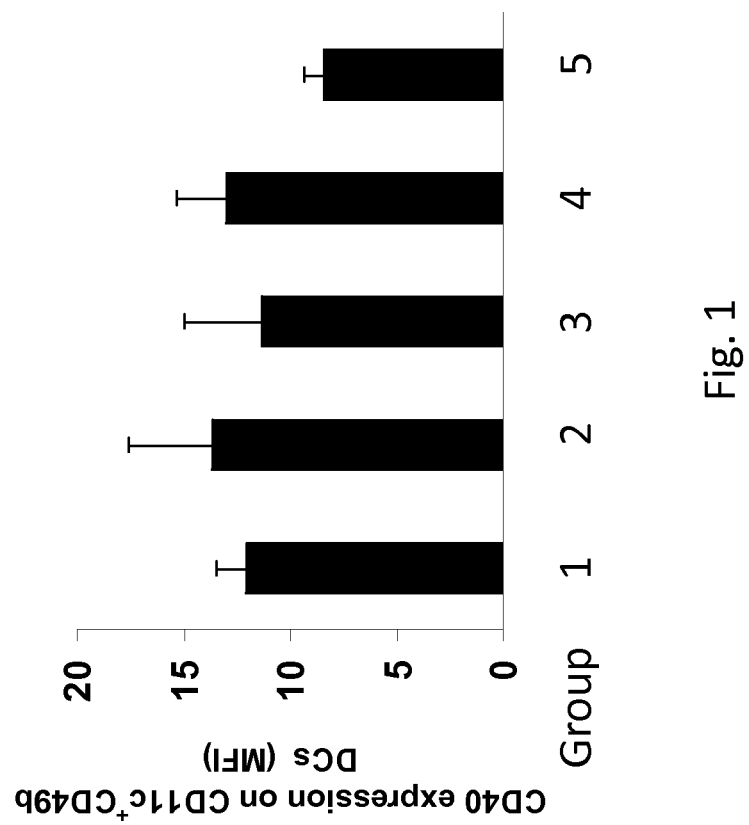
FIGS. 1 to 12 are bar graphs depicting the characterization of various immune cell populations in mice bearing cardiac allografts. In each graph, the subject cells were obtained from each of five different groups of graft-bearing mice, the individual groups treated as follows: (Group 1) a control antibody that does not bind to CD200; (Group 2) an anti-CD200 antibody; (Group 3) cyclosporine A; (Group 4) a combination of the control antibody and cyclosporine A; and (Group 5) a combination of the anti-CD200 antibody and cyclosporine A. (Additional details of the treatment regimen for each group are provided in Example 5 below.) The Y axis of FIGS. 1 to 4 is in units of mean fluorescence intensity (MFI), which is a measure of the relative expression level of a given antigen (e.g., CD40 (FIG. 1), MHC class II (FIG. 2), CD80 (FIG. 3), and IL-12 (FIG. 4)) on a per cell basis. The Y axis of FIGS. 5 to 12 is in percentage of a given cell type in a population of isolated splenocytes.

The results of this analysis, shown in FIG. 1 and Table 7A, are provided in units of mean fluorescence intensity (MFI), which is a measure of the relative level of CD40 expression per cell. The average level of expression by cells from the three animals is provided in the Table as well as the standard deviation within an experimental group. A T test was also performed on the data set to determine whether the results are statistically significant.

TABLE 7A

CD40 Expression by CD11$^+$ CD49b$^-$ Dendritic cells

| | Treatment | | | | |
|---|---|---|---|---|---|
| | Group 1 Antibody 2 | Group 2 Antibody 1 | Group 3 CsA | Group 4 Antibody 2 + CsA | Group 5 Antibody 1 + CsA |
| N1 | 10.5 | 10.1 | 8.03 | 10.3 | 7.77 |
| N2 | 12.4 | 17.9 | 15.3 | 14.9 | 8.2 |
| N3 | 13.3 | 12.9 | 10.5 | 13.7 | 9.4 |
| Mean | 12.0667 | 13.6333 | 11.2767 | 12.9667 | 8.45667 |
| Stdev | 1.42945 | 3.95137 | 3.69671 | 2.38607 | 0.84477 |

"Stdev" refers to standard deviation.

As shown in FIG. 1 and Table 7A, administration of Antibody 2 (the control antibody) alone to cardiac-allograft bearing mice resulted in an average MFI for CD40 of 12.067. In contrast, administration of Antibody 1 (an anti-CD200 antibody that lacks effector function) along with CsA to such mice resulted in a statistically significant decrease in CD40 expression by CD11$^+$ (gated on CD49b$^-$) cells. This reduction in expression was correlated with a prolonging of graft survival in Antibody 1+CsA-treated mice (see Example 1). A decrease in CD40 expression was not observed, however, in cells of this type obtained from animals treated with Antibody 1 alone, CsA alone, or with a combination of Antibody 2 and CsA. These results indicate that a reduction in CD40 expression is associated with increased allograft survival in cardiac allograft-bearing mammals treated with an anti-CD200 antibody and CsA.

MHC Class II Expression by CD11$^+$ CD49b$^-$ Dendritic Cells

Using flow cytometry, the level of MHC class II expression by CD11$^+$ CD49b$^-$ dendritic cells obtained from each mouse (N1, N2, and N3) was evaluated. MHC class II molecules are found on a variety of APCs and are involved in antigen recognition and antigen-specific activation of immune cells. While not being bound to any particular theory or mechanism of action, a reduction in the level of MHC class II by APCs, such as dendritic cells, and thus a reduction in APC activation, would likely inhibit or reduce an anti-graft immune response in a recipient mammal.

Figure 2:
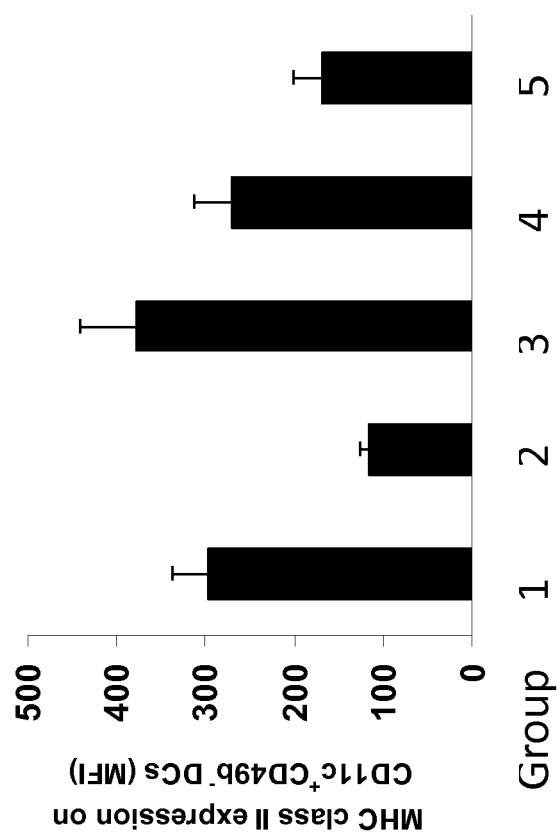

The results of this analysis, shown in FIG. 2 and Table 7B, are provided in MFI units as a measure of the relative level of MHC class II expression per cell. The average level of expression by cells from the three animals is provided in the Table as well as the standard deviation within an experimental group. A T test was also performed on the data set to determine whether the results are statistically significant.

TABLE 7B

MHC class II Expression by CD11$^+$ CD49b$^-$ Dendritic cells

| | Treatment | | | | |
|---|---|---|---|---|---|
| | Group 1 Antibody 2 | Group 2 Antibody 1 | Group 3 CsA | Group 4 Antibody 2 + CsA | Group 5 Antibody 1 + CsA |
| N1 | 260 | 127 | 311 | 238 | 146 |
| N2 | 291 | 114 | 382 | 252 | 157 |
| N3 | 340 | 108 | 439 | 319 | 205 |
| Mean | 297 | 116.333 | 377.333 | 269.667 | 169.333 |
| Stdev | 40.3361 | 9.71253 | 64.1275 | 43.2936 | 31.3741 |

"Stdev" refers to standard deviation.

As shown in FIG. 2 and Table 7B, administration of Antibody 2 (the control antibody) alone to cardiac-allograft bearing mice resulted in an average MFI for MHC class II of 297. In contrast, administration of an anti-CD200 antibody (Antibody 1) results in a statistically significant decrease in the MHC class II expression by cells of the same histological type (average MFI of 116.33). Similarly, administration of the anti-CD200 antibody along with CsA resulted in a statistically significant decrease in MHC class II expression in this cell type. A reduction in MHC class II expression was not observed, however, in mice treated with CsA alone, or with CsA and the control antibody (Antibody 2). These results indicate that a reduction in MHC class II expression is associated with increased allograft survival in cardiac allograft-bearing mammals treated with an anti-CD200 antibody and CsA.

CD80 Expression by CD11$^+$ CD49b$^-$ Dendritic Cells

Using flow cytometry, the level of CD80 expression by CD11$^+$ CD49b$^-$ dendritic cells obtained from each mouse (N1, N2, and N3) was evaluated. CD80 (also referred to as B7-1) is expressed by a variety of APCs and provides a co-stimulatory signal necessary for activation and survival of T cells. While not being bound to any particular theory or mechanism of action, a reduction in the level of CD80 by APCs, such as dendritic cells, and thus a reduction in T cell activation, would likely inhibit or reduce an anti-graft immune response in a recipient mammal.

The results of this analysis are provided in FIG. 3 and Table 7C, being reported as a measure of the relative level of CD80 expression per cell (MFI). The average level of expression by cells from the three animals is provided in the Table as well as the standard deviation within an experimental group. A T test was also performed on the data set to determine whether the results are statistically significant.

TABLE 7C

CD80 Expression by CD11+ CD49b− Dendritic cells

| | Treatment | | | | |
|---|---|---|---|---|---|
| | Group 1 Antibody 2 | Group 2 Antibody 1 | Group 3 CsA | Group 4 Antibody 2 + CsA | Group 5 Antibody 1 + CsA |
| N1 | 120 | 50.1 | 45.4 | 99.5 | 37.9 |
| N2 | 109.2 | 48.4 | 49.9 | 82.3 | 31.4 |
| N3 | 106.7 | 53.9 | 47.5 | 97.6 | 32.5 |
| Mean | 111.967 | 50.8 | 47.6 | 93.1333 | 33.9333 |
| Stdev | 7.06847 | 2.81603 | 2.2517 | 9.42992 | 3.47898 |

"Stdev" refers to standard deviation.

As shown in FIG. 3 and Table 7C, administration of Antibody 2 (the control antibody) alone to cardiac-allograft bearing mice resulted in an average MFI for CD80 of approximately 112. In contrast, administration of an anti-CD200 antibody (Antibody 1) or CsA results in a statistically significant decrease in CD80 expression by cells of the same histological type (average MFI of 50.8 and 47.6 for Antibody 1 and CsA, respectively). Similarly, administration of the anti-CD200 antibody along with CsA resulted in a statistically significant decrease in CD80 expression in this cell type. A reduction in CD80 expression was not observed, however, in mice treated with CsA and the control antibody (Antibody 2). These results indicate that a reduction in CD80 expression by CD11+CD49b− dendritic cells is associated with increased allograft survival in cardiac allograft-bearing mammals treated with an anti-CD200 antibody and CsA.

IL-12 Expression by CD11+ CD49b− Dendritic Cells

Using flow cytometry, the level of IL-12 expression by CD11+CD49b− cells (dendritic cells) obtained from each mouse (N1, N2, and N3) was evaluated. The results of this analysis are provided in FIG. 4 and Table 7D, being reported as a measure of the relative level of IL-12 expression per cell (MFI). The average level of expression by cells from the three animals is provided in the Table as well as the standard deviation within an experimental group. A T test was also performed on the data set to determine whether the results are statistically significant.

TABLE 7D

IL-12 Expression by CD11+ CD49b− Dendritic cells

| | Treatment | | | | |
|---|---|---|---|---|---|
| | Group 1 Antibody 2 | Group 2 Antibody 1 | Group 3 CsA | Group 4 Antibody 2 + CsA | Group 5 Antibody 1 + CsA |
| N1 | 4.08 | 8.57 | 4.78 | 5.94 | 9.26 |
| N2 | 5.97 | 6.71 | 6.26 | 6.04 | 8.46 |
| N3 | 5.66 | 6.37 | 6.61 | 6.21 | 9.45 |
| Mean | 5.23667 | 7.21667 | 5.88333 | 6.06333 | 9.05667 |
| Stdev | 1.01362 | 1.18429 | 0.97141 | 0.1365 | 0.52539 |

"Stdev" refers to standard deviation.

Figure 4:
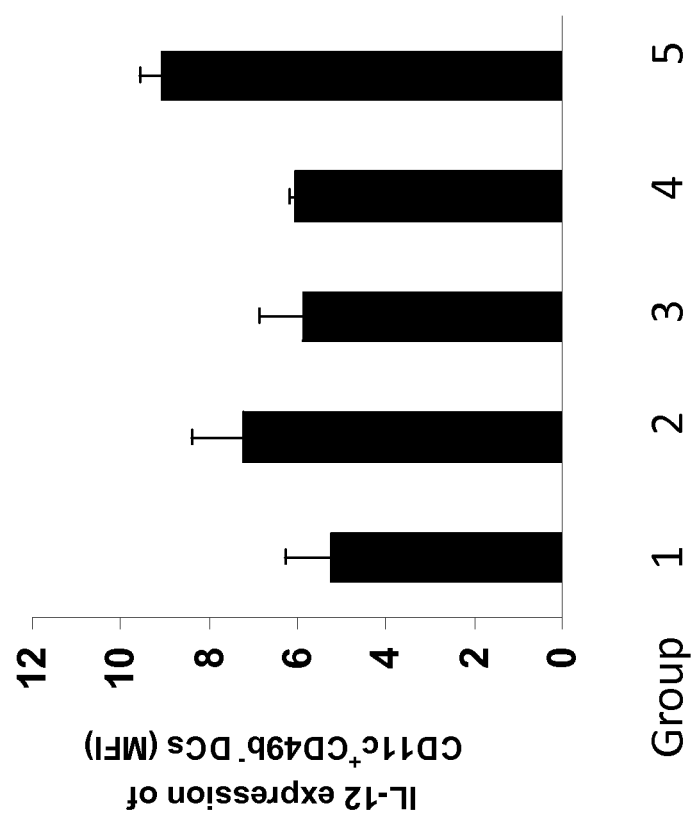

As shown in FIG. 4 and Table 7D, administration of Antibody 2 (the control antibody) alone to cardiac-allograft bearing mice resulted in an average MFI for IL-12 of approximately 5.24. In contrast, administration of an anti-CD200 antibody (Antibody 1) or anti-CD200 antibody plus CsA results in a statistically significant increase in IL-12 expression by cells of the same histological type. Similarly, administration of the anti-CD200 antibody along with CsA resulted in a statistically significant increase in IL-12 expression in this cell type. An increase in IL-12 expression was not observed, however, in mice treated with CsA alone or with CsA and the control antibody (Antibody 2). These results indicate that an increase in IL-12 expression by CD11+CD49b− dendritic cells is associated with increased allograft survival in cardiac allograft-bearing mammals treated with an anti-CD200 antibody or an anti-CD200 antibody in combination with CsA.

CD4+CD25+FoxP3+ Cells

Using flow cytometry, the percentage of CD4+CD25+FoxP3+ cells, within a total population of splenocytes obtained from each mouse (N1, N2, and N3), was evaluated. CD4+CD25+FoxP3+ cells are regulatory T (Treg) cells, a subset of T cells with the ability to suppress harmful immunological reactions to self and foreign antigens. While not being bound to any particular theory or mechanism of action, an increase in the concentration of such cells would likely inhibit or reduce an anti-graft immune response in a recipient mammal.

Figure 5:
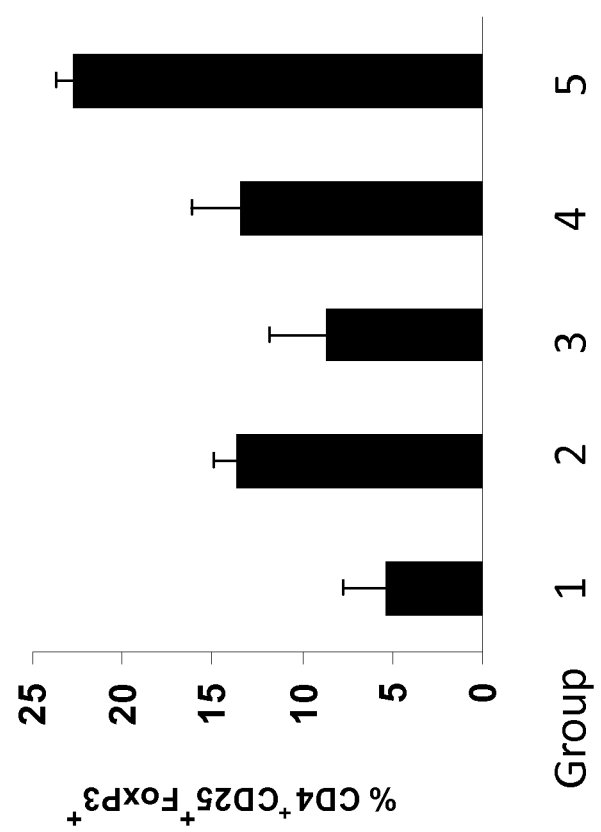

The results of this analysis are provided in FIG. 5 and Table 7E, being reported as a measure of the percentage of CD4+CD25+FoxP3+ cells within a population of CD3+ T cells isolated from the spleen of the mice. The average percentage of these cells from each of the three animals is provided in the Table as well as the standard deviation within each experimental group. A T test was also performed on the data set to determine whether the results are statistically significant.

TABLE 7E

Percentage of CD4+CD25+FoxP3+ cells

| | Treatment | | | | |
|---|---|---|---|---|---|
| | Group 1 Antibody 2 | Group 2 Antibody 1 | Group 3 CsA | Group 4 Antibody 2 + CsA | Group 5 Antibody 1 + CsA |
| N1 | 6.3 | 13.3 | 12.1 | 10.3 | 22.2 |
| N2 | 2.49 | 15.1 | 5.71 | 15.3 | 22 |
| N3 | 7.01 | 12.4 | 8.2 | 14.7 | 23.81 |
| Mean | 5.26667 | 13.6 | 8.67 | 13.4333 | 22.67 |
| Stdev | 2.43073 | 1.37477 | 3.22082 | 2.73008 | 0.99232 |

"Stdev" refers to standard deviation.

As shown in FIG. 5 and Table 7E, administration of Antibody 2 (the control antibody) alone to cardiac-allograft bearing mice resulted in an average percentage of CD4+CD25+FoxP3+ cells of approximately 5.27%. In contrast, administration of an anti-CD200 antibody (Antibody 1) results in a statistically significant increase in the percentage of cells of the same histological type (13.6%). Similarly, administration of the anti-CD200 antibody along with CsA resulted in a statistically significant increase in the percentage of this cell type (22.7%). An increase in percentage of CD4+CD25+FoxP3+ cells was, however, also observed in mice treated with CsA and the control antibody (Antibody 2), but not with CsA alone. These results indicate that an increase in the percentage of Tregs is associated with increased allograft survival in cardiac allograft-bearing mammals treated with an anti-CD200 antibody or an anti-CD200 antibody in combination with CsA.

Gr-1+CD11b+CD45+ Cells

Using flow cytometry, the percentage of Gr-1+CD11b+CD45+ cells, within a total population of splenocytes obtained from each mouse (N1, N2, and N3), was evaluated. Gr-1+CD11b+CD45+ cells, are myeloid cells, also referred to as myeloid-derived suppressor cells or (MDSCs) [Gabrilovich et al. (2007) *Cancer Res* 67(1):425-426], which are a heterogeneous cellular population containing macrophages, granulocytes, immature dendritic cells, and early myeloid precursors. While not being bound to any particular theory or mechanism of action, an increase in the concentration of such suppressor cells would likely inhibit or reduce an anti-graft immune response in a recipient mammal.

Figure 6:
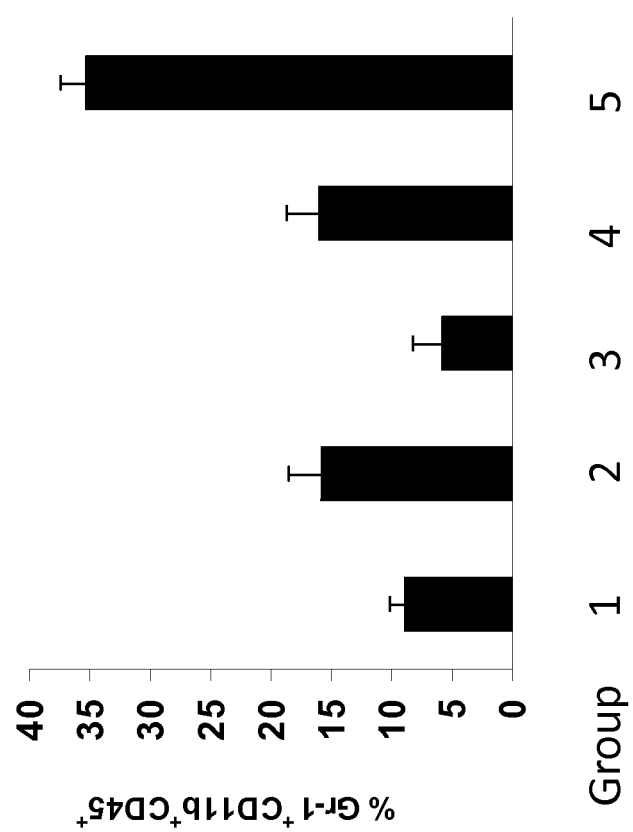

The results of this analysis are provided in FIG. 6 and Table 7F, being reported as a measure of the percentage Gr-1$^+$CD11b$^+$CD45$^+$ cells within a population of lymphocytes isolated from the spleen of the mice. The average percentage of these cells from each of the three animals is provided in the Table as well as the standard deviation within each experimental group. A T test was also performed on the data set to determine whether the results are statistically significant.

TABLE 7F

Percentage of Gr-1$^+$CD11b$^+$CD45$^+$ cells

| | Treatment | | | | |
|---|---|---|---|---|---|
| | Group 1 Antibody 2 | Group 2 Antibody 1 | Group 3 CsA | Group 4 Antibody 2 + CsA | Group 5 Antibody 1 + CsA |
| N1 | 8.46 | 16.8 | 3.71 | 18.6 | 37.7 |
| N2 | 10.23 | 12.7 | 5.5 | 16.1 | 34.28 |
| N3 | 7.75 | 17.9 | 8.4 | 13.32 | 34.1 |
| Mean | 8.8133 | 15.8 | 5.87 | 16.0067 | 35.36 |
| Stdev | 1.2772 | 2.74044 | 2.36679 | 2.64124 | 2.0285 |

"Stdev" refers to standard deviation.

As shown in FIG. 6 and Table 7F, administration of Antibody 2 (the control antibody) alone to cardiac-allograft bearing mice resulted in an average percentage of Gr-1$^+$CD11b$^+$CD45$^+$ cells of approximately 8.81%. In contrast, administration of an anti-CD200 antibody (Antibody 1) results in a statistically significant increase in the percentage of cells of the same histological type (15.8%). Similarly, administration of the anti-CD200 antibody along with CsA resulted in a statistically significant increase in the percentage of this cell type (35.36%). An increase in percentage of CD4$^+$CD25$^+$FoxP3$^+$ cells was, however, also observed in mice treated with CsA plus the control antibody (Antibody 2), but not with CsA alone. These results indicate that an increase in the percentage of Gr-1$^+$CD11b$^+$CD45$^+$ myeloid suppressor cells is associated with increased allograft survival in cardiac allograft-bearing mammals treated with an anti-CD200 antibody or an anti-CD200 antibody in combination with CsA.

F4/80$^+$CD45$^+$ Cells

Using flow cytometry, the percentage of F4/80$^+$CD45$^+$ cells, within a total population of splenocytes obtained from each mouse (N1, N2, and N3), was evaluated. F4/80$^+$CD45$^+$ cells, are immune effector cells, which are a heterogeneous cellular population containing macrophages, granulocytes, immature dendritic cells, and early myeloid precursors. While not being bound to any particular theory or mechanism of action, a decrease in the concentration of such cells would likely inhibit or reduce an anti-graft immune response in a recipient mammal.

Figure 7:
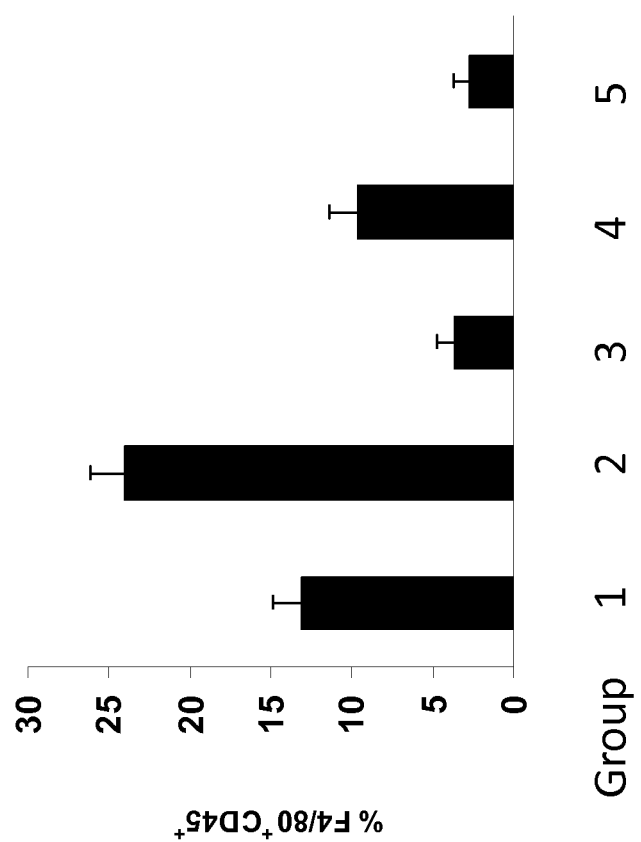

The results of this analysis are provided in FIG. 7 and Table 7G, being reported as a measure of the percentage F4/80$^+$CD45$^+$ cells within a population of lymphocytes isolated from the spleen of the mice. The average percentage of these cells from each of the three animals is provided in the Table as well as the standard deviation within each experimental group. A T test was also performed on the data set to determine whether the results are statistically significant.

TABLE 7G

Percentage of F4/80$^+$CD45$^+$ cells

| | Treatment | | | | |
|---|---|---|---|---|---|
| | Group 1 Antibody 2 | Group 2 Antibody 1 | Group 3 CsA | Group 4 Antibody 2 + CsA | Group 5 Antibody 1 + CsA |
| N1 | 11.8 | 21.88 | 2.93 | 8.44 | 2.46 |
| N2 | 15.2 | 24.2 | 4.88 | 11.6 | 3.8 |
| N3 | 12.21 | 26.1 | 3.01 | 8.83 | 1.81 |
| Mean | 13.07 | 24.06 | 3.60667 | 9.62333 | 2.69 |
| Stdev | 1.85599 | 2.11348 | 1.10346 | 1.72291 | 1.01474 |

"Stdev" refers to standard deviation.

As shown in FIG. 7 and Table 7G, administration of Antibody 2 (the control antibody) alone to cardiac-allograft bearing mice resulted in an average percentage of F4/80$^+$CD45$^+$ cells of approximately 13.07%. In contrast, administration of an anti-CD200 antibody (Antibody 1) results in a statistically significant increase in the percentage of cells of the same histological type (24.06%). Administration of the anti-CD200 antibody along with CsA resulted in a statistically significant decrease in the percentage of this cell type (2.69%). A decrease in the percentage of F4/80$^+$CD45$^+$ cells was, however, also observed in mice treated with CsA plus the control antibody (Antibody 2), and also with CsA alone. These results indicate that a decrease in the percentage of F4/80$^+$CD45$^+$ cells is associated with increased allograft survival in cardiac allograft-bearing mammals treated with an anti-CD200 antibody in combination with CsA.

CD3$^+$CD25$^+$ Cells

Using flow cytometry, the percentage of CD3$^+$CD25$^+$ cells, within a total population of splenocytes obtained from each mouse (N1, N2, and N3), was evaluated. CD3$^+$CD25$^+$ cells are an activated T cell subset. While not being bound to any particular theory or mechanism of action, a decrease in the concentration of such cells would likely inhibit or reduce an anti-graft immune response in a recipient mammal.

Figure 8:
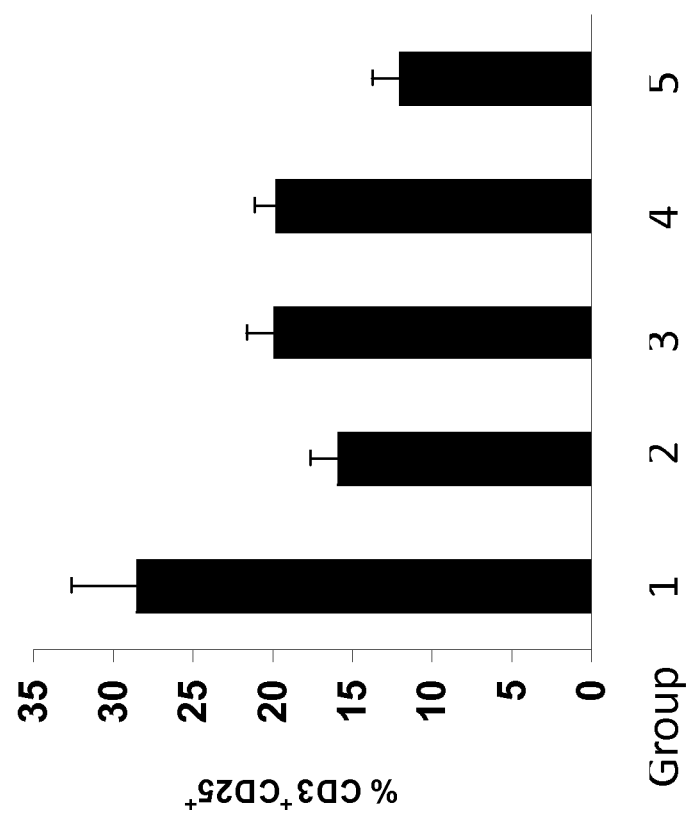

The results of this analysis are provided in FIG. 8 and Table 7H, being reported as a measure of the percentage CD3$^+$CD25$^+$ cells within a population of lymphocytes isolated from the spleen of the mice. The average percentage of these cells from each of the three animals is provided in the Table as well as the standard deviation within each experimental group. A T test was also performed on the data set to determine whether the results are statistically significant.

TABLE 7H

Percentage CD3$^+$CD25$^+$ cells

| | Treatment | | | | |
|---|---|---|---|---|---|
| | Group 1 Antibody 2 | Group 2 Antibody 1 | Group 3 CsA | Group 4 Antibody 2 + CsA | Group 5 Antibody 1 + CsA |
| N1 | 23.7 | 17.8 | 20.5 | 20.4 | 10.3 |
| N2 | 30.2 | 15.4 | 21.2 | 18.2 | 12 |
| N3 | 31.5 | 14.3 | 17.8 | 20.7 | 13.7 |
| Mean | 28.4667 | 15.8333 | 19.8333 | 19.7667 | 12 |
| Stdev | 4.17892 | 1.78979 | 1.79536 | 1.365 | 1.7 |

"Stdev" refers to standard deviation.

As shown in FIG. 8 and Table 7H, administration of Antibody 2 (the control antibody) alone to cardiac-allograft bearing mice resulted in an average percentage of CD3$^+$ CD25+ cells of approximately 28.47%. In contrast, administration of an anti-CD200 antibody (Antibody 1) results in a statistically significant decrease in the percentage of cells of the same histological type (15.83%). Administration of the anti-CD200 antibody along with CsA resulted in a statistically significant decrease in the percentage of this cell type (12%). A decrease in the percentage of CD3+CD25+ cells was, however, also observed in mice treated with CsA and the control antibody (Antibody 2) and in mice treated with CsA alone. These results indicate that a decrease in the percentage of CD3+CD25+ cells is associated with increased allograft survival in cardiac allograft-bearing mammals treated with an anti-CD200 antibody in combination with CsA.

CD3+CD8+ Cells

Using flow cytometry, the percentage of CD3+CD8+ cells, within a total population of splenocytes obtained from each mouse (N1, N2, and N3), was evaluated. CD3+CD8+ cells are cytotoxic T cells. While not being bound to any particular theory or mechanism of action, a decrease in the concentration of such cells would likely inhibit or reduce an anti-graft immune response in a recipient mammal.

Figure 9:
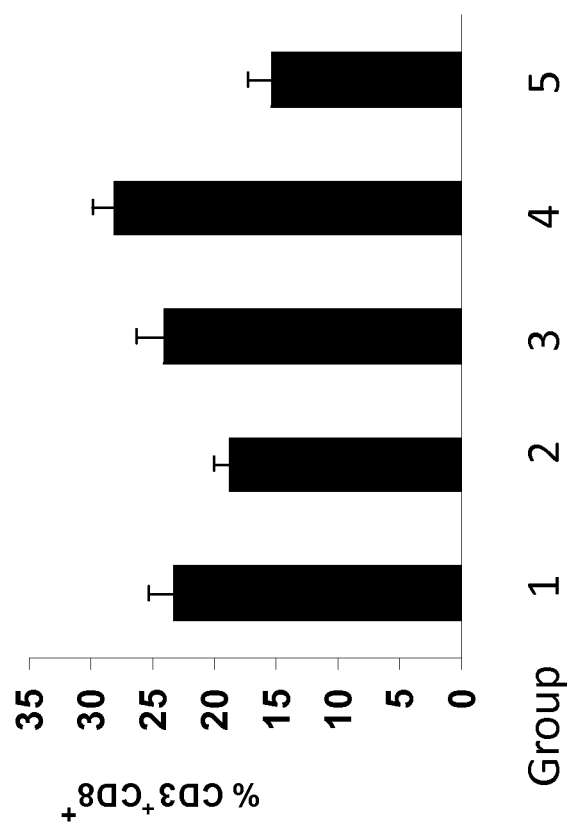

The results of this analysis are provided in FIG. 9 and Table 7I, being reported as a measure of the percentage CD3+CD8+ cells within a population of lymphocytes isolated from the spleen of the mice. The average percentage of these cells from each of the three animals is provided in the Table as well as the standard deviation within each experimental group. A T test was also performed on the data set to determine whether the results are statistically significant.

TABLE 7I

Percentage CD3+CD8+ cells

| | Treatment | | | | |
|---|---|---|---|---|---|
| | Group 1 Antibody 2 | Group 2 Antibody 1 | Group 3 CsA | Group 4 Antibody 2 + CsA | Group 5 Antibody 1 + CsA |
| N1 | 21.5 | 18.9 | 26.3 | 29.9 | 15.2 |
| N2 | 25.7 | 19.9 | 21.8 | 28.1 | 13.5 |
| N3 | 22.3 | 17.1 | 24.2 | 26.3 | 17.4 |
| Mean | 23.1667 | 18.6333 | 24.1 | 28.1 | 15.3667 |
| Stdev | 2.2301 | 1.41892 | 2.25167 | 1.8 | 1.95533 |

"Stdev" refers to standard deviation.

As shown in FIG. 9 and Table 7I, administration of Antibody 2 (the control antibody) alone to cardiac-allograft bearing mice resulted in an average percentage of CD3+ CD8+ cells of approximately 23.17%. In contrast, administration of an anti-CD200 antibody (Antibody 1) results in a statistically significant decrease in the percentage of cells of the same histological type (18.6%). Administration of the anti-CD200 antibody along with CsA resulted in a statistically significant decrease in the percentage of this cell type (15.4%). These results indicate that a decrease in the percentage of CD3+CD8+ cells is associated with increased allograft survival in cardiac allograft-bearing mammals treated with an anti-CD200 antibody or an anti-CD200 antibody in combination with CsA.

CD3+CD4+ Cells

Using flow cytometry, the percentage of CD3+CD4+ cells, within a total population of splenocytes obtained from each mouse (N1, N2, and N3), was evaluated. CD3+CD4+ cells are helper T cells. While not being bound to any particular theory or mechanism of action, a decrease in the concentration of such cells would likely inhibit or reduce an anti-graft immune response in a recipient mammal.

Figure 10:
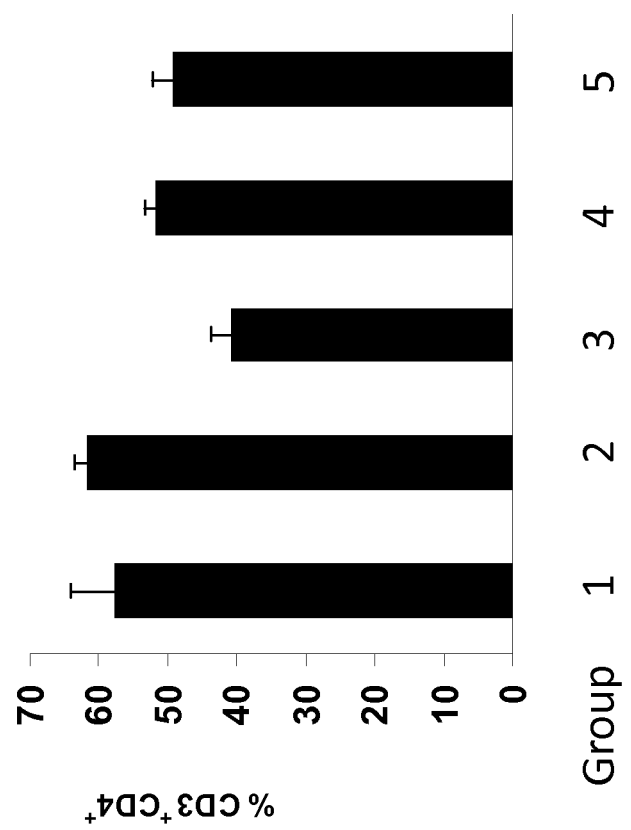

The results of this analysis are provided in FIG. 10 and Table 7J, being reported as a measure of the percentage CD3+CD4+ cells within a population of lymphocytes isolated from the spleen of the mice. The average percentage of these cells from each of the three animals is provided in the Table as well as the standard deviation within each experimental group. A T test was also performed on the data set to determine whether the results are statistically significant.

TABLE 7J

Percentage CD3+CD4+ cells

| | Treatment | | | | |
|---|---|---|---|---|---|
| | Group 1 Antibody 2 | Group 2 Antibody 1 | Group 3 CsA | Group 4 Antibody 2 + CsA | Group 5 Antibody 1 + CsA |
| N1 | 52.9 | 63.3 | 38.4 | 50.2 | 51.2 |
| N2 | 65 | 61.7 | 39.5 | 53.5 | 45.8 |
| N3 | 54.6 | 59.2 | 44.1 | 51 | 50.6 |
| Mean | 57.5 | 61.4 | 40.6667 | 51.5667 | 49.2 |
| Stdev | 6.55057 | 2.0664 | 3.02379 | 1.72143 | 2.95973 |

"Stdev" refers to standard deviation.

As shown in FIG. 10 and Table 7J, administration of Antibody 2 (the control antibody) alone to cardiac-allograft bearing mice resulted in an average percentage of CD3+ CD4+ cells of approximately 57.5%. Administration of the anti-CD200 antibody along with CsA resulted in a decrease in the percentage of this cell type (49.2%). Administration of the anti-CD200 antibody alone resulted in a slight increase in the percentage of the T cells.

CD3+CD200R+ Cells

Using flow cytometry, the percentage of CD3+CD200R+ cells, within a total population of splenocytes obtained from each mouse (N1, N2, and N3), was evaluated. CD3+ CD200R+ cells are a CD200R+ subset of T cells. The results of this analysis are provided in FIG. 11 and Table 7K, being reported as a measure of the percentage CD3+CD200R+ cells within a population of lymphocytes isolated from the spleen of the mice. The average percentage of these cells from each of the three animals is provided in the Table as well as the standard deviation within each experimental group. A T test was also performed on the data set to determine whether the results are statistically significant.

TABLE 7K

Percentage CD3+CD200R+ cells

| | Treatment | | | | |
|---|---|---|---|---|---|
| | Group 1 Antibody 2 | Group 2 Antibody 1 | Group 3 CsA | Group 4 Antibody 2 + CsA | Group 5 Antibody 1 + CsA |
| N1 | 19.8 | 23.3 | 14.1 | 14.9 | 21.8 |
| N2 | 16.82 | 22.3 | 12.8 | 10.8 | 19.7 |
| N3 | 16.8 | 28.8 | 19.2 | 10.9 | 18.1 |
| Mean | 17.8067 | 24.8 | 15.3667 | 12.2 | 19.8667 |
| Stdev | 1.72631 | 3.5 | 3.3828 | 2.3388 | 1.85562 |

"Stdev" refers to standard deviation.

Figure 11:
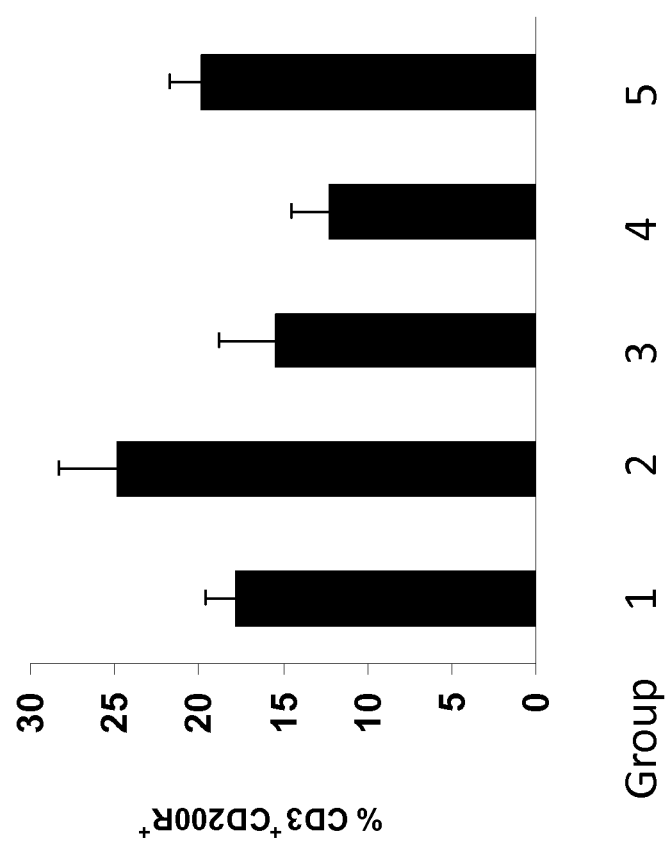

As shown in FIG. 11 and Table 7K, administration of Antibody 2 (the control antibody) alone to cardiac-allograft bearing mice resulted in an average percentage of CD3+ CD200R+ cells of approximately 17.8%. In contrast, administration of an anti-CD200 antibody (Antibody 1) results in an increase in the percentage of cells of the same histological type (24.8%). Administration of the anti-CD200 antibody along with CsA resulted in a slight increase in the percentage of this cell type (19.87%).

CD19$^+$CD45$^+$ Cells

Using flow cytometry, the percentage of CD19$^+$CD45$^+$ cells, within a total population of splenocytes obtained from each mouse (N1, N2, and N3), was evaluated. CD19$^+$CD45$^+$ cells are a CD45$^+$ subset of B cells. The results of this analysis are provided in FIG. 12 and Table 7L, being reported as a measure of the percentage CD19$^+$CD45$^+$ cells within a population of lymphocytes isolated from the spleen of the mice. The average percentage of these cells from each of the three animals is provided in the Table as well as the standard deviation within each experimental group. A T test was also performed on the data set to determine whether the results are statistically significant.

TABLE 7L

Percentage CD19$^+$CD45$^+$ cells

| | Treatment | | | | |
|---|---|---|---|---|---|
| | Group 1 Antibody 4 | Group 2 Antibody 3 | Group 3 CsA | Group 4 Antibody 4 + CsA | Group 5 Antibody 3 + CsA |
| N1 | 23.7 | 17.8 | 20.5 | 20.4 | 10.3 |
| N2 | 30.2 | 15.4 | 21.2 | 18.2 | 12 |
| N3 | 31.5 | 14.3 | 17.8 | 20.7 | 13.7 |
| Mean | 28.4667 | 15.8333 | 19.8333 | 19.7667 | 12 |
| Stdev | 4.17892 | 1.78979 | 1.79536 | 1.36504 | 1.7 |

"Stdev" refers to standard deviation.

Figure 12:
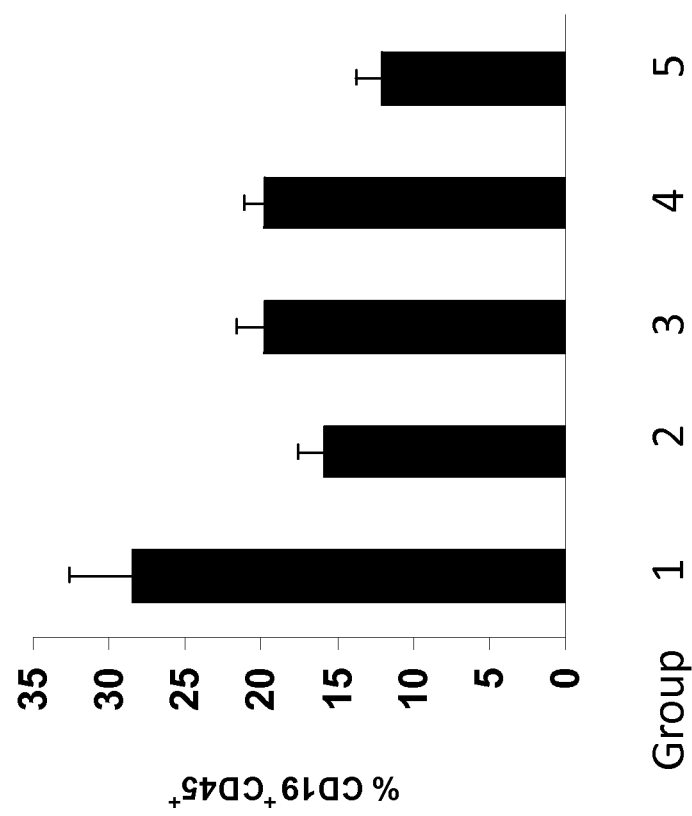

As shown in FIG. 12 and Table 7L, administration of Antibody 2 (the control antibody) alone to cardiac-allograft bearing mice resulted in an average percentage of CD19$^+$CD45$^+$ cells of approximately 28.4667%. In contrast, administration of an anti-CD200 antibody (Antibody 1) results in a statistically significant decrease in the percentage of cells of the same histological type (15.8333%). Administration of the anti-CD200 antibody along with CsA resulted in a statistically significant increase in the percentage of this cell type (12%). These results indicate that a decrease in the percentage of CD19$^+$CD45$^+$ cells is associated with increased allograft survival in cardiac allograft-bearing mammals treated with an anti-CD200 antibody or an anti-CD200 antibody in combination with CsA.

Example 6

Efficacy of Combination Therapies for Prolonging Allograft Survival

As described in Example 4, the duration of treatment with, or the dose level of, an immunosuppressive agent (e.g., a calcineurin inhibitor such as FK-506 or CsA) required to prolong the survival of an allograft in a recipient mammal can be reduced by administration of an anti-CD200 antibody to the recipient mammal. An experiment was performed to determine the therapeutic effect of an anti-CD200 antibody used in combination with a calcineurin inhibitor and a mycophenolate compound.

As described in Example 3, these studies examined graft survival in a C57BL/6 to BALB/c fully MHC-mismatched mouse heart transplantation model. Each experimental group included five (5) animals. The five experimental groups were treated as follows:

Group 1: graft-bearing mice were orally administered FK-506 at a dose of 16 mg/kg per day for the duration of the study;

Group 2: graft-bearing mice were subcutaneously administered an anti-CD200 antibody (Antibody 1, Example 3) at a dose of 100 μg each day for 14 days and, concurrently, mycophenolate mofetil at a dose of 80 mg/kg per day;

Group 3: graft-bearing mice were subcutaneously administered a control antibody that does not bind to CD200 (Antibody 2, Example 3) at a dose of 100 μg each day for 14 days and, concurrently, mycophenolate mofetil at a dose of 80 mg/kg per day;

Group 4: graft-bearing mice were subcutaneously administered an anti-CD200 antibody (Antibody 1, Example 3) at a dose of 100 μg each day for 14 days and, concurrently, (a) orally administered mycophenolate mofetil at a dose of 80 mg/kg per day and (b) orally administered FK-506 at a dose of 16 mg/kg per day for 28 days; and Group 5: graft-bearing mice were subcutaneously administered the control antibody (Antibody 2, Example 3) at a dose of 100 μg each day for 14 days and, concurrently, (a) orally administered mycophenolate mofetil at a dose of 80 mg/kg per day and (b) orally administered FK-506 at a dose of 16 mg/kg per day for 28 days.

The results of this experiment are set forth in Table 8.

TABLE 8

| Group | Mean Survival (days) |
|---|---|
| 1 | 25.2 ± 1.5 |
| 2 | 63.4 ± 1.1 |
| 3 | 21 ± 2.6 |
| 4 | >100 |
| 5 | 39.2 ± 3.9 |

A numeric value annotated with a ">" refers to a subject mouse that continues to survive beyond the number of days indicated.

As shown in Table 8, administration of a high dose of the calcineurin inhibitor FK-506 for the duration of the study (until failure of the cardiac graft) only resulted in a mean graft survival of approximately 25.2 days (Group 1). Co-administration of an anti-CD200 antibody with mycophenolate mofetil resulted in a graft survival of approximately 63.4 days (Group 2). However, the triple therapy of an anti-CD200 antibody, mycophenolate mofetil, and FK-506 resulted in indefinite graft survival (in this experiment, until sacrifice at 100 days). In contrast, a triple therapy of mycophenolate mofetil, FK-506, and the control antibody resulted in a graft survival of approximately 39.2 days (Group 5). The increased organ survival in recipient mammals of Group 4 was statistically significant as compared to the survival of grafts in Group 2 and Group 5 mice. The mean survival of the grafts of Group 2 mice was statistically significant as compared to the survival of Group 1 and Group 3 mouse allografts. Notably, administration of the anti-CD200 antibody allows for a reduction in the duration of treatment required with FK-506 (from daily for the entire study to just 28 days). These results indicate that anti-CD200 antibody is useful for reducing the duration of treatment with a calcineurin inhibitor required for prolonging graft survival (see also Example 4(2)). The results also indicate that the particular therapy combination of an anti-CD200 antibody, a mycophenolate compound (or a compound possessing similar functional properties), and a calcineurin inhibitor is useful for prolonging the survival of an allograft organ in a recipient mammal.

An experiment was performed to determine the therapeutic effect of an anti-CD200 antibody used in combination with the mTOR inhibitor rapamycin.

As described in Example 3, these studies examined graft survival in a C57BL/6 to BALB/c fully MHC-mismatched mouse heart transplantation model. Each experimental group included five (5) animals. The three experimental groups were treated as follows, with treatment beginning at the time of transplantation:

Group 1: graft-bearing mice were orally administered rapamycin at a dose of 2 mg/kg per day for 14 days;

Group 2: graft-bearing mice were subcutaneously administered an anti-CD200 antibody (Antibody 1, Example 3) at a dose of 100 µg each day for 14 days and, concurrently, orally administered rapamycin at a dose of 2 mg/kg per day for 14 days; and Group 3: graft-bearing mice were subcutaneously administered a control antibody (Antibody 2, Example 3) at a dose of 100 µg each day for 14 days and, concurrently, orally administered rapamycin at a dose of 2 mg/kg per day for 14 days.

The results of this experiment are set forth in Table 9.

TABLE 9

| Group | Mean Survival (days) |
|---|---|
| 1 | 42.6 ± 4.7 |
| 2 | >100 |
| 3 | 36.2 ± 3.0 |

A numeric value annotated with a ">" refers to a subject mouse that continues to survive beyond the number of days indicated.

As shown in Table 9, administration of rapamycin alone, or in combination with a control antibody that does not bind to CD200, results in a mean graft survival in recipient animals of approximately 42.6 and 36.2 days, respectively. In contrast, co-administration of rapamycin with an anti-CD200 antibody (Group 2) resulted in indefinite allograft survival (which was statistically significant against the mean survival of grafts from Groups 1 and 3 mice). These results indicate that the particular combination of an anti-CD200 antibody and an mTOR inhibitor such as rapamycin is useful for prolonging the survival of an allograft organ in a recipient mammal.

Example 7

Effect of an Anti-CD200 Antibody on SHIP Expression by Splenocytes

An experiment was performed to evaluate the effect of anti-CD200 antibody treatment on SHIP expression by splenocytes in immunized mice. To induce an immune response, BALB/c mice were immunized with five (5) million splenocytes (red blood cell-depleted) isolated from B6 mice. Immediately following immunization, the mice were intraperitoneally administered Antibody 3 (Example 3 above) or Antibody 4 (Example 3 above) at a dose of 5 mg/kg/day. The mice were sacrificed on day 14.

The mouse spleens were removed and fixed with 4% paraformaldehyde (PFA) overnight at 4° C. The spleens were then washed with phosphate buffered saline (PBS) (pH 7.4) and then soaked in a 30% sucrose solution. The spleens were embedded in cryoprotective embedding medium (optimal cutting temperature (OCT) compound). 5-10 µm sections of the spleen were cut using a microtome-cryostat and placed on slides for air drying. The sections were then treated for 15 minutes with hydrogen peroxide followed by three washes with PBS.

The sections were then incubated for 30 minutes at room temperature with a blocking solution containing 3% bovine serum albumin, 3% normal rabbit serum, and 0.3% Triton X-100™ in PBS. Following the incubation, the sections were incubated with a goat polyclonal anti-SHIP1 antibody (Santa Cruz Biotechnology; M-14) at 1:100 in the blocking solution overnight at 4° C. After the overnight incubation, the sections were washed three times with PBS. Next, the slides were incubated with a biotinylated rabbit anti-goat antibody (Vectorstain ABC kit PK-1005) (1:1000 in blocking solution) for one hour at room temperature and then washed three times with PBS.

An avidin-peroxidase complex (1:200 in blocking solution) was contacted to the sections for one hour at room temperature and then the sections were again washed three times with PBS. The presence or amount of SHIP protein was visualized by contacting the sections with peroxidase substrate DAB for approximately five to ten minutes.

Figures 13A, 13B:
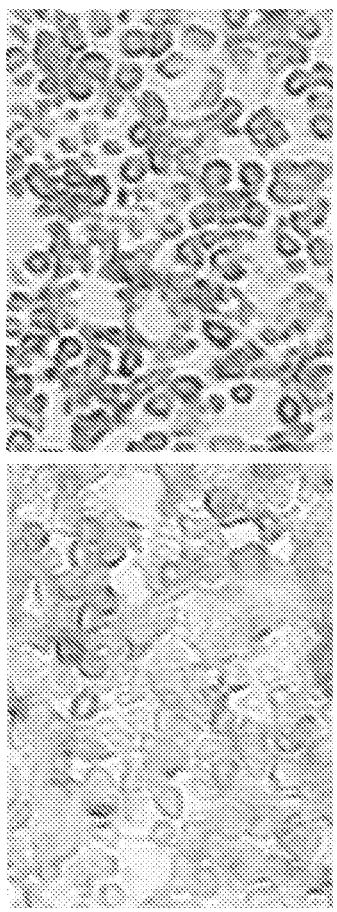
FIGS. 13A-13D show a series of photographs of immunostained spleen cells, which photographs depict the level of SHIP (SH2-containing Inositol-5'-Phosphatase) expression by the spleen cells. The spleen cells depicted in each photograph were isolated from BALB/c mice immunized with five (5) million allogeneic (B6 mouse) spleen cells (administered intraperitoneally). The immunized mice were further administered an anti-CD200 antibody (with effector function) [FIG. 13A] or a control antibody (with effector function) [FIG. 13B]. Following treatment, the spleens were harvested, fixed, subjected to immunohistochemistry (see below).
Figures 13C, 13D:
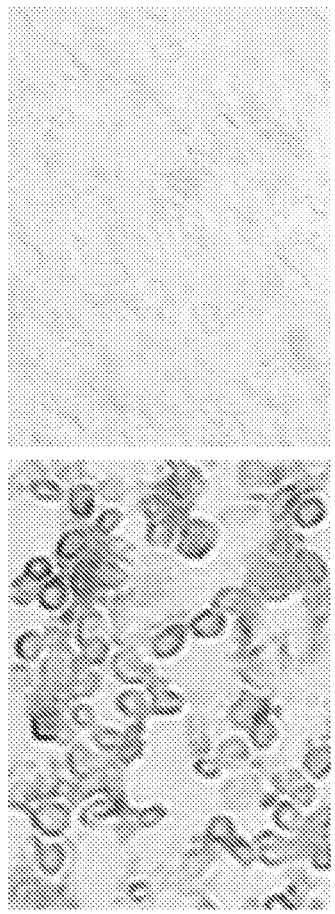

As shown in FIG. 13B, allogeneic cell immunization induced SHIP expression by the BALB/c spleen cells (see FIG. 13B) as compared to SHIP expression by spleen cells from non-immunized mice (see FIG. 13C). However, administration of Antibody 3 substantially reduced the expression of SHIP (see FIG. 13A). Each experimental group represented above included three mice. A representative photograph from each group is provided.

SHIP1 protein has been shown to bind to complexed FcγR2b in an SH2-dependent manner. See, e.g., Muraille et al. (2000) *Immunol Lett* 72(1):7-15. FcγR2b, which is expressed on immune cells of the spleen, can also complex with the IgG2a isotype Fc region present in Antibody 3 used in the above experiment. Thus, the inventors reasoned, it is possible that any effect on SHIP expression levels in splenocytes could be due, not to CD200 antagonism, but to the Fc region of the antibody administered to the mice. In other words, the inventors sought to determine whether the observed therapeutic effect of anti-CD200 antibody was target-mediated (i.e., via a CD200-SHIP pathway) or Fc-mediated (via an FcγR2b-SHIP pathway). Therefore, another experiment was performed to determine whether the antibody-dependent reduction in SHIP expression by spleen cells from immunized mice required the antibody's effector function. Wild type BALB/c mice as well as FcγR2b-deficient BALB/c mice were immunized with five (5) million B6 allogeneic spleen cells followed by administration of 100 µg of Antibody 3 or Antibody 4. One group of mice, "sham", received neither immunization nor antibody treatment. Each experimental group represented above included three mice.

Figure 14:
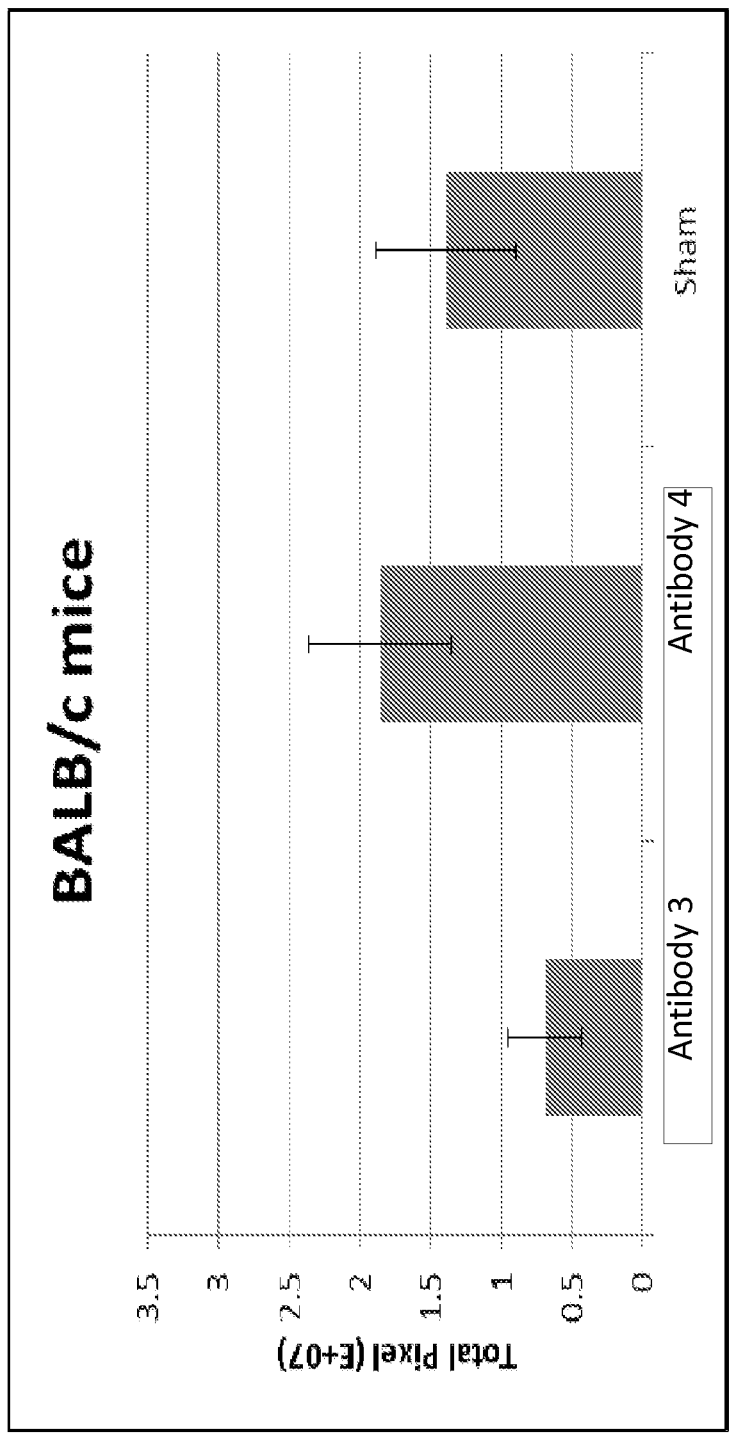
FIG. 14 is a bar graph depicting average relative SHIP expression by splenocytes obtained from BALB/c mice immunized with five (5) million B6 splenocytes as described above. The immunized mice were further administered an anti-CD200 antibody (with effector function) [Antibody 3; see Example 3] or a control antibody (with effector function) [Antibody 4; see Example 3]. One group of mice, "sham", received neither immunization nor antibody treatment. Each experimental group represented above included three mice. Following treatment, the spleens of the mice were harvested, fixed, and subjected to immunohistochemistry. The average relative expression from spleen cell sections was quantified using densitometry and is reported in total pixels (x E+7).
Figure 15:
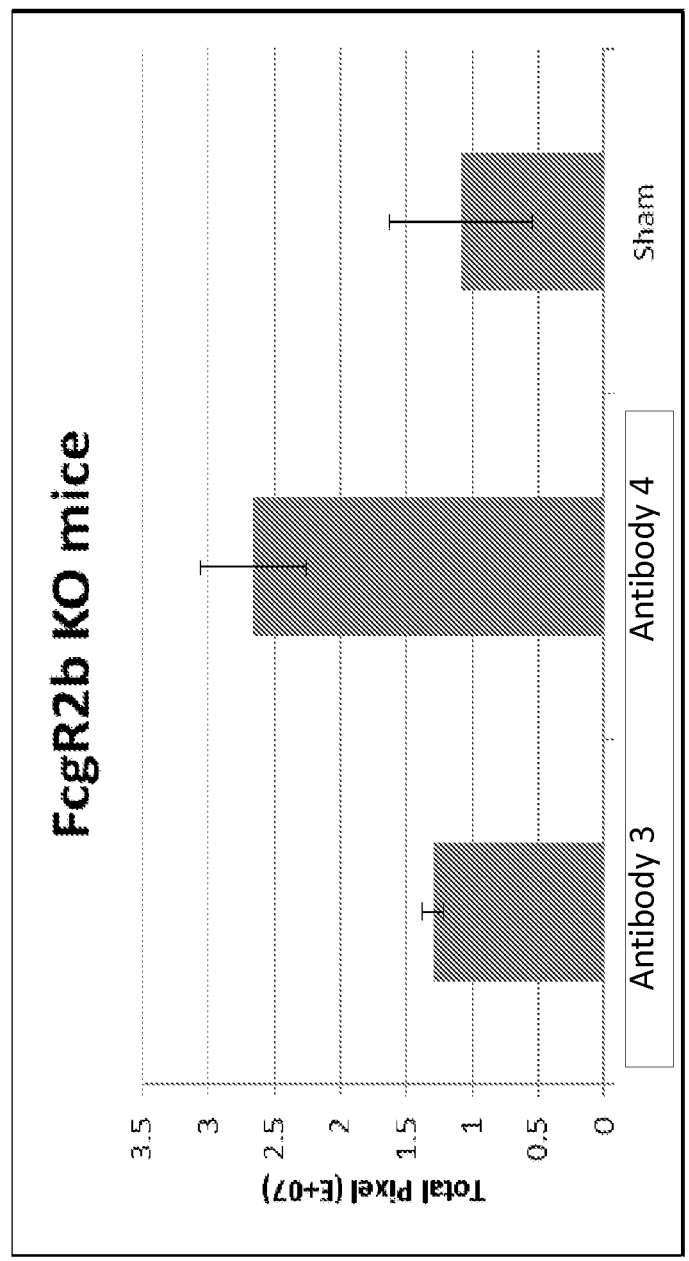
FIG. 15 is a bar graph depicting average relative SHIP expression by splenocytes obtained from FcγR2b-deficient BALB/c mice immunized with five (5) million B6 splenocytes as described above. The immunized mice were further administered an anti-CD200 antibody (with effector function) [Antibody 3; see Example 3] or a control antibody (with effector function) [Antibody 4; see Example 3]. One group of mice, "sham", received neither immunization nor antibody treatment. Each experimental group represented above included three mice. Following treatment, the spleens of the mice were harvested, fixed, and subjected to immunohistochemistry. The average relative expression from spleen cell sections was quantified using densitometry and is reported in total pixels (x E+7).

As shown in FIGS. 14 and 15, Antibody 3 administration, as compared to Antibody 4 administration, significantly reduced SHIP expression in immunized mice regardless of whether the spleen cells expressed FcγR2b. These results indicate that the reduction in SHIP expression following anti-CD200 antibody administration is due to CD200 antagonism, rather than the interaction of the antibody Fc region with Fc receptor γR2. Again, while the disclosure is not bound by any particular theory or mechanism of action, the results also support the position that the graft survival-prolonging effect of an antagonist anti-CD200 antibody therapy in mammals derives, at least in part, from modulation of SHIP expression.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

What is claimed is:

1. A method for prolonging the survival of a renal allograft, the method comprising administering to a recipient mammal in need thereof an anti-CD200 antibody as a single agent in an amount and with a frequency effective to prolong the survival of the renal allograft in the recipient mammal, wherein the recipient mammal is presensitized to the renal allograft.

2. The method of claim 1, wherein the anti-CD200 antibody is administered at least once per day for up to seven days following transplantation of the renal allograft into the recipient mammal.

3. The method of claim 1, wherein the anti-CD200 antibody is administered to the mammal at least once per day for up to 14 days following transplantation of the renal graft.

4. The method of claim 1, wherein an effective amount of the anti-CD200 antibody to prolong the survival of the renal allograft is maintained in the recipient mammal for at least 7 days.

5. The method of claim 1, wherein an effective amount of the anti-CD200 antibody to prolong the survival of the renal allograft is maintained in the recipient mammal for at least 14 days.

6. The method of claim 4, wherein a single dose of the anti-CD200 antibody is sufficient to maintain an effective amount of the anti-CD200 antibody to prolong the survival of the renal allograft in the mammal for at least 7 days.

7. The method of claim 5, wherein a single dose of the anti-CD200 antibody is sufficient to maintain an effective amount of the anti-CD200 antibody to prolong the survival of the renal allograft in the mammal for at least 14 days.

8. The method of claim 1, wherein the anti-CD200 antibody is administered to the recipient mammal prior to, and following, transplantation of the renal allograft into the recipient mammal.

9. The method of claim 1, further comprising, prior to removal from the donor mammal from which the renal allograft was obtained, administering an anti-CD200 antibody to the donor mammal.

10. The method of claim 1, wherein the renal allograft is fully MHC mismatched with respect to the recipient mammal.

11. The method of claim 1, wherein the renal allograft is an ABO-mismatch with respect to the recipient mammal.

12. The method of claim 1, wherein the anti-CD200 antibody is intravenously administered to the recipient mammal.

13. The method of claim 1, wherein the anti-CD200 antibody is subcutaneously administered to the recipient mammal.

14. A method for transplanting an allograft organ into a recipient mammal, the method comprising:
(a) prior to transplantation of an allograft organ into a recipient mammal, administering an anti-CD200 antibody as a single agent to the recipient mammal, wherein the recipient mammal is presensitized to the allograft organ;
(b) transplanting the allograft organ into the recipient mammal; and
(c) administering an anti-CD200 antibody as a single agent to the recipient mammal following transplantation of the allograft organ.

15. The method of claim 1, wherein the anti-CD200 antibody comprises a variant heavy chain constant region that has reduced effector function, as compared to the corresponding non-variant form of the heavy chain constant region.

16. The method of claim 1, wherein the anti-CD200 antibody is a whole antibody.

17. The method of claim 1, wherein the anti-CD200 antibody is a human antibody, a humanized antibody, a chimeric antibody, a rodent antibody, a deimmunized antibody, or a primatized antibody.

18. The method of claim 1, wherein the anti-CD200 antibody is a CD200-binding fragment of a whole anti-CD200 antibody.

19. The method of claim 18, wherein the CD200-binding fragment is selected from the group consisting of a single-chain antibody, an Fab, an Fab', an F(ab')$_2$, an F(ab')$_3$, an Fv, an Fd, a minibody, a diabody, and a single domain antibody.

20. The method of claim 16, wherein the anti-CD200 antibody is samalizumab.

21. The method of claim 1, wherein the antibody is administered in an amount and with a frequency sufficient to produce and maintain in the recipient mammal the occurrence of a desired immunomodulatory effect and thus prolong the survival of the allograft organ in the recipient mammal.

22. The method of claim 21, wherein the desired immunomodulatory effect is selected from the group consisting of:
(i) a decrease in the expression of CD40 by CD11c$^+$ CD49b$^-$ cells, relative to the expression level of CD40 by cells of the same histological type in the recipient mammal prior to administration of the anti-CD200 antibody and the one or more immunosuppressive agents;
(ii) a decrease in the expression of MHC class II by CD11c$^+$CD49b$^-$ cells, relative to the expression level of MHC class II by cells of the same histological type in the recipient mammal prior to administration of the anti-CD200 antibody and the one or more immunosuppressive agents;
(iii) a decrease in the expression of CD80 by CD11c$^+$ CD49b$^-$ cells, relative to the expression level of CD80 by cells of the same histological type in the recipient mammal prior to administration of the anti-CD200 antibody and the one or more immunosuppressive agents;
(iv) an increase in the expression of IL-12 by CD11c$^+$ CD49b$^-$ cells, relative to the expression level of IL-12 by cells of the same histological type in the recipient mammal prior to administration of the anti-CD200 antibody and the one or more immunosuppressive agents;
(v) an increase in the concentration of regulatory T cells, relative to the concentration of regulatory T cells of the same histological type in the recipient mammal prior to administration of the anti-CD200 antibody and the one or more immunosuppressive agents;
(vi) an increase in the concentration of Gr–1$^+$CD11b$^+$ CD45$^+$ cells, relative to the concentration of Gr–1$^+$ CD11b$^+$CD45$^+$ cells of the same histological type in the recipient mammal prior to administration of the anti-CD200 antibody and the one or more immunosuppressive agents;

(vii) a decrease in the concentration of F4/80⁺CD45⁺ cells, relative to the concentration of F4/80⁺CD45⁺ cells of the same histological type in the recipient mammal prior to administration of the anti-CD200 antibody and the one or more immunosuppressive agents;

(viii) a decrease in the concentration of CD3⁺CD25⁺ T cells, relative to the concentration of CD3⁺CD25⁺ T cells of the same histological type in the recipient mammal prior to administration of the anti-CD200 antibody and the one or more immunosuppressive agents;

(ix) a decrease in the concentration of CD3⁺CD8⁺ T cells, relative to the concentration of CD3⁺CD8⁺ T cells of the same histological type in the recipient mammal prior to administration of the anti-CD200 antibody and the one or more immunosuppressive agents;

(x) a decrease in the concentration of CD19⁺CD45⁺ cells, relative to the concentration of CD19⁺CD45⁺ T cells of the same histological type in the recipient mammal prior to administration of the anti-CD200 antibody and the one or more immunosuppressive agents; and (xi) a decrease in SHIP expression by a plurality of immune cells, relative to the expression level of SHIP in immune cells of the same histological type prior to administration of the anti-CD200 antibody and the one or more immunosuppressive agents.

23. The method according to claim 1, wherein the recipient mammal is a human and the allograft is a human allograft.

\* \* \* \* \*